United States Patent
Kat

(10) Patent No.: US 10,058,673 B1
(45) Date of Patent: Aug. 28, 2018

(54) HUMIDIFICATION CHAMBER FOR A RESPIRATORY ASSISTANCE APPARATUS

(71) Applicant: Fisher & Paykel Healthcare Limited, Auckland (NZ)

(72) Inventor: Arjen David Kat, Auckland (NZ)

(73) Assignee: Fisher & Paykel Healthcare Limited, East Tamaki (NZ)

( * ) Notice: Subject to any disclaimer, the term of this patent is extended or adjusted under 35 U.S.C. 154(b) by 0 days.

(21) Appl. No.: 15/954,392

(22) Filed: Apr. 16, 2018

Related U.S. Application Data

(63) Continuation of application No. 15/381,009, filed on Dec. 15, 2016, which is a continuation of application No. 14/426,120, filed as application No. PCT/NZ2013/000166 on Sep. 9, 2013.

(60) Provisional application No. 61/697,980, filed on Sep. 7, 2012.

(51) Int. Cl.
*A61M 16/16* (2006.01)
*A61M 16/00* (2006.01)
*A61M 16/10* (2006.01)

(52) U.S. Cl.
CPC ........ *A61M 16/16* (2013.01); *A61M 16/0066* (2013.01); *A61M 16/109* (2014.02); *A61M 2205/3382* (2013.01)

(58) Field of Classification Search
CPC ...... F24F 6/02; F24F 6/025; F24F 6/04; F24F 6/08; F24F 6/10; A61M 16/00; A61M 16/10; A61M 16/1075; A61M 16/109; A61M 16/14; A61M 16/16; A61M 2205/123; A61M 2205/3368; A61M 2205/3653

USPC ................................ 128/203.17, 203.27
See application file for complete search history.

(56) References Cited

U.S. PATENT DOCUMENTS

| | | | |
|---|---|---|---|
| 4,152,379 A | 5/1979 | Suhr | |
| 4,203,027 A | 5/1980 | O'Hare et al. | |
| 4,261,353 A * | 4/1981 | Bartels | A61M 16/16 128/200.11 |
| 4,676,237 A | 6/1987 | Wood et al. | |
| 5,209,225 A * | 5/1993 | Glenn | A61M 11/06 128/200.14 |
| 5,564,415 A * | 10/1996 | Dobson | A61M 16/16 128/200.24 |
| 5,673,687 A | 10/1997 | Dobson et al. | |

(Continued)

FOREIGN PATENT DOCUMENTS

| | | |
|---|---|---|
| CN | 102 600 540 A | 7/2012 |
| DE | 10049869 | 4/2002 |

(Continued)

OTHER PUBLICATIONS

Australian Examination Report; dated Mar. 17, 2016; 3 pages.

(Continued)

*Primary Examiner* — (Jackie) Tan-Uyen T Ho
*Assistant Examiner* — Joseph D Boecker
(74) *Attorney, Agent, or Firm* — Knobbe Martens Olson & Bear LLP

(57) ABSTRACT

A respiratory assistance apparatus includes a flow generator and a humidifier. The humidifier includes a humidification chamber. The humidification chamber comprises a water tub that is configured to receive a volume of water. A lid is hingedly coupled to the water tub for enclosing a volume contained within the water tub.

30 Claims, 34 Drawing Sheets

(56) References Cited

U.S. PATENT DOCUMENTS

| | | |
|---|---|---|
| 5,810,188 A | 9/1998 | Novakoski et al. |
| 5,943,473 A | 8/1999 | Levine |
| 6,398,197 B1 | 6/2002 | Dickinson et al. |
| 6,554,260 B1 | 4/2003 | Lipscombe et al. |
| 7,413,173 B2 | 8/2008 | DiMatteo et al. |
| 7,677,246 B2 | 3/2010 | Kepler et al. |
| 7,802,739 B2 | 9/2010 | Scorvo et al. |
| D627,044 S * | 11/2010 | Virr .............................. D23/356 |
| 8,006,691 B2 | 8/2011 | Kenyon et al. |
| 8,522,782 B2 | 9/2013 | Lewis et al. |
| 8,555,879 B2 | 10/2013 | Potharaju et al. |
| 8,631,789 B2 | 1/2014 | Virr et al. |
| 8,851,071 B2 | 10/2014 | Kuo et al. |
| 9,155,858 B2 | 10/2015 | Chen |
| 9,586,019 B2 | 3/2017 | Heine et al. |
| 9,707,370 B2 | 7/2017 | Smith et al. |
| 2004/0261951 A1 | 12/2004 | Baecke |
| 2006/0055069 A1 | 3/2006 | DiMatteo |
| 2007/0079826 A1 | 4/2007 | Kramer |
| 2007/0169776 A1 | 7/2007 | Kepler |
| 2007/0235466 A1 | 10/2007 | Fulscher et al. |
| 2008/0072900 A1 | 3/2008 | Kenyon et al. |
| 2008/0142019 A1 | 6/2008 | Lewis et al. |
| 2008/0302361 A1 | 12/2008 | Snow et al. |
| 2009/0000620 A1 | 1/2009 | Virr |
| 2009/0038614 A1 | 2/2009 | Kuo et al. |
| 2009/0272820 A1 | 11/2009 | Foley et al. |
| 2010/0065051 A1 | 3/2010 | Potharaju et al. |
| 2010/0154796 A1 | 6/2010 | Smith |
| 2010/0170510 A1 | 7/2010 | Pieri |
| 2011/0155132 A1 | 6/2011 | Virr et al. |
| 2011/0172487 A1 | 7/2011 | Khodak et al. |
| 2012/0235312 A1 | 9/2012 | Shelly |
| 2013/0008440 A1 | 1/2013 | Maurer |
| 2013/0174843 A1 | 7/2013 | Smith et al. |
| 2013/0313180 A1 | 11/2013 | Bird |
| 2015/0202402 A1 | 7/2015 | Kat |
| 2016/0022954 A1 | 1/2016 | Bath et al. |
| 2016/0129212 A1 | 5/2016 | Dimatteo et al. |
| 2016/0279678 A1 | 9/2016 | Yoshitomi et al. |
| 2017/0095636 A1 | 4/2017 | Kat |

FOREIGN PATENT DOCUMENTS

| | | |
|---|---|---|
| DE | 102 26 160 | 1/2004 |
| DE | 20 2004 004115 | 7/2004 |
| EP | 2311777 A1 | 4/2011 |
| EP | 2392375 A2 | 12/2011 |
| EP | 2540335 | 1/2013 |
| EP | 2848277 A1 | 3/2015 |
| EP | 2837399 B1 | 8/2016 |
| GB | 2 072 526 | 10/1981 |
| JP | H11-347126 | 12/1999 |
| JP | 3167708 | 5/2011 |
| WO | WO 02/066107 A1 | 8/2002 |
| WO | WO 2004/026382 | 4/2004 |
| WO | WO 2005/018724 | 3/2005 |
| WO | WO 2007/038152 A2 | 4/2007 |
| WO | WO 2008/056993 A2 | 5/2008 |
| WO | WO 2008/076230 A2 | 6/2008 |
| WO | WO 2008/148154 A1 | 12/2008 |
| WO | WO 2010/031126 A1 | 3/2010 |
| WO | WO 2013/001216 | 1/2013 |
| WO | WO 2014/038968 A1 | 3/2014 |

OTHER PUBLICATIONS

EP Search Report; dated Mar. 17, 2016; 14 pages.
International Search Report; PCT/NZ2013/000166, dated Nov. 25, 2013; 5 pages.
Written Opinion, PCT/NZ2013/000166, dated Nov. 25, 2013; 11 pages.
European Examination Report for Application No. EP 13834722.4 dated Feb. 10, 2017; 6 pages.
European Search Report for EP Application No. 16199496.7; dated Feb. 13, 2017; 15 pages.
Japanese Patent Examination Report for Application No. 2015-531035 dated Feb. 27, 2017 in 7 pages.

* cited by examiner

HUMIDIFICATION CHAMBER FOR A RESPIRATORY ASSISTANCE APPARATUS

INCORPORATION BY REFERENCE TO ANY PRIORITY APPLICATIONS

The present application is a continuation of U.S. application Ser. No. 15/381,009, filed Dec. 15, 2016, which is a continuation of U.S. application Ser. No. 14/426,120, filed Mar. 4, 2015, which is a U.S. national stage application of International Application No. PCT/NZ2013/000166, filed Sep. 9, 2013, which claims the priority benefit of U.S. Provisional Application No. 61/697,980, filed Sep. 7, 2012. Any and all applications for which a foreign or domestic priority claim is identified in the Application Data Sheet as filed with the present application are hereby incorporated by reference under 37 CFR 1.57.

BACKGROUND OF THE INVENTION

Field of the Invention

This invention relates to a humidification chamber for a respiratory assistance apparatus that provides a stream of humidified gases to a user for therapeutic purposes. The respiratory assistance apparatus may provide respiratory assistance to patients or users who require a supply of gases for respiratory therapies such as, but not limited to, humidification and/or flow therapy, Positive Airway Pressure (PAP) therapies, including but not limited to CPAP therapy, Bi-PAP therapy, and OPAP therapy, and which are typically used for the treatment of diseases such as Obstructive Sleep Apnea (OSA), snoring, or Chronic Obstructive Pulmonary Disease (COPD).

Description of the Related Art

Respiratory assistance devices or systems for providing a flow of humidified and heated gases to a patient for therapeutic purposes are well known in the art. Systems for providing therapy of this type typically have a structure where gases are delivered to a humidifier chamber from a gases source, such as a blower (also known as a compressor, an assisted breathing unit, a fan unit, a flow generator or a pressure generator). As the gases pass over the hot water, or through the heated and humidified air in the humidifier chamber, they become saturated with water vapour. The heated and humidified gases are then delivered to a user or patient downstream from the humidifier chamber, via a patient interface comprising a flexible gases conduit and a user interface.

FIG. 1 shows a schematic view of one type of known respiratory assistance system 1 for delivering humidified and heated gases to a patient. The system 1 comprises a housing 2 containing a blower unit 3 and humidifier unit 4. In operation, atmospheric air 5 is drawn into the blower unit 3. The blower unit 3 generates a pressurized air or gases stream which is delivered to the inlet 7 of a humidification chamber 8. The humidification chamber 8 comprises water and is heated by a heater pad 9. The humidified and heated gases stream 10 exits the humidification chamber via an outlet 11 of the humidification chamber and is delivered to the patient or user 12 via a flexible hose or gases conduit 13 and user interface 14 as shown. The blower unit and humidification unit are typically connected via a series of connectors and/or conduits to allow gases to pass from the blower unit to the humidifier unit.

The user interface 14 shown in FIG. 1 is a nasal mask, covering the nose of the user 12. However, it should be noted that in systems of these types, a mask that covers the mouth and nose, a full face mask, a nasal cannula, or any other suitable user interface could be substituted for the nasal mask shown. A mouth-only interface or oral mask could also be used. Also, the patient or user end of the conduit can be connected to a tracheostomy fitting, or an endotracheal intubation.

The humidification chamber 8 typically comprises a rigid plastic receptacle or container that can be filled with a volume of water. In one known form, the base of the humidification chamber comprises a circular thermally conductive metal heater plate that is fixed within a complementary aperture provided in the base of the humidification chamber via overmolding of the plastic base about the peripheral edge of the heater plate. The overmolding forms a seal at the interface between the perimeter edge of the heater plate and surrounding plastic base surface of the chamber. In use, the heater plate contacts a heater pad or heater base upon which the humidification chamber rests and heats the volume of water in the chamber via conduction. Overmolding to couple the heater plate into the base of the plastic chamber can be a complicated manufacturing process and difficult to control.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

It is an object of the present invention to provide an improved humidification chamber, or to at least provide the public with a useful choice.

SUMMARY OF THE INVENTION

In a first aspect, the present invention broadly consists in a humidification chamber for humidifying gases, comprising: a water tub that is configured to receive a volume of water; a cradle defining an open cavity within which the water tub is received; a lid hingedly coupled to the cradle for enclosing the water tub to define the interior volume of the humidification chamber and which is movable between a closed position in which the water tub is closed by the lid and an open position in which the water tub is open; one or more operable clips for securing the lid in the closed position; a gases inlet for receiving a flow of gases into the interior volume of the humidification chamber; and a gases outlet through which a humidified flow of gases may exit the interior volume of the humidification chamber.

In one form, the lid and cradle may be formed of rigid plastic. By way of example, the lid and cradle may be hingedly coupled by a living hinge and are integrally formed as a single item.

In one form, the water tub may be formed of a thermally conductive material, such as but not limited to metal.

In one form, the water tub may be defined by a base surface and a perimeter wall that extends upwardly from the base, and wherein the cradle comprises a complementary base surface and upwardly extending perimeter wall and wherein the perimeter wall of the cradle is discontinuous about the perimeter of the cradle so as to expose one or more portions of the peripheral wall of the water tub retained within the cradle. In such forms, a heat transfer contact surface may protrude from the base surface of the water tub and the cradle may be provided with a complementary aligned aperture through which the contact surface of the water tub extends such that it protrudes beyond the underside of the base surface of the cradle.

In one form, the water tub may be releasably received within the cradle by slidable engagement.

In one form, the gases inlet and gases outlet may be provided on opposite sides of the lid. In such forms, the lid may comprise a vertical flow plane that extends downwardly from the underside of the lid in a central region of the lid.

In one form, the gases inlet may be coupled to an inlet conduit that extends between an inlet end at the gases inlet and an outlet end located at or toward an upper central region of the interior volume of the humidification chamber and adjacent a first side surface of the vertical flow plane such that the incoming gases flow enters the interior volume of the humidification chamber at that upper central region. Additionally, a flow director formation in the form of an inverted curved ramp surface may be located between the outlet end of the inlet conduit and the first side surface of the vertical flow plane.

In one form, the gases outlet may be coupled to an outlet conduit that extends between an inlet end located at or toward an upper central region of the interior volume of the humidification chamber and adjacent a second side of the vertical flow plane and an outlet end at the gases outlet.

In one form, the lid may comprise one or more water fill apertures and at least one water fill aperture comprising an associated maximum water level indicator comprising a tab member that is supported from the underside of the lid such that it extends into the field of view of the interior volume of the humidification chamber visible directly through the water fill aperture.

In one form, the humidification chamber may have an overall shape defined by front and end walls between which side walls extend, and the walls extending between an upper surface of the lid and base surface of the cradle, and wherein the lid is hingedly coupled to the cradle at the rear end of the humidification chamber, and at least one operable clip is provided at the front end of the humidification chamber.

In one form, the chamber may comprise at least one operable clip provided in the form of a torsion clip that is mounted to either the lid or cradle and which is configured to engage with a catch provided on either the cradle or lid, respectively. By way of example, at least one operable clip may be provided that is hingedly coupled to the lid or cradle and which is configured to engage with a catch provided on either the cradle or lid, respectively.

In a second aspect, the present invention broadly consists in a humidification chamber for humidifying gases, comprising: a water tub that is configured to receive a volume of water; a lid hingedly coupled to the water tub for enclosing the water tub to define the interior volume of the humidification chamber and which is movable between a closed position in which the water tub is closed by the lid and an open position in which the water tub is open; one or more operable clips for securing the lid in the closed position; a gases inlet for receiving a flow of gases into the interior volume of the humidification chamber; and a gases outlet through which a humidified flow of gases may exit the interior volume of the humidification chamber.

In one form, the lid may be formed from rigid plastic. By way of example, the water tub may be formed of rigid plastic and may comprise a base surface and a perimeter wall that extends upwardly from the base, and wherein the base surface comprises a heater plate. In one form, the heater plate may be secured within an aperture of the base surface of the water tub by overmolding. In one arrangement, a peripheral coupling surface of the heater plate may be secured within a periperhal engagement portion of the base surface about the aperture of the water tub by overmolding such that the thickness of the engagement portion is greater than the thickness of remaining base surface. By way of example, the engagement portion may comprise an upper portion above the coupling surface of the heater plate and a lower portion below the coupling surface, and wherein the upper portion is at least as thick as the remaining base surface. By way of example, the heater plate may be metallic.

In one form, the water tub may further comprise a step formation about the inner surface perimeter of the wall of the water tub, the step formation being configured at a height above the base surface of the water tub corresponding to a maximum fill line indicator.

In one form, the base surface of the water tub may be domed such that it curves outward toward a central apex defined by the heater plate.

In one form, the perimeter wall of the water tub may comprise one or more reinforced regions. By way of example, the reinforced region(s) of the perimeter wall may comprise corrugated surfaces of alternating ridges and furrows.

In one form, the lid and water tub may be hingedly coupled by a living hinge and are integrally formed as a single item.

In one form, the gases inlet and gases outlet may be provided on opposite sides of the lid. In such forms, the lid may comprise a vertical flow plane that extends downwardly from the underside of the lid in a central region of the lid. In one arrangement, the vertical flow plane may further comprise a pair of side baffles that each extend from a respective side edge of the vertical flow plane toward the side of the lid comprising the gases inlet.

In one form, the gases inlet may be coupled to an inlet conduit that extends between an inlet end at the gases inlet and an outlet end located at or toward an upper central region of the interior volume of the humidification chamber and adjacent a first side surface of the vertical flow plane such that the incoming gases flow enters the interior volume of the humidification chamber at that upper central region. Additionally, a flow director formation in the form of an inverted curved ramp surface may be located between the outlet end of the inlet conduit and the first side surface of the vertical flow plane.

In one form, the gases outlet may be coupled to an outlet conduit that extends between an inlet end located at or toward an upper central region of the interior volume of the humidification chamber and adjacent a second side of the vertical flow plane and an outlet end at the gases outlet.

In one form, the gases outlet of the lid may comprise an engagement surface about the perimeter of the gases outlet that is tilted outwardly such that an upper portion of the engagement surface is displaced further outward from the lid than a lower portion of the engagement surface.

In one form, the lid may comprise one or more water fill apertures and at least one water fill aperture comprising an associated maximum water level indicator comprising a tab member that is supported from the underside of the lid such that it extends into the field of view of the interior volume of the humidification chamber visible directly through the water fill aperture.

1. In one form, the humidification chamber may have an overall shape defined by front and end walls between which side walls extend, and the walls extending between an upper surface of the lid and base surface of the water tub, and wherein the lid is hingedly coupled to the water tub at the rear end of the humidification chamber, and at least one operable clip is provided at the front end of the humidification chamber.

In one form, the chamber may comprise at least one operable clip provided in the form of a torsion clip that is mounted to either the lid or water tub and which is configured to engage with a catch provided on either the water tub or lid, respectively. By way of example, at least one operable clip may be provided that is hingedly coupled to the lid or water tub and which is configured to engage with a catch provided on either the water tub or lid, respectively.

In one form, the chamber may further comprise a seal about the perimeter of the chamber between the lid and water tub to seal the chamber when it is in a closed position.

In a third aspect, the present invention broadly consists in a respiratory assistance device configured to provide a heated and humidified gases stream, comprising: a device gases inlet configured to receive a supply of gases; a blower configured to generate a pressurised gases stream from the supply of gases; a humidifier configured to heat and humidify the pressurised gases stream; a device gases outlet for the heated and humidified gases stream; and a flow path for the gases stream through the respiratory device from the gases inlet though the blower unit and humidification unit to the gases outlet, and wherein the humidifier comprises a sealable humidification compartment that is configured to receive and retain a removable humidification chamber according to either of the first or second aspects of the invention.

In one form, the humidification compartment may comprise a lid that is movable between an open position to enable removal of the humidification chamber and a closed position to seal the humidification chamber within the humidification compartment.

In one form, the humidification compartment may comprise a gases inlet connected to the flow path to receive the pressurised gases stream from the blower to create a pressurised humidification compartment and a gases outlet connected to the device gases outlet of the flow path.

In one form, the gases inlet of the humidification chamber may be open within the humidification compartment to receive an incoming flow of gases from within the pressurised humidification compartment.

In one form, the gases outlet of the humidification compartment may be sealingly connected to the gases outlet of the humidification chamber.

In one form, the humidification compartment may comprise a heater pad upon which the humidification chamber sits.

In one form, the device may be contained within a single housing.

In one form, the device may be a CPAP respiratory device.

The humidification chamber of the third aspect of the invention may have any one or more of the features mentioned in respect of either of the first and second aspects of the invention.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

As used herein the term "and/or" means "and" or "or", or both.

As used herein "(s)" following a noun means the plural and/or singular forms of the noun.

The invention consists in the foregoing and also envisages constructions of which the following gives examples only.

BRIEF DESCRIPTION OF THE DRAWINGS

Preferred embodiments of the invention will be described by way of example only and with reference to the drawings, in which.

DETAILED DESCRIPTION OF PREFERRED EMBODIMENTS

Overview

The invention relates to a humidification chamber for a respiratory assistance apparatus (respiratory device) that supplies a flow or stream of heated and humidified respiratory gases to a user or patient for respiratory therapies, such as, but not limited to, CPAP therapy.

Figure 1:
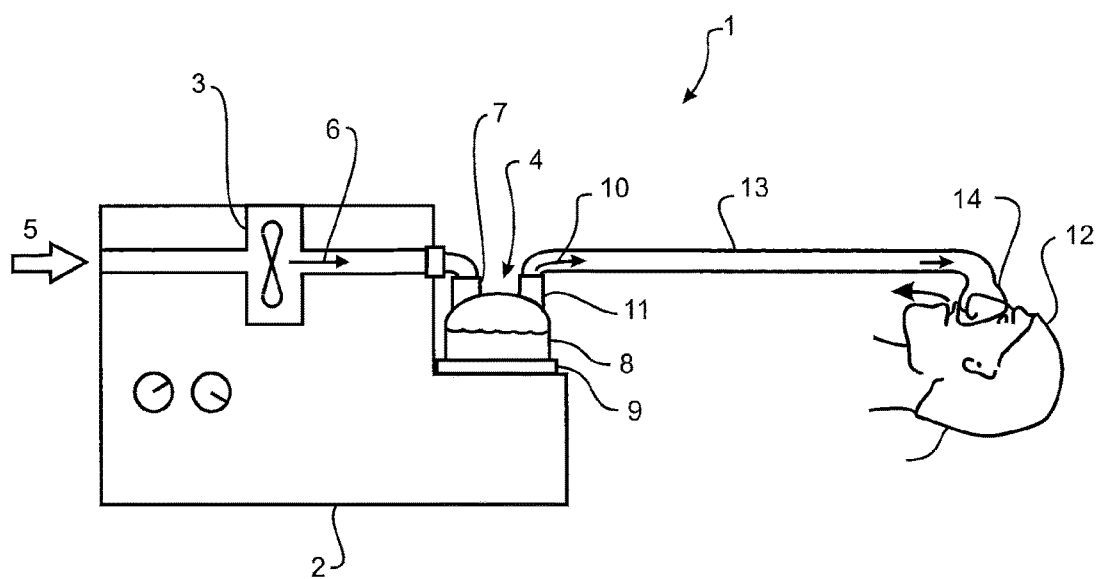
FIG. 1 shows a schematic view of a known form of respiratory assistance apparatus in which the blower unit and humidifier unit are integrated into a single main housing.
Figure 2:
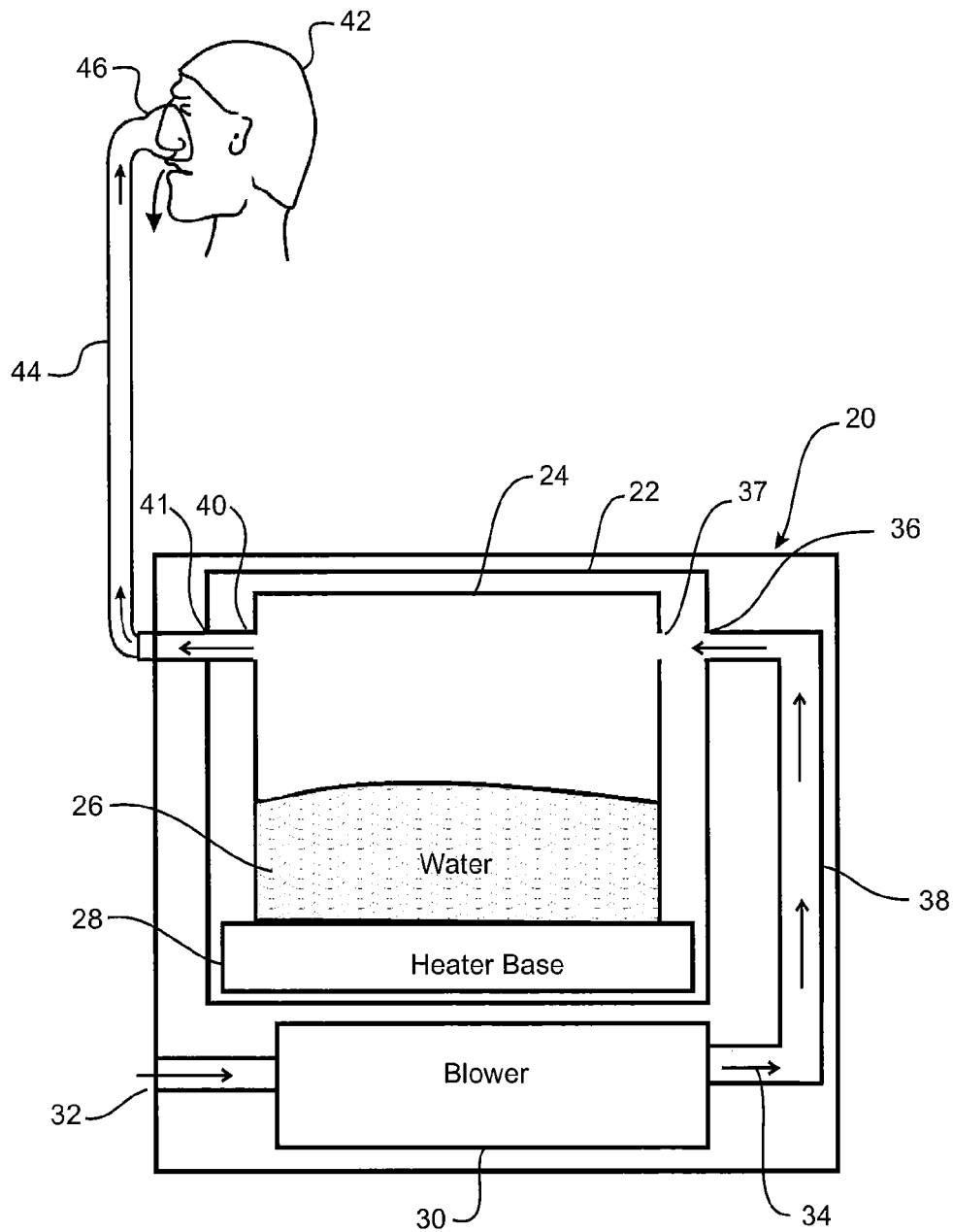
FIG. 2 shows a schematic view of the main components and configuration of a respiratory assistance apparatus which may utilise a humidification chamber of the invention.

For context, FIG. 2 shows an example of a typical schematic configuration of a respiratory device 20 within which the humidification chamber of the invention may be employed, although this is not intended to be limiting to the uses of the humidification chamber. The respiratory device 20 comprises a humidification unit or humidification compartment 22 that receives and retains a removable humidification chamber 24 in use. In this embodiment, the humidification compartment 22 may be formed within the housing of the respiratory device and may be an openable compartment having a lid so the humidification chamber 24 within the humidification compartment 22 may be accessed for removal for cleaning or filling. Typically the humidification compartment 22 is sealed and/or pressurised when the lid is closed. The humidification chamber 24 is filled with a volume of water as indicated at 26 and the chamber 24 rests upon a heater pad or heater base 28. As is known in the art, the heater pad 28 is powered to heat the water 26 in the humidification chamber 24 during use via heat transfer through the base of the humidification chamber 24 of which at least a portion is thermally conductive.

The respiratory device 20 comprises a blower 30 which draws atmospheric air or other therapeutic gases through an inlet 32 and generates a pressurised gases stream 34 at an outlet of the blower. The outlet of the blower 30 is fluidly connected to an inlet 36 of the humidification compartment 22 via connecting conduits 38 extending to the inlet 36 of humidification compartment 22. As the humidification compartment is sealed when closed, the gases stream 34 entering the inlet 36 pressurises the compartment and gases flow into the open gases inlet 37 of the humidification chamber 24. It will be appreciated that in alternative embodiments, the inlets 36,37 of the compartment 22 and chamber 24 may be sealingly connected by a connector or other sealing configuration.

The pressurized gases stream passes through the humidification chamber 24 and exits via gases outlet 40 of the humidification chamber. In this embodiment, the gases outlet 40 of the chamber 24 is sealingly connected to or sealingly engaged with an outlet 41 of the humidification compartment 22 as shown. It will be appreciated that in alternative embodiments, the outlets 40, 41 of the compartment 22 and chamber 24 need not be sealingly connected by a connector or otherwise sealingly engaged. In the embodiment shown, the outlet 41 of the humidification compartment 22 is fluidly connected via connectors and/or conduits to a patient interface for delivery to a patient 42. The patient interface typically comprises a flexible gases conduit 44 coupled at one end to the main gases outlet of the respiratory device 20 and to a user interface 46 at the other end.

In the following embodiments, the humidification chamber 24 is typically received and retained within a complimentary enclosed and sealable humidification compartment 22 formed in the housing of the respiratory device 20. However, it will be appreciated that the humidification chamber 24 could alternatively be received and retained in an open or exposed compartment or on a support platform comprising the heater pad 28 in alternative embodiments with the gases inlet of the chamber being connected to the blower outlet by conduits and/or connectors and the gases outlet of the chamber being connected by conduits and/or connectors directly or indirectly to the patient interface.

First Embodiment Humidification Chamber—Discontinuous Cradle with Lid

Referring to FIGS. 3-20 a first embodiment of the humidification chamber 50 will be explained in further detail. As explained above, the humidification chamber 50 is configured to be received and retain within a complimentary humidification compartment (not shown) provided within the housing of the respiratory device. Typically the compartment comprises a heater base or heater pad upon which the humidification chamber sits. The humidification compartment is accessible via an openable lid to enable the humidification chamber 50 to be inserted and removed as required, for example for cleaning and/or refilling.

Figure 3:
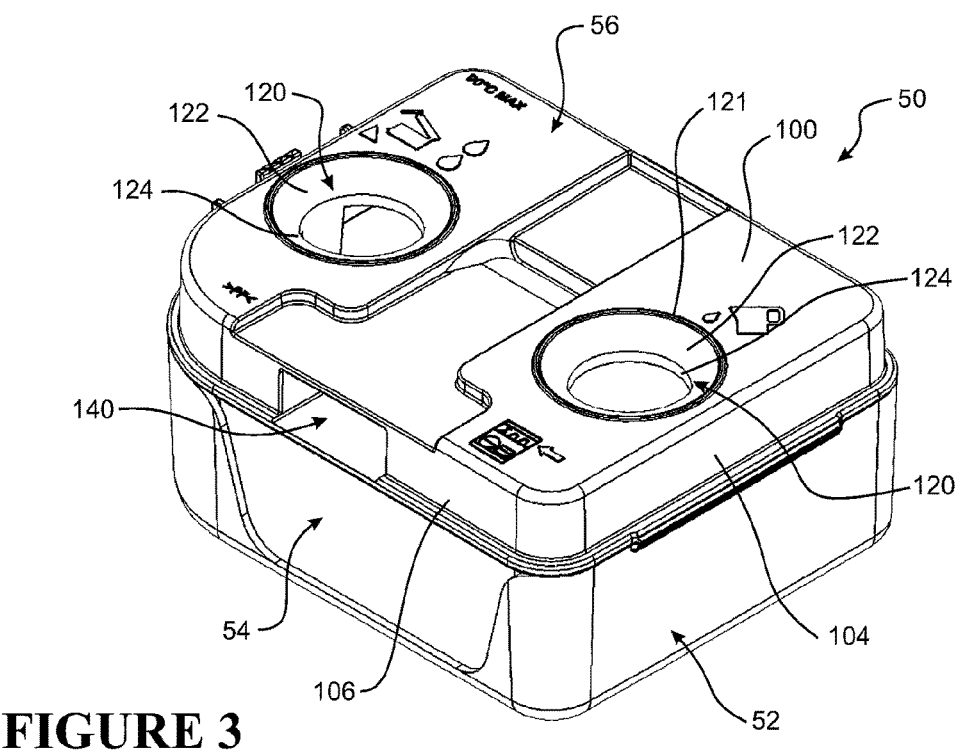
FIG. 3 shows a lower perspective view of a closed humidification chamber in accordance with a first embodiment of the invention comprising a lid, discontinuous cradle and water tub.

As shown in FIG. 3, the humidification chamber or chamber assembly 50 comprises a cradle or lower part generally indicated at 52 that is shaped to receive and retain a complimentary sized and dimensioned water tub or container 54. An upper part or lid 56 is hingedly coupled to the cradle 52 and is moveable between a closed position (shown in FIG. 3) in which the lid securely retains the water tub 54 within the cradle 52 and an open position (see FIG. 14 for example) in which the lid is pivoted away from the cradle 52 to enable the water tub 54 to be removed from the cradle for cleaning, refilling or replacement for example. As will be explained later, the lid may comprise baffling in the form of a configuration of conduits and/or flow planes and guides to control the flow path of the gases stream through the chamber between the inlet and outlet.

In this embodiment, the cradle 52 and lid 56 are formed of a rigid plastic by injection moulding or the like. Typically, the cradle 52, lid 56 and hinged coupling between the two components are integrally formed together as a single item, although in alternative embodiments the lid and cradle may be formed as separate parts and then hingedly coupled via one or more hinges. The lid and/or cradle may be substantially transparent or formed as opaque depending on design requirements. The water tub or chamber base 54 is formed of a rigid and thermally conductive material, typically pressed or shaped from sheet metal, such as aluminium, stainless steel or any other suitable material, or could be formed by die casting for example.

It will be appreciated that in alternative embodiments, the cradle 52, lid 56 and water tub 54 could be formed from other materials or in other ways. For example, the cradle 52 and lid 56 could be formed by vacuum forming. The cradle and/or lid could also be formed from metal, whether pressed from sheet metal or formed from die casting for example. The water tub could alternatively be formed from a heat conductive plastic in alternative embodiments.

Shape of the Humidification Chamber

Figure 4:
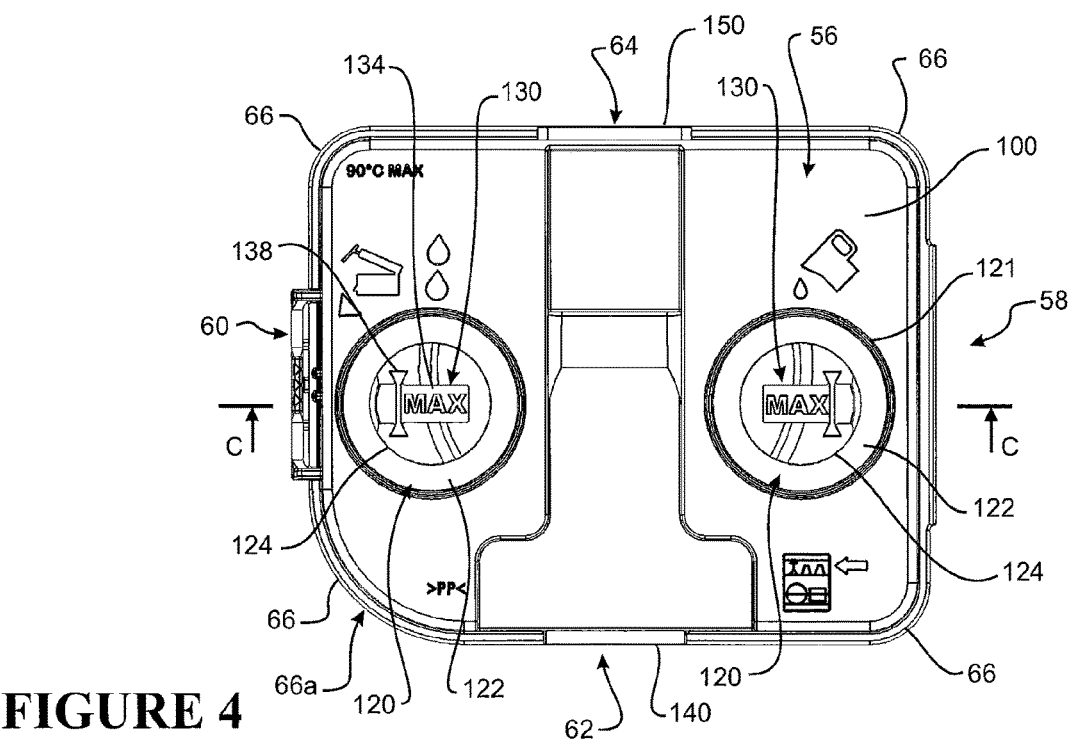
FIG. 4 shows a plan view of the humidification chamber of FIG. 3.
Figure 5:
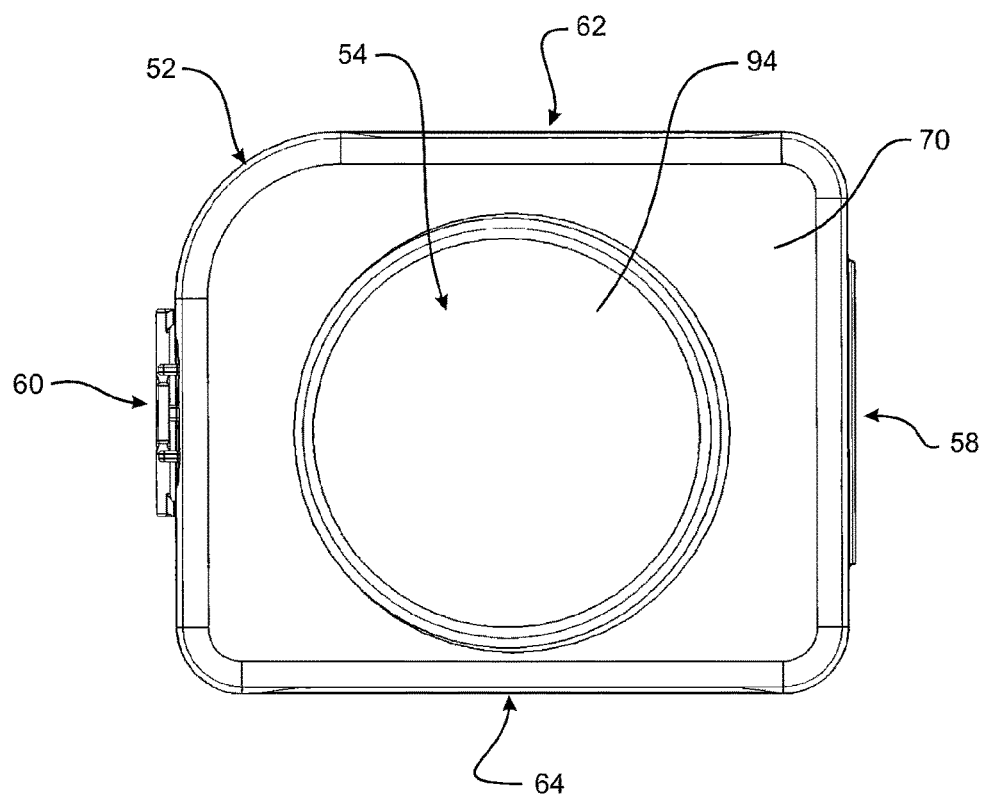
FIG. 5 shows an underside view of the humidification chamber of FIG. 3.

In this embodiment, the overall shape of the humidification 50 is substantially rectangular as shown in the plan view of FIG. 4. The humidification chamber 50 is defined by first 58 and second 60 end between which first 62 and second 64 sides extend. In this explanation, the first end 58 is considered the rear end and the second end 60 is considered the front end of the humidification chamber. The first side 62 may be considered the inlet side of the humidification chamber as it contains the inlet through which the pressurized gases stream from the blower enters the humidification chamber. The second side 64 may be considered the outlet side of the humidification chamber as it contains the outlet for the humidified gases stream which exits the humidification chamber. It will be appreciated that in an alternative description of the chamber, the ends could be considered the sides and vice versa, depending on the context.

In this embodiment, the corners joining the ends 58,60 and sides 62,64 are curved or rounded as generally indicated at 66, although this is not essential and the corners may be right-angle corners or any other profiled shape. In this embodiment, the corner 66a joining the front end 60 and inlet side 62 is larger than the remaining corners, although this is not essential. It will be appreciated that in alternative embodiments the humidification chamber assembly may be formed in any desired shape or profile, including circular or otherwise and that the same principals of construction and configuration will generally apply.

Cradle

The cradle 52 is configured to receive and retain the water tub 54 which has a complimentary shape and slightly smaller dimensions so that it can slide down into the open cavity formed by the cradle. The tightness of the fit between the water tub 54 and cradle 52 may be varied. In some embodiments it may be snug with a friction fit and in other embodiments it may be a loose fit such that the water tub may easily slide into and out of the cradle preferably without any or minimal force or pressure applied by the user to assemble or release the parts. When the chamber is closed, the cradle acts to hold the water tub securely and accurately up against the lid. In particular, the cradle typically holds the water tub up to the lid around the full mouth of the chamber to prevent/minimise splash over of water between the lid and water tub. The cradle also has the dual function of holding the water tub in place while also hinging the lid, and keeps the lid and water tub aligned so that when the user goes to close the chamber they do not have to align the lid and water tub.

Figure 13:
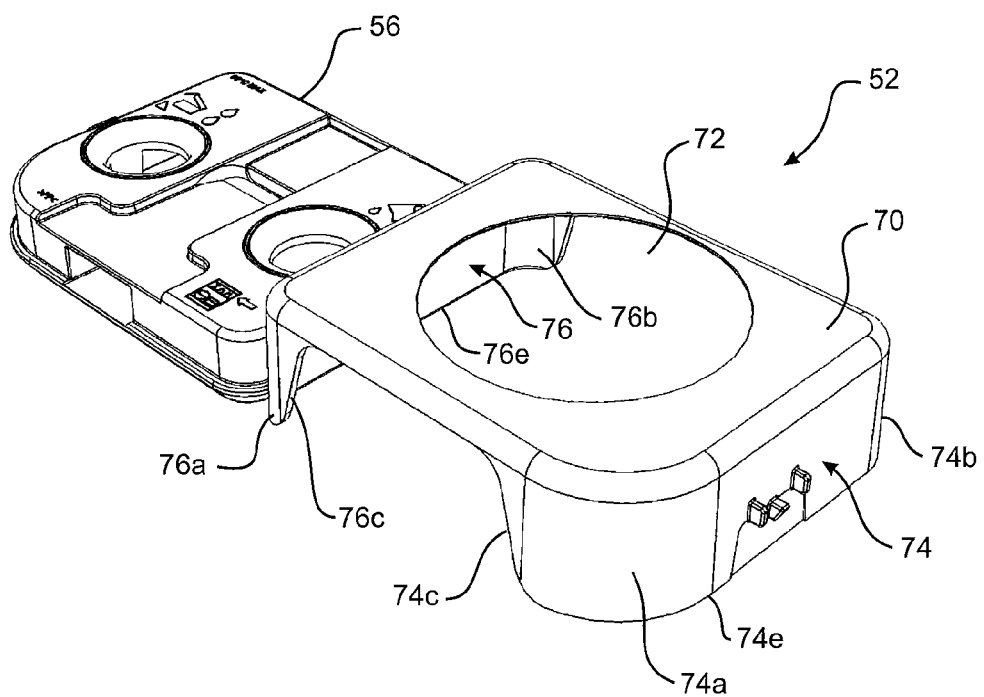
FIG. 13 shows one perspective view of the cradle and lid of the humidification chamber of FIG. 3 in an open position.

Referring to FIG. 13, in this embodiment, the cradle 52 comprises a base or bottom surface 70 upon which the base or bottom surface of the water tub 54 rests. The base 70 of the cradle 52 also comprises a central aperture 72 which enables the heater base or heater pad of the respiratory device to contact a portion of the base of the water tub 54 for heat transfer to heat up the water volume in the water tub 54 as will be explained in further detail later. The cradle 52 has a discontinuous perimeter wall, which in this embodiment is in the form of at least one pair of opposed walls that extend upwardly from the perimeter of the base 70 to form a cradle-like structure with an open receiving cavity. In this embodiment, the cradle 52 comprises front 54 and rear 76 walls that extend upwardly from the base 70. The end wall formations 74, 76 extend along each respective front and rear end of the cradle and extend about at least portion of the corner perimeter of the cradle 52 such that each end wall formation comprises a central planar portion which extends into curved corner portions identified at 74a, 74b and 76a, 76b at each respective end of the central planar portion.

Figure 6:
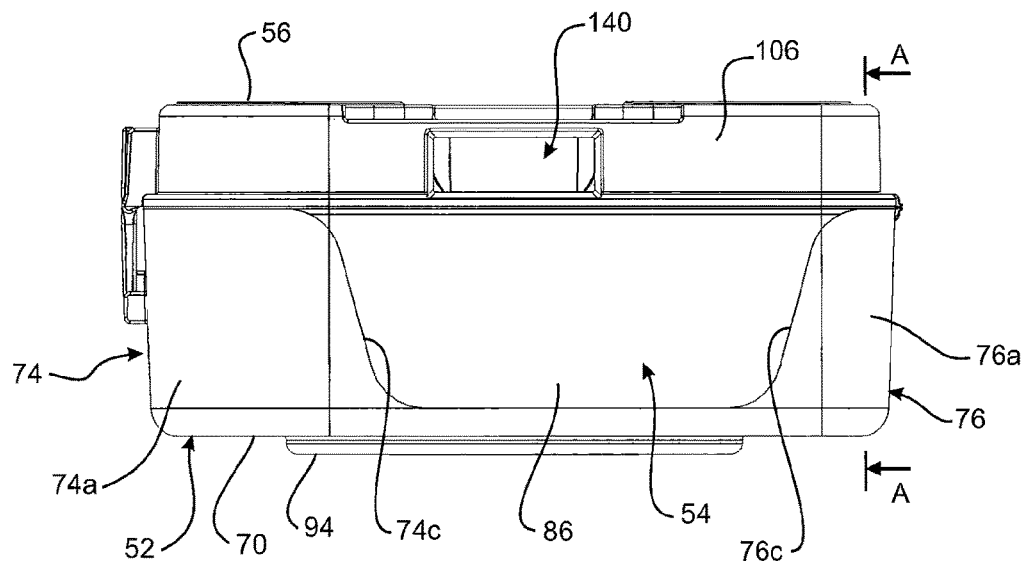
FIG. 6 shows a side elevation view of the gases inlet side of the humidification chamber of FIG. 3.

In this embodiment, the end wall formations 74, 76 each extend about the entire corner region of the cradle and terminate along respective sides of the cradle prior to meeting each other to thereby provide open side wall formations in the cradle which expose the water tub 54 when retained in the cradle 52. For example, FIG. 6 shows the inlet side of the cradle 52 with the front 74 and rear 76 end walls extending about the respective corners 74a, 76a of the cradle and along the side of the cradle, and each terminated at a sloped curved edge 74c, 76c extending downwardly from the upper edge of the cradle to the base 70. It will be appreciated that the terminating edges 74c, 76c need not necessarily be declining at an angle with a curving profile but maybe abrupt vertical edges in alternative forms of the cradle if desired Likewise, a similar configuration is provided on the opposite outlet side of the cradle shown in FIG. 7. On the outlet side, the end walls 74 and 76 also extend about respective corners 74b, 76b and terminate at sloped curved edges 74d, 76d which extend from the upper edge of the cradle down to the base.

Figure 7:
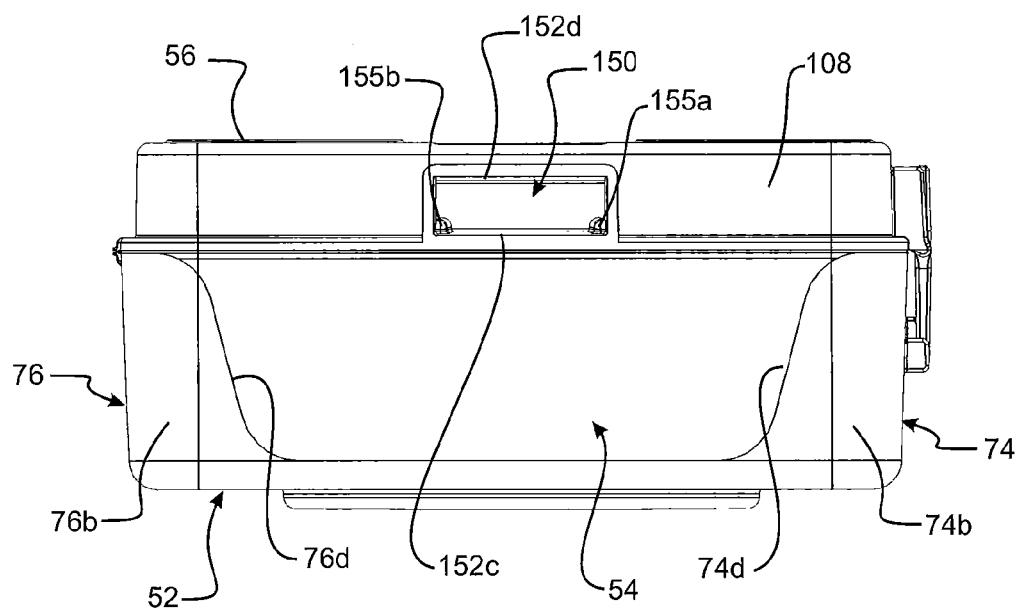
FIG. 7 shows a side elevation view of the gases outlet side of the humidification chamber of FIG. 3.

The cradle 52 substantially encapsulates the water tub 54 about at least the opposing end walls of the water tub and additionally corner portions of the water tub 54. As shown in FIGS. 6 and 7, in this embodiment the perimeter wall of the cradle is discontinuous such that the walls of the cradle do not encircle or surround the entire perimeter walls of the water tub 54 completely or continuously, thereby leaving a portion or portions of the water tub wall exposed (not covered by the cradle). In this embodiment, the cradle walls are discontinuous on each side of the cradle such that the majority of the side walls of the water tub 54 are exposed (i.e. not covered by the cradle walls). For example, in this embodiment the opposed end walls 74 and 76 terminate at edges on the sides of the cradle at or towards their respective ends. It will be appreciated that displacement or distance between the terminating edges of the end walls 74 and 76 on each side may be varied to expose more or less of the water tub side wall portion as desired. For example, either or both of the end walls may terminate at or toward the center of the wall or more toward the corner portion of the walls.

In use, the cradle provides a thermally insulated barrier or surface which the user may grasp or hold the humidification chamber by after removing the chamber from the respiratory device for refilling or cleaning for example. This enables the user to avoid direct contact with the heated thermally conductive water tub, and thereby avoid potential burns or discomfort. Additionally, the removability of the water tub from the cradle allows for both parts to be cleaned thoroughly.

Water Tub

Figure 11A:
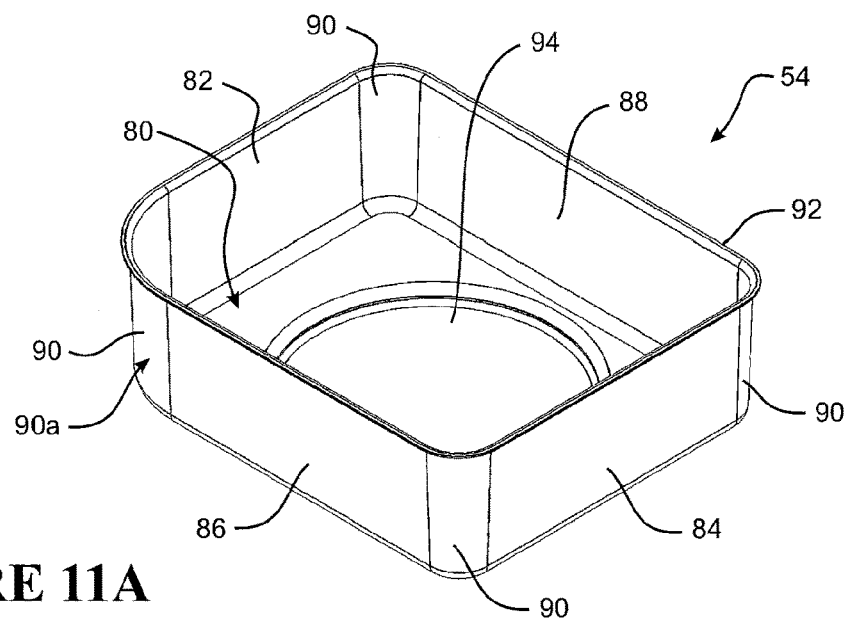
FIGS. 11A, 11B and 11C show upper perspective, side elevation, and lower perspective views of the water tub of the humidification chamber of FIG. 3.
Figure 11B:
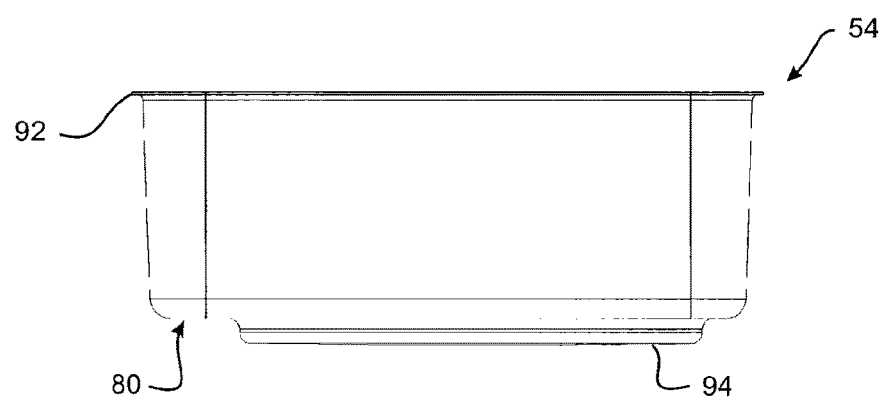
Figure 11C:
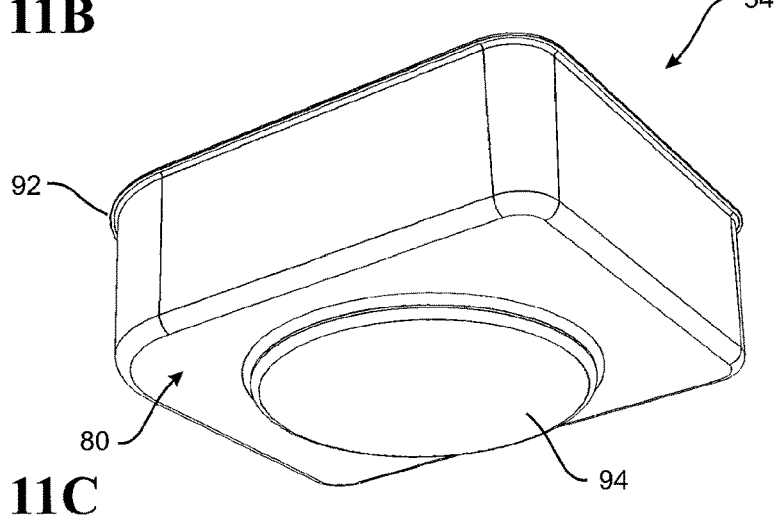

Referring to FIGS. 11A-11C, the water tub 54 is shown in isolation. As previously mentioned, water tub 54 is typically formed from sheet metal or similar and operates as a receptacle or container for holding a volume of liquid, such as water. As shown, the water tub 54 has a shape that is complimentary to the cradle such that the water tub 54 may be snugly received into the cradle 52, for example via slidable engagement with a friction fit.

In this embodiment, the water tub 54 is substantially rectangular with a base or base surface 80 from which upwardly extending perimeter walls extend. In particular the water tub 54 comprises front 82 and rear 84 walls and first 86 and second 88 side walls extending between the end walls. The corner wall portions 90 joining the end and side walls are preferably curved or round with a similar curvature or radius that compliments the overall cradle plan view shape explained with reference to FIG. 4 previously. As shown, one of the corners 90a is larger in radius than the remaining corners to complement the larger corner 66a of the cradle. This configuration allows the water tub to be received in the cradle in a single orientation only to assist the user when assembling the parts together such that the inlets and outlets of the chamber and humidification compartment are correctly aligned with each other. It will be appreciated that the water tub, cradle and lid may have any other profiled corners, including 90° right-angle corners and the profiled corners may be uniformed or non-uniformed from corner to corner.

Referring to FIG. 11B the upper edge of the perimeter walls is provided with a continuous outwardly extending lip, flange or rim 92. In this embodiment, the lip 92 extends substantially horizontally or transversely outward from the vertical perimeter wall at the upper edge of the perimeter wall. The perimeter lip 92 is optional. When provided, it is configured to engage, abut or rest upon the upper edges 74e, 76e (see FIGS. 13 and 14) of the end walls 74 and 76 of the cradle 52 and which is more readily visible in the cross-sectional view of FIG. 10, for example.

The water tub 54 is provided with a heat transfer contact surface or portion 94 that protrudes from the underside of the base surface 80. The contact surface 94 is preferably integrally formed with the remainder of the water tub. For example, the contact surface 94 may be pressed out from the base surface 80. In this embodiment, the contact surface 94 is circular and of a diameter substantially complimentary to the central aperture 72 provided in the base surface 70 of the cradle 52 (see FIG. 13). In particular, the contact surface 94 of the water tub 54 is substantially aligned with the complimentary aperture 72 of the cradle 52 and is of a depth relative to remainder of the base surface 80 that enables it to extend through aperture 72 so as to protrude below the underside of base surface 70 of the cradle as shown in FIG. 6. When the humidification chamber 50 is inserted into a complimentary humidification compartment in the respiratory device, the protruding contact surface 94 of the water tub 54 rests upon or abuts a heater base or pad within the compartment, which may be of a complimentary size and shape, although this is not essential. The heat from the heater base is then transferred through the thermally conductive (e.g. metal) contact surface 94 to the volume of water within the water tub via conduction as will be appreciated.

In alternative embodiments, the contact surface need not necessarily protrude beyond the remainder of base surface 80 of the water tub. For example, in one alternative embodiment, the base surface 80 may be planar with a flush contact surface 94 and the heater base or pad may be shaped in such that it protrudes through the aperture 72 of the cradle for engagement or contact with the base surface 80 of the water tub 54. In a further alternative embodiment, the contact surface 94 may be recessed relative to the remaining underside of the base surface 80 of the water tub, i.e. such that it protrudes upwardly into the water tub. With such an embodiment, again the complimentary heater base or pad may be configured with a height and shape that enables it to protrude through aperture 72 in the cradle for engagement into the recess or cavity created by the recessed contact surface in the base of the water tub 54.

In the above embodiments, the contact surface and related componentry is described for a circular contact surface and heater pad, although it will be appreciated that any other alternative shape of contact surface may be employed, including square, rectangular or any other suitable shape.

Lid

Referring to FIGS. 3 and 4 the lid 56 of the humidification chamber 50 has a shape when viewed in plan (see FIG. 4) substantially corresponds to the shape of the cradle 52 and water tub 54. In this embodiment, the lid comprises a main body portion 100 which forms upper surface or top of the humidification chamber and has a substantially rectangular overall shape with rounded corners which corresponds to the outer shape of cradle 52 and water tub 54. Extending downwardly from the main portion 100 are perimeter walls. For example, front 102 and rear 104 end walls are provided at each end of the main portion as can be seen most clearly in FIG. 18. Additionally, first 106 and second 108 side walls extend along the sides of the main body portion 100 between the front and rear end walls 102, 104. The first side wall 106 is on the inlet side of the humidification chamber and the second side wall 108 is on the outlet side of the humidification chamber. Rounded corner wall portions 110 are also provided which join the side and end walls to form an overall perimeter wall extending vertically downwardly from the substantially horizontally extending main body portion 100.

Figure 10:
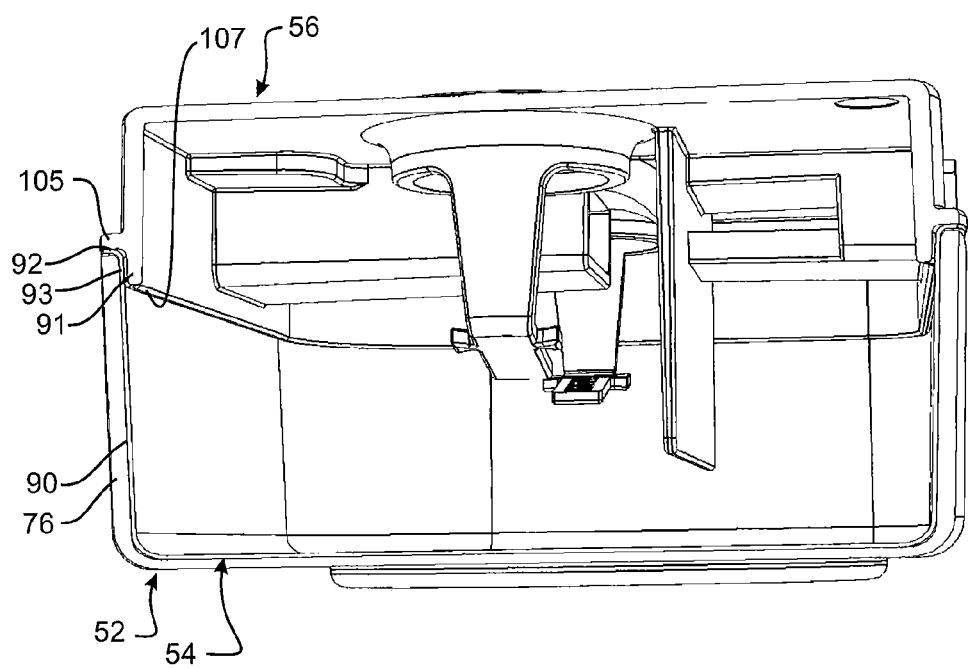
FIG. 10 is a perspective cross-sectional view of the closed humidification chamber through line AA of FIG. 6.

In this embodiment, a perimeter ledge or flange 105 (see FIGS. 10 and 18) is provided about the entire perimeter of the lid. The ledge 105 extends outwardly from perimeter walls and in a substantially horizontal direction in this embodiment, although an angled ledge may be used as an alternative. The ledge is provided towards but displaced from the lower edge 107 of the perimeter vertical walls of the lid 56. In use, the lower surface of the ledge 105 of the lid is configured to abut or engage with the upper surface of the rim 92 of the water tub 54. In this embodiment, the outer surface of the lower perimeter wall portion 91 of the lid 56 below the ledge 105 has some clearance (i.e. is displaced by a small amount) from the adjacent inner surface of the upper perimeter wall portion 93 of the water tub below the rim 92 as shown in FIG. 10. This allows the lid to engage and disengage with the water tub without the user being required to apply significant force. In this embodiment, the lower perimeter wall portion 91 of the lid acts as a water guard or shield in that it deflects water from splashing out between the lid and water tub, and additionally assists in aligning the lid into engagement with the water tub when a user is closing the chamber. It will be appreciated that other embodiments may be configured for a tighter friction fit such that the lower perimeter wall portion 91 of the lid abuts or contacts the upper perimeter wall portion 93 of the water tub.

Water Fill Holes

Referring to FIGS. 3 and 4, the lid 56 is provided with one or more water fill apertures or holes through which water may be poured to fill or refill the water tub 54 of the humidification chamber. In this embodiment, two identical water fill holes generally indicated at 120 are provided, one at or toward front end of the lid and the other at or toward the rear end of the lid, although the location of the water fill holes may be varied from this configuration. In this embodiment, each water fill hole is provided by a funnel-like formation which extends into the humidification chamber from the main body portion 100 of the lid. For example, each water fill hole 120 is provided with a frusto-conical formation 122 having a first end flush with the main body portion 100 of the lid and extending down into the humidification chamber with a progressively reducing diameter to terminate at a second end corresponding to the water fill aperture edge 124, which in this case is circular. It will be appreciate that the funnel-like formation of the water fill holes is optional, but helps reduce splashing or spillage during filling of the chamber. In an alternative embodiment, the water fill holes may simply be apertures formed in the main body portion, circular or otherwise, without any such guiding funnel-like formation.

In this embodiment, each water fill hole 120 is provided with one or more concentric circular raised sealing ribs 121 or protrusions extending about the perimeter of the water fill hole. These sealing ribs 121 may be integrally formed with the lid or attached to the lid. The sealing ribs 121 may be formed of a rigid or hard plastic such that a soft seals may sealingly engage with the ribs to close the water fill holes. By way of example, the soft seals may be provided on the lid of the humidification compartment within which the chamber is located in use. In an alternative embodiment, the ribs 121 may be a soft overmolded plastic or rubber or silicone for sealingly engaging with a hard surface or formations provided on the lid of the humidification compartment to close the water fill holes when in use within the respiratory device.

Water Level Indicators

Figure 18:
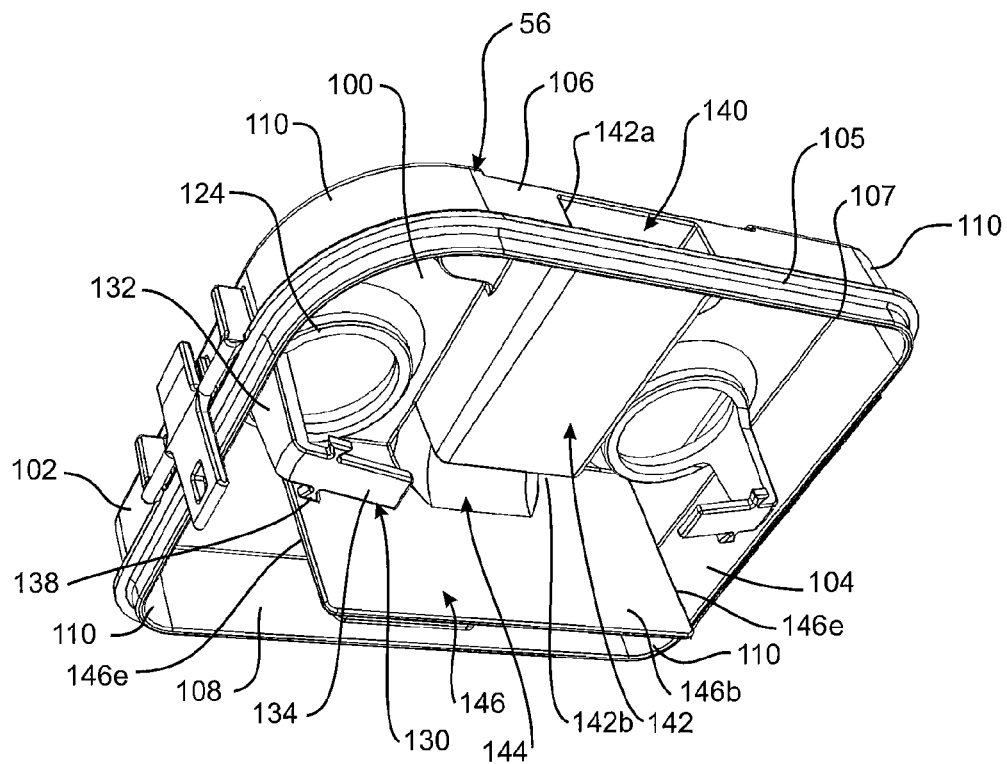
FIG. 18 shows a close-up perspective view of the underside of the lid of the humidification chamber of FIG. 3.

Referring to FIG. 18, the humidification chamber 50 comprises at least one water level indicator which is configured to provide the user with at least an indication as to when the water level is approaching a maximum water level. In this embodiment, a water level indicator 130 is provided for each water fill aperture 120 and is in the form of a tab water level indicator 130 comprising a tab or member that is supported from the lid and which extends down into the interior volume of the humidification chamber, and in particular into the region defined by the water tub 54. In this embodiment, each water level indicator 130 comprises a substantially vertically extending support member 132 which extends downwardly from the underside of the edge 124 of the water fill aperture and terminates with an inwardly extending tab portion or member 134 that extends into the substantially vertical pouring channel region or viewing zone associated with the water fill aperture. In particular, the tab portion 134 is substantially visible when a user looks directly into the centre of the water fill aperture from above, i.e. it is located in the field of view into the interior of the chamber from the water fill aperture. In this embodiment, the angle between the vertical support member 132 and tab portion 134 is obtuse such that tab portion 134 extends with a downward slope from vertically extending support member 132. As shown in FIGS. 4 and 18, each tab portion 130 is provided with a maximum water level indication formation 138. In this embodiment, the maximum water level indicator formations 138 are provided as triangular formations extending outwardly from either side of the tab portion 134, although it will be appreciated that any other form of indicators could be utilised, including printed indicators, markings or indicia, such as printed lines, or otherwise. As the tab portion 134 has a downward slope or tilt relative to the horizontal, the user is provided with warning that they are approaching the maximum water level as they are filling the water tub and as the water level begins to rise into contact with the tab portion 134. However, it will be appreciated that in alternative embodiments, the tab portion 134 may be substantially horizontal such that there is a 90° or right angle between the vertical support member 132, and in such embodiments the user is alerted to filling the water tub to the maximum level as soon as the water contacts the tab. It will be appreciated that the larger the downward slope or tilt on the tab portion 134, the more warning is provided to the user that they are approaching the maximum water level fill volume as they see the water level on the tab progressively approaching the maximum water level indication formation 138.

By way of further explanation, the viewing zone associated with water fill apertures 120 is the visible region into the interior of the chamber that is viewable when the user is located directly above the centre of the water fill aperture. For example, with reference to FIG. 20, the viewing zone can be considered as a virtual cylindrical zone extending downwardly from the edge 124 of the water fill aperture 120 as represented between the arrows BB in the cross-sectional view of FIG. 20 of the humidification chamber. As shown, the tab portion 134 containing the maximum fill level indicator formation 138 is configured to extend into the viewing zone of the water fill aperture 120. This means the water level indicator is directly viewable through the water fill aperture and can be seen by the user simultaneously while filling through the same aperture.

Lid Inlet

The lid 56 is provided with a gases inlet through which a pressurized gases stream generated by the blower of the respiratory device may flow through into the interior of the humidification chamber 50. Referring to FIGS. 3-6, the gases inlet 140 is provided on the inlet side 62 of the humidification chamber 50. As shown in FIG. 6 the gases inlet 140 is provided in a form of an aperture, in this case rectangular but could be any other shape such as circular or otherwise, provided through the inlet side perimeter wall 106 of the lid 56. In this embodiment, the gases inlet 140 is centrally located along the perimeter wall 106, although this position may be varied. Referring to FIG. 18, in this embodiment the inlet aperture 140 is provided with an associated inlet channel or conduit 142 that channels or directs the inlet gases flow stream into a central zone or region of the lid before exiting the conduit 142 into the interior of the humidification chamber. In this embodiment, the inlet conduit 142 extends between a first end 142a located at the inlet aperture of the wall 106 and terminates at a second end 142b located toward a central zone of the lid. The hollow inlet conduit 142 has a cross-sectional shape that corresponds to the shape of the inlet aperture 140 and extends inwardly in a substantially horizontal direction from the vertical perimeter wall 106 of the lid 52. The inlet conduit 142 extends into a central zone of the lid to assist in minimizing or reducing water backflow into the blower and device if the respiratory device is accidently tilted or tipped over from its normal upright operating orientation.

In this embodiment, the gases inlet 140 and inlet conduit 142 is located at or toward the top of the lid. However, in alternative embodiments, the lid may be deeper with taller perimeter walls, and the inlet 140 and conduit 142 may be displaced away from the top of the lid, for example located at or toward the bottom of the lid. Such a configuration provides a volume of space above the inlet in the lid for water to collect during tilting of the chamber, and may reduce the likelihood of water backflow through the inlet.

At the exit of the inlet conduit 142, a flow directing formation 144 is provided for directing the gases stream exiting the inlet conduit. In this embodiment, the flow direction formation 144 is in the form of a curved inverted ramp surface that begins at or towards the main body portion 100 of the lid at the exit end 142b of the inlet conduit 142 and terminates at a first side 146b of a vertical flow panel 146 which extends downwardly from the main body portion 100 of the lid. This configuration causes some of the incoming gases stream to turn back upon itself back toward the inlet walls of the humidification chamber where it is humidified before circulating back around past the side edges 146e of the flow panel 146 toward the outlet of the humidification chamber. The configuration also assists in directing the air flow directly into the surface of the water to increase the absorption of moisture from the water into the incoming gases. The vertical flow plane 146 is displaced from the exit end 142b of the inlet conduit 142.

Figure 20:
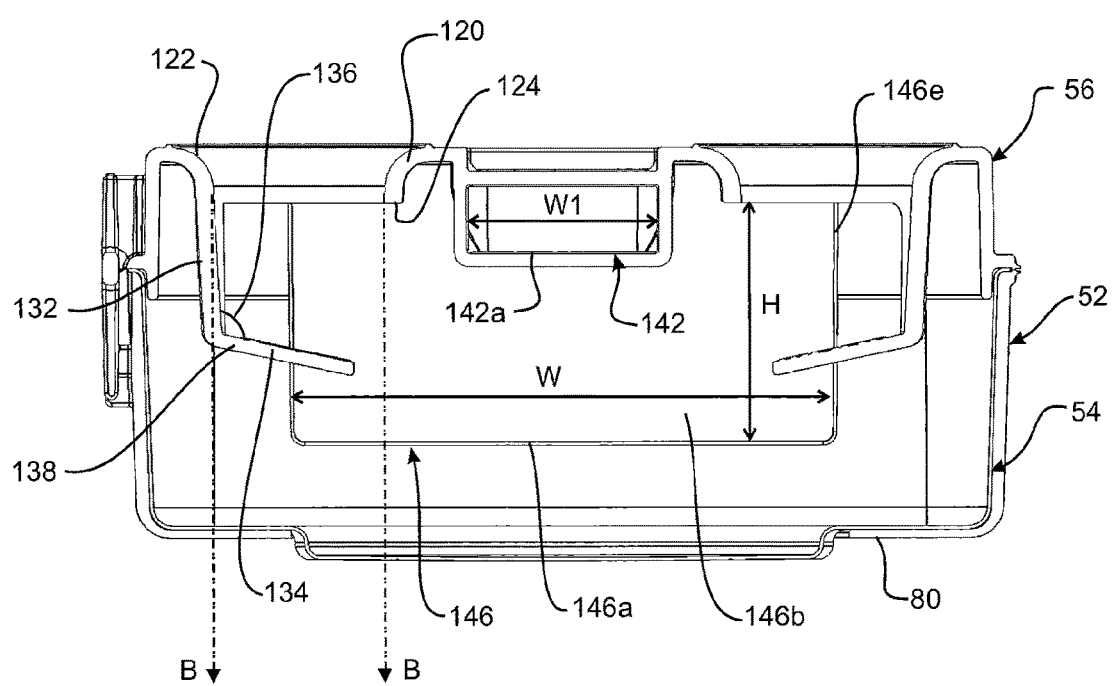
FIG. 20 shows a cross-sectional view of the closed humidification chamber through line CC of FIG. 4.

FIG. 20 shows the first side 146b of the vertical flow panel 146. In this embodiment, the width (W) of the vertical flow panel 146 or baffle is shorter than the overall length of the humidification chamber from the front end 60 to the rear end 58 but preferably wider than the width (W1) of the inlet conduit 142. In this embodiment, the height (H) of the vertical flow panel is such that it's lower edge 146a at least extends below the lower edge 142a of the inlet conduit 142 and typically extends further at least below the horizontal maximum water level line, indicated by the indicator formations 138 of the tab water level indicators. In this embodiment, the lower edge 146a of the vertical flow plane 146a is situated between the maximum water level indicator formation 138 and the lower base surface 80 of the water tub 54, but may in an alternative embodiment extend substantially to the bottom surface 80 of the water tub 54. Preferably, the height of the vertical flow panel 146 is such that its lower edge 146a extends into or through the surface of the volume of water in the water tub 54, for at least water volumes that reach the maximum water level line, and more preferably the lower edge 146a is configured to extend into the surface of the water for at least a portion of water volumes below the maximum water level line, and even more preferably all water volumes (i.e. where the lower edge 146a extends substantially to the base surface of the water tub). Typically, the height of the flow panel is configured such that it protrudes or penetrates sufficiently deeply into the surface of the water to prevent gases exiting the inlet conduit 142 from passing underneath the lower edge 146a and directly to the outlet conduit 152, such that the gases are forced to flow around the flow panel and increasing the path the gases take around the chamber while exposed to the water vapour before exiting the chamber. If the height of the flow panel is too short such that gases can travel under the flow panel directly to the outlet, then this results in a shortened flow path and reduced humidification, and can also result in the gases stream blowing or splashing water into the outlet conduit 152 as the gases stream travels back up from underneath the flow panel.

Lid Outlet

Referring to FIGS. 4 and 7, a gases outlet 150 is provided on the opposite side of the humidification chamber to the gases inlet 140. In this embodiment, the gases outlet 150 is provided on the outlet side perimeter wall 108 of the lid 56 of the humidification chamber and like the gases inlet 140 is centrally located relative to the front and rear ends of the humidification chamber, although this is not essential. The gases outlet 150 comprises an aperture extending through the perimeter wall 108 that is substantially rectangular, although other shaped apertures such as circular or otherwise could alternatively be utilized. Once the gases are heated and humidified in the humidification chamber, the gases stream exits the humidification chamber via gases outlet 150.

Figure 12:
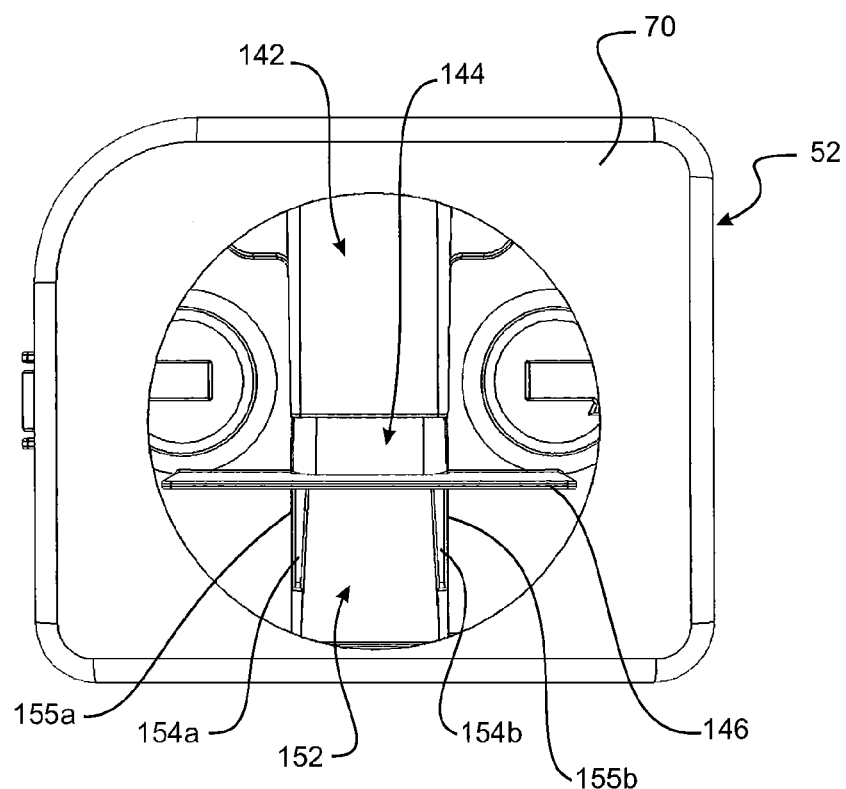
FIG. 12 shows an underside view of the closed humidification chamber of FIG. 3 but with the water tub omitted from view.
Figure 19:
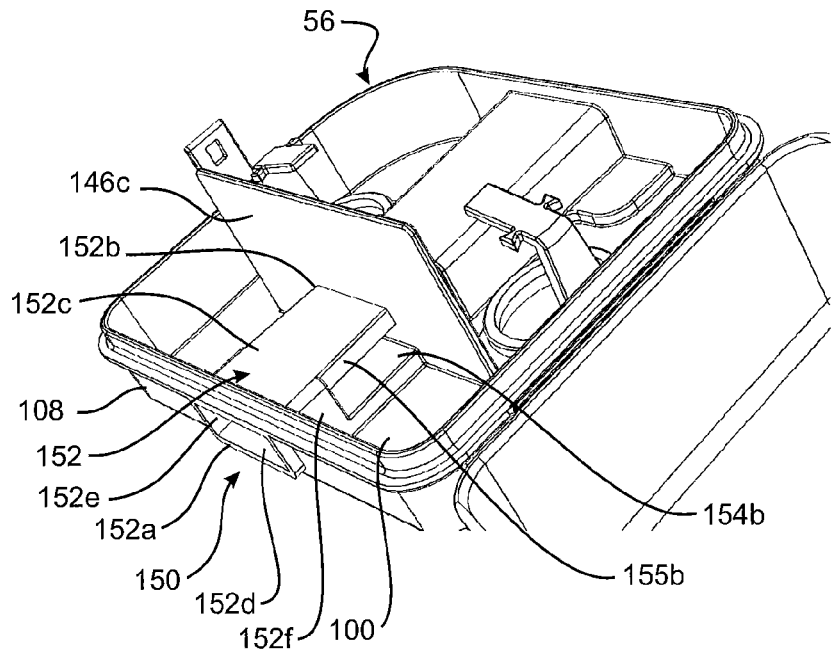
FIG. 19 shows another close-up perspective view of the underside of the lid of the humidification chamber of FIG. 3.

Referring to FIGS. 12 and 19, in this embodiment the gases outlet 150 comprises an outlet conduit 152 that extends into a central zone or region of the lid of the humidification chamber from gases outlet aperture in a horizontal or perpendicular direction relative to the perimeter wall 108. In particular, the outlet conduit 152 extends from a first end 152a located at the aperture of the gas outlet 150 in the wall 108 and extends into the interior of the lid 56 and terminates at second end 152b. In this embodiment, the second end 152b of the outlet conduit 152 abuts or engages with the second side 146c of the vertical flow panel 146. At or toward the second end 152b of the outlet conduit 152 are provided one or more inlet apertures through which gases in the humidification chamber may enter the conduit 152 and may exit the humidification chamber via the gases outlet 150. In this embodiment, the outlet conduit 152 is substantially rectangular having lower 152c and upper 152d walls and left 152e and right 152f side walls which extend along its length. In this embodiment, two main inlet apertures 154a and 154b are provided at or towards the second end 152b of the inlet conduit in each of the side walls 152e and 152f such that inlets open toward either the front or rear ends of the lid. In this embodiment, the inlet apertures 154a, 154b are substantially rectangular, but may be circular or otherwise. As shown in FIGS. 7, 12 and 19 vertical wall formations 155a, 155b extend up from the lower wall 152c of the conduit in the region of each respective inlet aperture 154a, 154b. The wall formations 155a, 155b act as water splash barriers and are configured to force the gases stream to move up around the wall before entering the apertures 154a, 154b rather than moving directly into the apertures from the surface of the water directly underneath the apertures. This configuration reduces the likelihood of water being picked up or carried by the gases stream (particularly at high flow rates) and entering into the outlet conduit 152. It will be appreciated that the inlet conduit 152 need not necessarily extend all the way into contact with the vertical flow panel 146, and may alternatively terminate at a position between the vertical flow panel 146 and side wall 108 of the lid.

Lid Inlet and Outlet Connections

As described above, the gases inlet 140 and the gases outlet 150 have associated conduits 142 and 152 for creating the desired gas flow path within the humidification chamber to maximize humidification, although it will be appreciated that these conduits are not essential. In an alternative embodiment the gases inlet 140 and gases outlet 150 may simply be apertures in the side walls without conduits extending into the interior of the humidification chamber.

When inlet and outlet conduits 142, 152 are provided, it will be appreciated that these need not necessarily enter the chamber lid centrally from opposite sides at a perpendicular angle to the respective perimeter walls. The conduits may be located at corners of the lid and may enter the chamber at any desired angle. Additionally, the conduits need not necessarily be straight conduits, but could be non-straight, and include one or more bends or turns.

As will be appreciated, the gases inlet 140 and gases outlet 150 of the humidification chamber may be connected into the gas flow path of the respiratory device in various ways. It will be appreciated that the gases inlet 140 may be coupled or fluidly connected into the gases flow path by one or more conduits, connectors, and/or gaskets that are coupled to the gases flow path exiting the blower, in a sealed or non-sealed configuration. Likewise, gases outlet 150 may be coupled in any suitable manner, including connectors, conduits and/or gaskets in a sealed or non-sealed configuration to the gas flow path leading to the gases outlet of the respiratory device, which is in turn connected to a patient interface, such as a flexible gases delivery conduit and user interface, as previously discussed.

In this embodiment, as described with reference to FIG. 2 previously, the chamber is retained within a sealable humidification compartment comprising a gases inlet that is fluidly connected to the blower outlet and a gases outlet that is fluidly connected to the main gases outlet of the respiratory device, which is typically coupled or connectable to a patient interface. In this embodiment, the gases inlet 140 of the chamber is not sealingly connected to the inlet of the compartment but rather open to the pressurized gases entering the sealed compartment. Alternatively, a sealed connection between the inlet of the chamber and compartment may be employed. In this embodiment the gases outlet 150 of the chamber is preferably sealingly connected or coupled via a gasket or other sealed connection configuration to the gases outlet of the humidification compartment or at least closely aligned to each other to minimize gas bypassing the chamber directly to the compartment outlet.

Hinge and Clip

As previously mentioned, the lid 56 is hingedly coupled or connected to the cradle 52 such they are moveable between an open position in which lid is pivoted away from the cradle to enable the water tub 54 to be removed from the cradle (or to allow the tub to be filled with water or cleaned with the lid open) and a closed position in which the lid pivots into engagement with the cradle to encapsulate and secure the water tub between the lid and cradle. In this embodiment, the lid 56 is pivotal about a hinge located at the rear end of the chamber between the closed position or configuration as shown in FIG. 3 and the open position or configuration as shown in FIGS. 13-16, for example.

Figure 8:
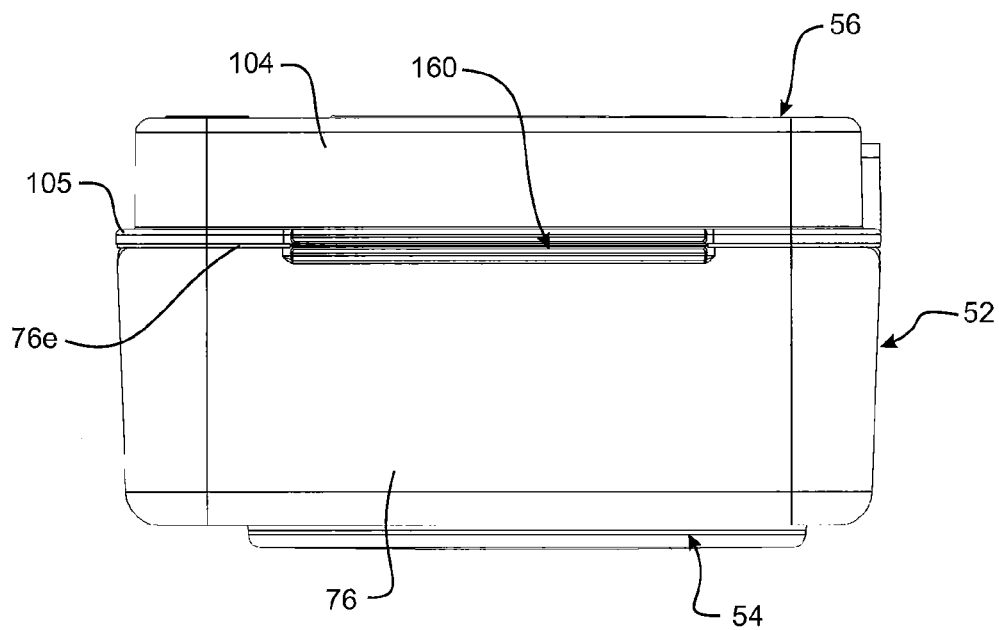
FIG. 8 shows an elevation view of the rear end of the humidification chamber of FIG. 3.
Figure 15:
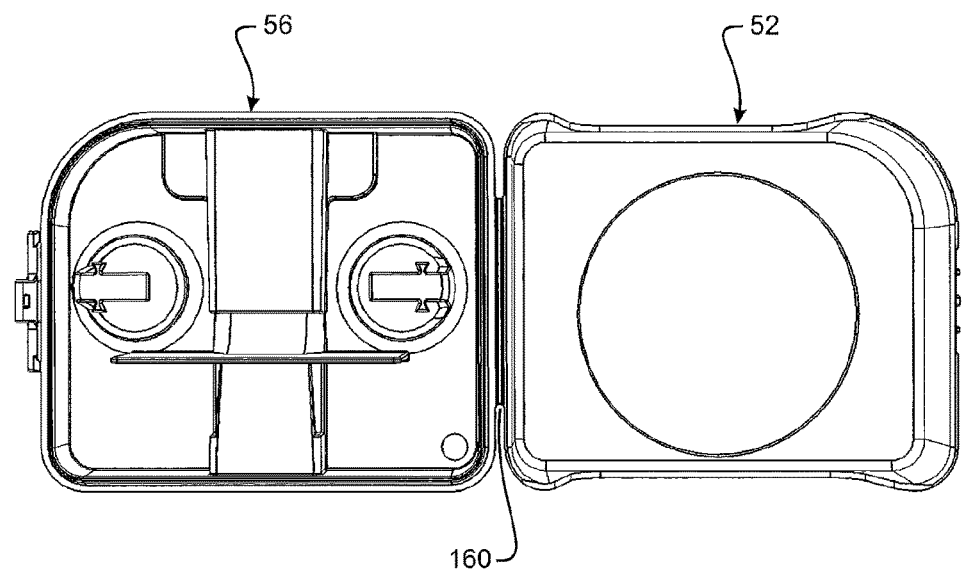
FIG. 15 shows a plan view of the cradle and lid of the humidification chamber of FIG. 3 in an open position.
Figure 16:
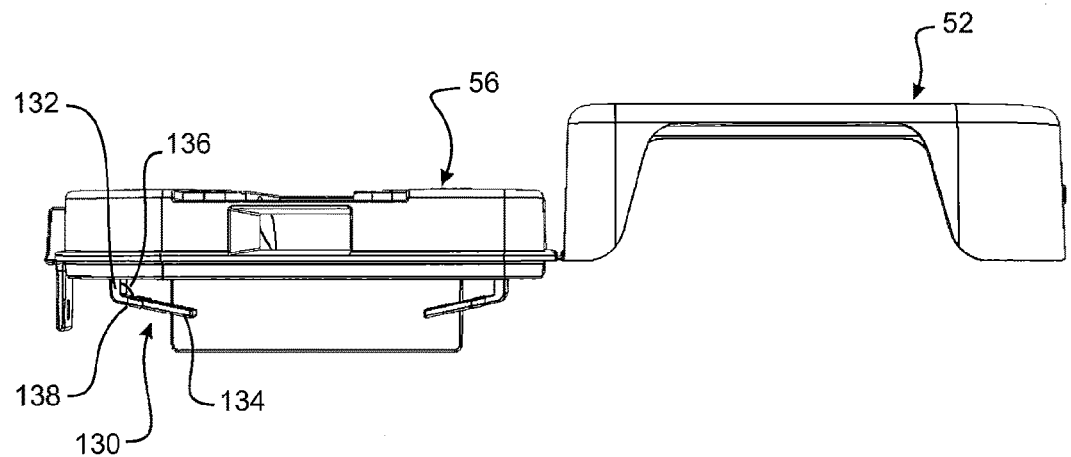
FIG. 16 shows a side elevation view of the cradle and lid of the humidification chamber of FIG. 3 in an open position.

In this embodiment, one or more hinges are located at the rear end of the humidification chamber which are configured to hingedly couple the lid 56 to the cradle 52. Referring to FIGS. 8, 15 and 16, in this embodiment, a single elongate living hinge 160 extends along a portion of the rear end of the humidification chamber between the lid 56 and cradle 54. In particular, the living hinge 160 is a thin flexible plastic hinge that is integrally formed and coupled between a portion of the upper edge 76e of the rear wall 76 of the cradle and a portion of the ledge 105 at the rear end of the lid 56. However, it will be appreciated that two or more hinges may be provided along the rear end of the humidification chamber between the lid and cradle and the hinges need not necessarily be integrally formed living hinges but may be hinges or hinging mechanisms that are formed separately and attached or fixed to the lid and cradle.

To secure the humidification chamber in the closed configuration one or more operable clips or clipping mechanisms are provided and are operable between a latched or locked position for securing the humidification chamber in a closed position, or an unlatched or unlocked position to enable lid 56 to be pivoted away from the cradle into the open position or configuration.

Figure 9:
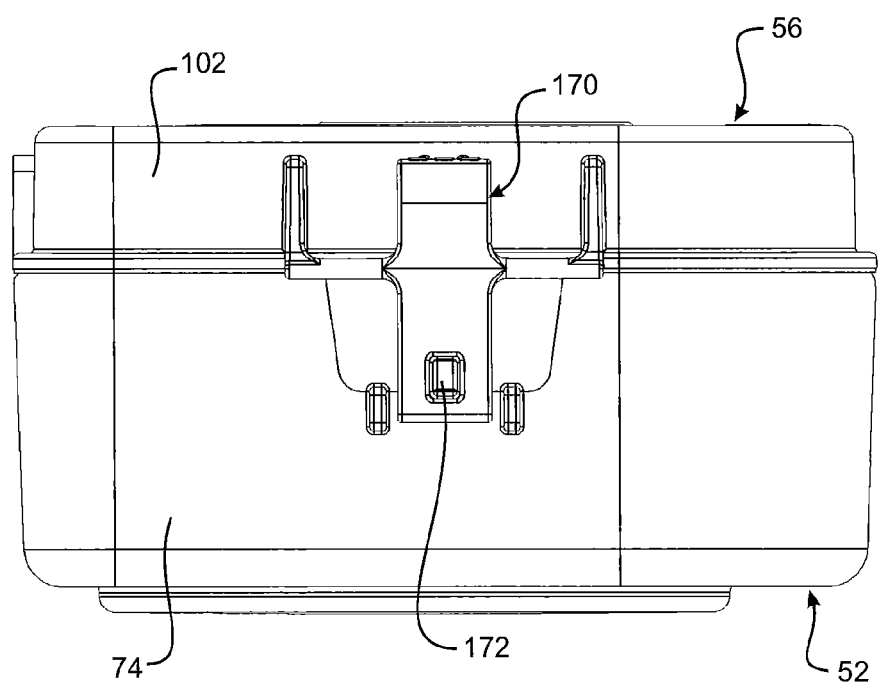
FIG. 9 shows an elevation view of the front end of the humidification chamber of FIG. 3.
Figure 17:
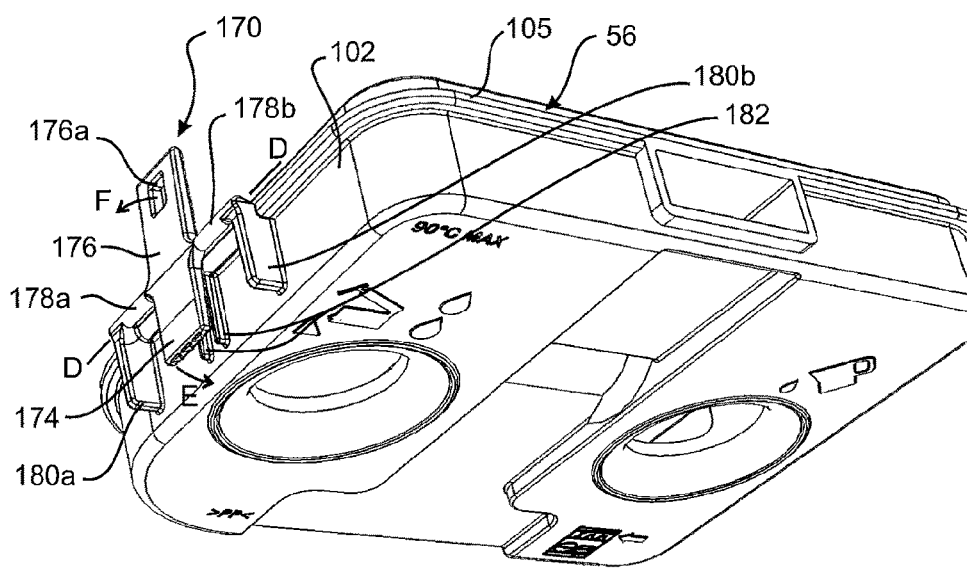
FIG. 17 shows a close-up perspective view of upper side of the lid of the humidification chamber of FIG. 3.

Referring to FIGS. 9 and 17, in this embodiment, a single operable clip 170 is provided or fixed to the lid 56 and which is resiliently moveable between an engaged position and disengaged position with a complimentary catch 172 provided on the cradle 52. In particular, the clip 170 is provided in a central location on the front wall 102 of the lid 56. Referring to FIG. 17, in this embodiment the operable clip 170 is in the form of a torsion clip that is moveable between an engaged and disengaged position relative to the complimentary catch 172 provided on the cradle 52. The clip 170 comprises a user contact portion 174 that may be pressed by a user to move or pivot the clip into a disengaged position and an engagement tab portion 176 which comprises an engagement aperture 176a. In use, the catch 172 is a protrusion or engagement formation that protrudes from the front wall 74 of the cradle and is aligned with the clip such that it engages into engagement aperture 176a of clip 170 when the clip is in a latched or locked position to thereby secure the lid 56 to the cradle 52.

As shown, the clip 170 is mounted to the lid 56 via torsion members 178a, 178b which extend from each side of the clip at an intermediate position between the end of engagement tab portion 176 and user contact portion 174. The torsion members 178a, 178b are longitudinally aligned and define a pivot axis DD about which the clip 170 may pivot or rotate relative to the lid 56 between a rest (engaged, latched) position shown and an unlatched or disengaged position to enable release of the lid from the cradle. As shown, the user contact portion 176 is located adjacent front wall 102 of the lid while the engagement tab portion 176 extends downwardly below the ledge 105 and lower edge of the lid 56. The torsion members 178a, 178b each extend between a respective support strut 180a, 180b provide on the front wall 102 and a side of the clip 170. In this embodiment, the torsion members 178a, 178b are substantially cylindrical (although could have a different cross-sectional shape along their length like square, rectangular or otherwise) and are configured to provide a small degree of twist or flex about their longitudinal axis to thereby enable the clip to pivot or rotate about the pivot axis DD. As shown, the clip 170 is biased into or toward its rest position by the torsion members 178a, 178b.

In use, when the lid 56 is moved from the open position to the closed position the tip of the engagement tab 176 engages a camming surface 172a (see FIG. 14) on the catch 172 which causes the clip to pivot outwardly away from the lid front wall 102 in direction F as shown in FIG. 17. Once the lid 56 is brought into full engagement with the cradle 52, the catch 172 snaps into full engagement with the engagement aperture 176a of the engagement tab portion 176 to thereby allow the clip to return and spring-back into its rest position thereby latching the lid securely to the cradle without the user needing to operate the clip in order to engage it with the aperture. To release the clip mechanism to enable the humidification chamber to be opened, a user simply presses upon the user contacting portion 174 to move it toward the front wall 102 of the lid in direction E as shown. This causes the engagement tab to again rotate in direction F away from the front wall about the pivot axis DD to thereby disengage the engagement aperture 176a from the complimentary catch 172, thereby enabling the lid 56 to be fully pivoted away from the cradle 52 into the open configuration. Once the user releases the pressure on the user contacting portion 174, the clip reverts back to its rest position ready for latching again when the humidification chamber is closed.

Figure 14:
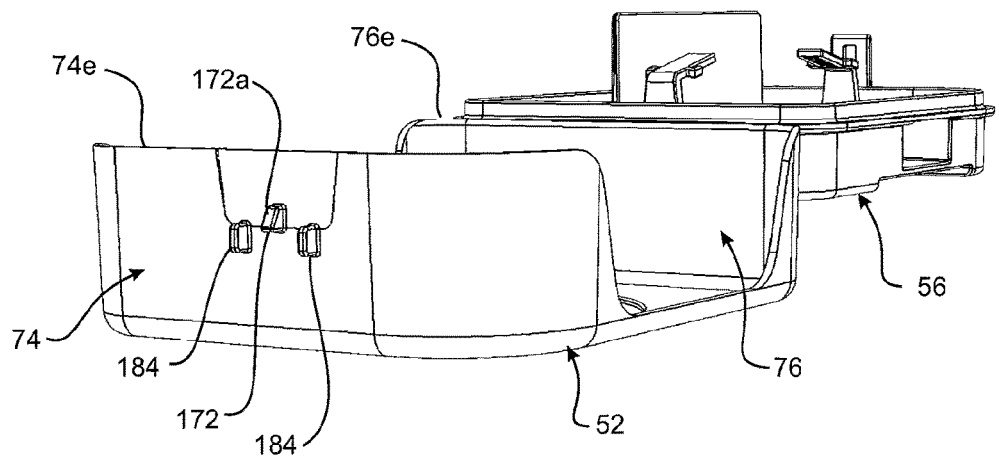
FIG. 14 shows another perspective view of the cradle and lid of the humidification chamber of FIG. 3 in an open position.

As shown in FIG. 17, the front wall 108 of the lid is provided with two limit protrusions 182 on the front wall of the chamber behind the user contacting portion 174, which act to stop the user from over-rotating or twisting the clip to prevent breakage of the clip mechanism. Referring to FIG. 14, guide formations 184 are optionally provided on either side of the catch 172 which protrude from the front wall 74 of the cradle 52. In use, the guide formations 184 are displaced a sufficient distance apart such that the engagement tab portion 176 of the clip may fit between the guide formations 184 when in the engaged position.

The clip 170 is mounted to the lid and the catch 172 to the cradle in the embodiment shown, but it will be appreciated this may be reversed if desired such that the clip may be fixed to the cradle and the catch to the lid.

It will be appreciated that various other alternative clip arrangements or mechanisms may be employed for securing the lid 56 to the cradle 52 of the humidification chamber. Two or more operable clips or latches may be provided around the periphery of the humidification chamber on one or multiple walls as required. Other examples of various clipping mechanisms will be explained with reference to alternative embodiments of the humidification chamber below and it will be appreciated that such clipping mechanisms be employed in this first embodiment of the humidification chamber also.

Sealing

Referring to FIG. 10, in this embodiment there is no flexible seal (e.g. silicone or rubber, or otherwise) provided about the perimeter of the humidification chamber between the lid 56 and water tub 54. The pressure created by the clipping mechanism when the humidification chamber is closed is considered sufficient to reduce or minimize leakage of gases and/or water at the interface between the lid 56 and water tub 54. Also, additional downward pressure may be applied upon the lid 54 when located within the humidification compartment of the respiratory device. For example, the lid of the humidification compartment may be configured to press down or engage with the lid 56 of the humidification chamber to thereby exert downward force on the lid 56 into a more tightly closed configuration. As the chamber is located in a pressurised humidification compartment, the pressure difference between the outside and inside of the chamber is negligible or near zero. This substantially neutral pressure differential results in minimal tendency for a flow of air out of or into the chamber via the interface or perimeter boundary between the lid and water tub, and therefore sealing is typically not required.

Figure 36:
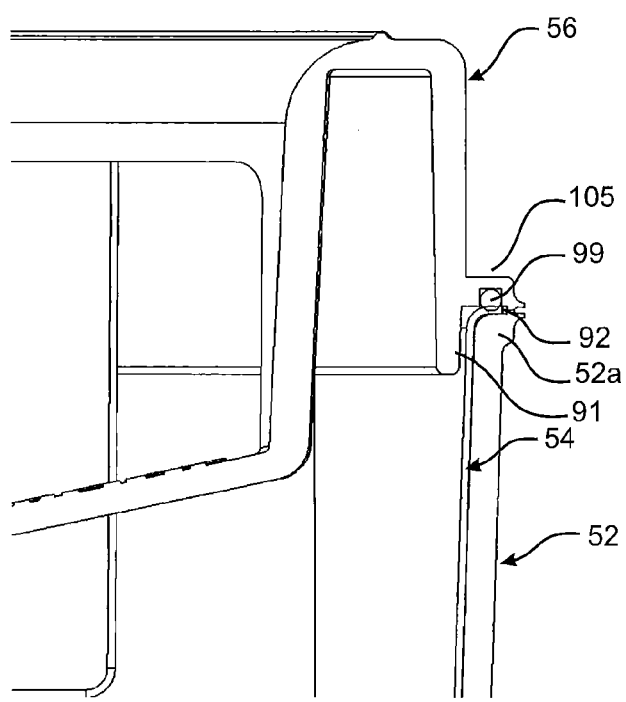
FIG. 36 shows a close-up cross-sectional view of a rear end of a variation of the first embodiment humidification chamber of FIG. 3 that has a seal between the lid and water tub.

However, it will be appreciated in alternative embodiments one or more flexible seals may be provided about the perimeter of the humidification chamber between the lid 56 and water tub 54 to further minimize any possible gas and/or water leakage from the humidification chamber at the interface between the water tub and lid. For example, referring to a perimeter flexible seal may even be mounted to either or both of the rim 92 of the water tub 54 or to the lower edge 107 or ledge 105 of the lid 56. Referring to FIG. 36, one possible sealed chamber configuration is shown in which a perimeter recess or groove is provided on the underside of the ledge 105 of the lid about the entire chamber perimeter and a seal, for example a silicone or rubber o-ring or the like, is mounted or located within the groove for sealingly engaging with the rim 92 of the water tub when the chamber is closed.

Alternative Clipping Mechanisms

As mentioned, various alternative clipping mechanisms may be utilized for securing the lid 56 to the cradle 52 of the humidification chamber 50. Some alternative types of clipping mechanisms will now be explained by way of example only, although it will be appreciated that these examples are not intended to be limiting.

First Alternative Clip Mechanism

Figure 21A:
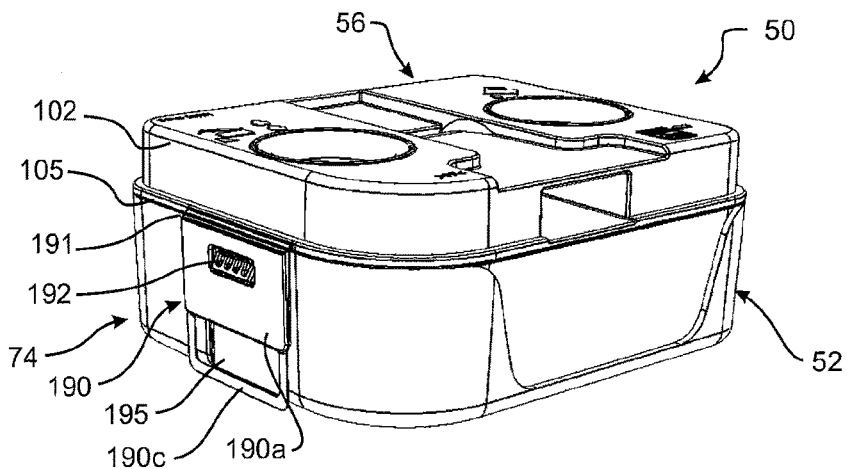
FIG. 21A shows a perspective view of the first embodiment humidification chamber but with a first alternative form of clipping mechanism and with the humidification chamber closed.
Figure 21B:
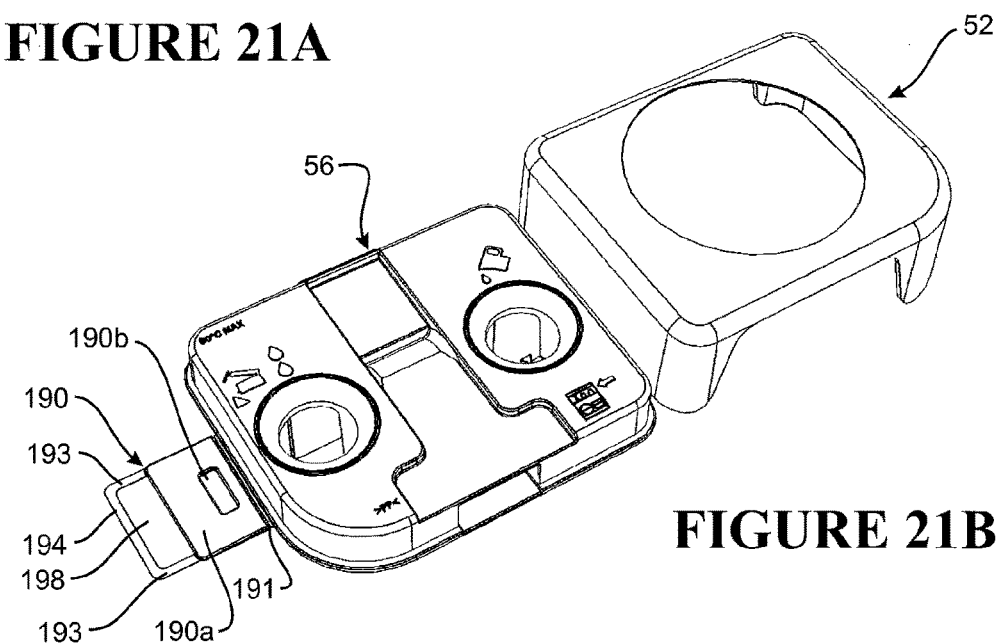
FIG. 21B shows the humidification chamber of FIG. 21A in an open position and with the water tub removed.
Figure 21C:
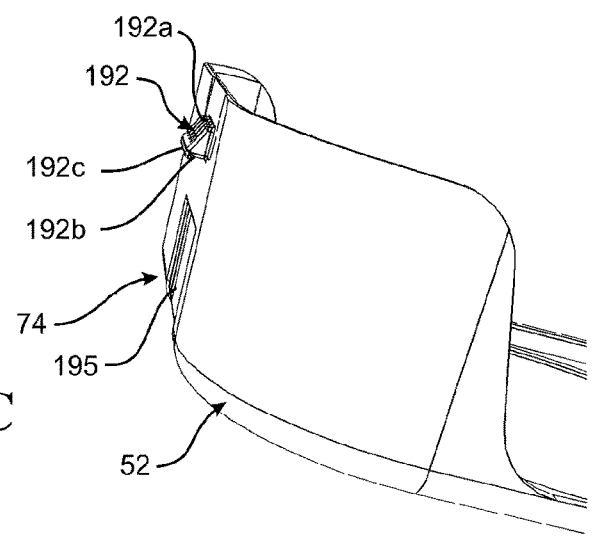
FIG. 21C shows a close-up perspective view of the rear end of the cradle of the humidification chamber of FIG. 21A and the catch formation of the clipping mechanism.

Referring to FIGS. 21A-21C, the first alternative clipping mechanism comprises a clip 190 that is pivotally coupled at the front end wall of the lid 56 via a living hinge indicated at 191. As shown, the clip 190 is hingedly coupled to the ledge 105 of the lid 56. In this embodiment, the clip 190 comprises a main planar tab portion 190a which comprises a central engagement aperture 190b which is configured to engage with a complimentary shaped catch or protruding formation 192 provided on the front wall of the cradle 52. The clip 190 further comprises a downwardly extending handle or grip portion 190c. In this embodiment, the finger handle 190c is in the form of a thin plastic flexible U-shaped member that extends from the lower edge of the main tab portion 190a. In particular, the handle comprises first and second legs 193 that extend downwardly from opposite sides of the lower edge of the main tab portion 190a and which are joined by a cross member 194, and which provides a gripping aperture 198. The finger handle portion 190c may be integrally formed in one piece with the main tab portion 190a of the clip or alternatively formed separately and attached or secured to the clip.

As shown, the finger handle portion preferably is thinner than the corresponding main tab portion 190a such that it is bendable or flexible. In this embodiment, the finger handle 190c extends substantially toward or to the bottom surface of the cradle 52 to provide for easier user finger access or gripping. This configuration also allows the user to extend more of their finger/or more than one finger into the gripping aperture 198 and to use the strength of their arm to pull the clip open rather than levering with the tip of the finger and applying most of the load through the first finger joint. Additionally, as shown in FIG. 21C, the front wall of the cradle 52 may be provided with a recessed portion 195 which is aligned with the handle 190c which enables a user finger access to grip the handle 190c. In this embodiment, the catch formation 192 comprises an elongate formation having a triangular cross-section. In particular, a front downwardly angled front camming surface 192a extends from the front wall 74 of the cradle and a substantially horizontal engagement surface 192b is provided on the underside of the formation. The front edge of the engagement surface 192b is also provided with a ridge or protruding lip that extends downwardly and which assists in retaining the clip in an engaged state with the catch formation 192.

In use, the user may push or pivot the clip 190 about its living hinge into engagement with the catch formation 192 and into a latched position as shown in FIG. 21A. To release the clipping mechanism, the user applies force through a finger or fingers to the handle portion 190c of the clip (or the main tab portion 190a itself if they prefer) in a direction away from the cradle front wall so as to pull the clip free of the engagement formation 192 to thereby release the clip and thereby the lid 56 from the cradle 52.

Second Alternative Clip Mechanism

Figure 22A:
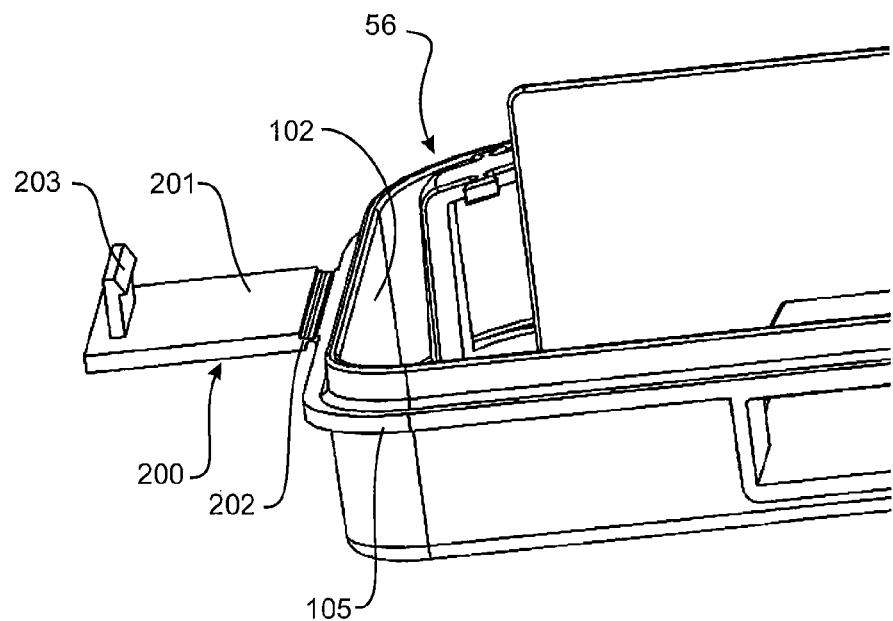
FIG. 22A shows the lid of the first embodiment humidification chamber with a second alternative type form of clipping mechanism.

Referring to FIG. 22A, a second alternative clip 200 is shown. The clip 200 comprises a main tab portion 201 that is integrally coupled via a living hinge 202 to the ledge 105 of the front wall 102 of the lid 56 as with the first alternative clip 190. As before, the living hinge 202 is formed from a portion of plastic having reduced thickness and is flexible such that it enables the clip 200 to pivot relative to the lid 56. In contrast to the engagement aperture 190b of the first alternative clip 190, a second alternative clip 200 is provided and protruding engagement formation 203 that is configured to engage with the complimentary catch formation or aperture provided in the front wall of the cradle (not shown).

Third Alternative Clip Mechanism

Figure 22B:
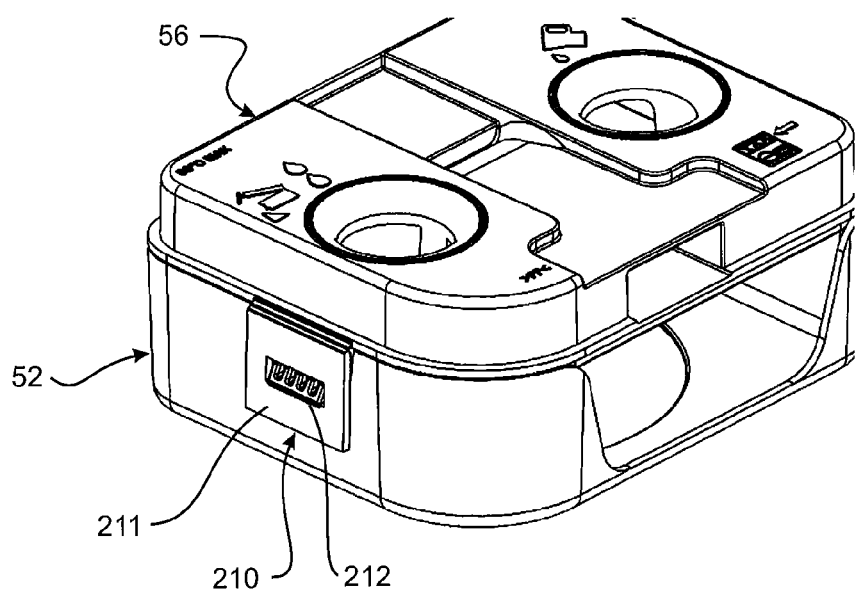
FIG. 22B shows the cradle and lid of the first embodiment humidification chamber with a third alternative type form of clipping mechanism.

Referring to FIG. 22B, a third alternative type of clipping mechanism is shown. The third alternative type clip 210 is similar to the first alternative clip 190 and comprises the hingedly mounted tab 211 having an engagement aperture which is configured to engage with a catch formation 212 provided on the front wall of the cradle. No extension handle is provided in the tab 211 in this embodiment.

Fourth Alternative Clip Mechanism

Figure 23A:
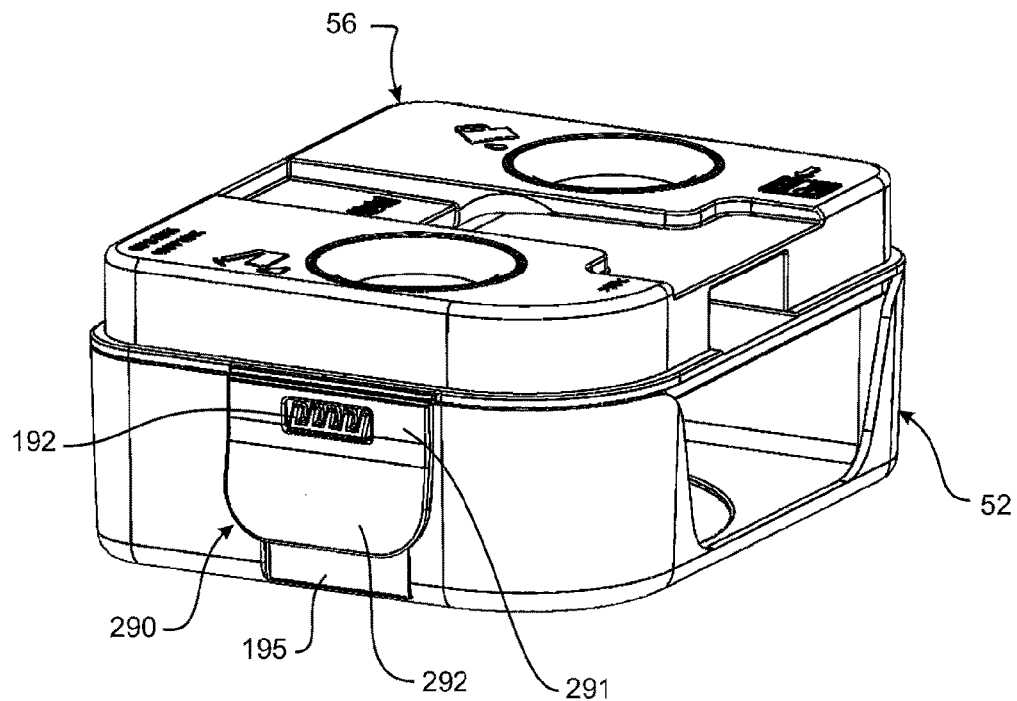
FIG. 23A shows a perspective view of the first embodiment humidification chamber but with a fourth alternative form of clipping mechanism and with the humidification chamber closed.
Figure 23B:
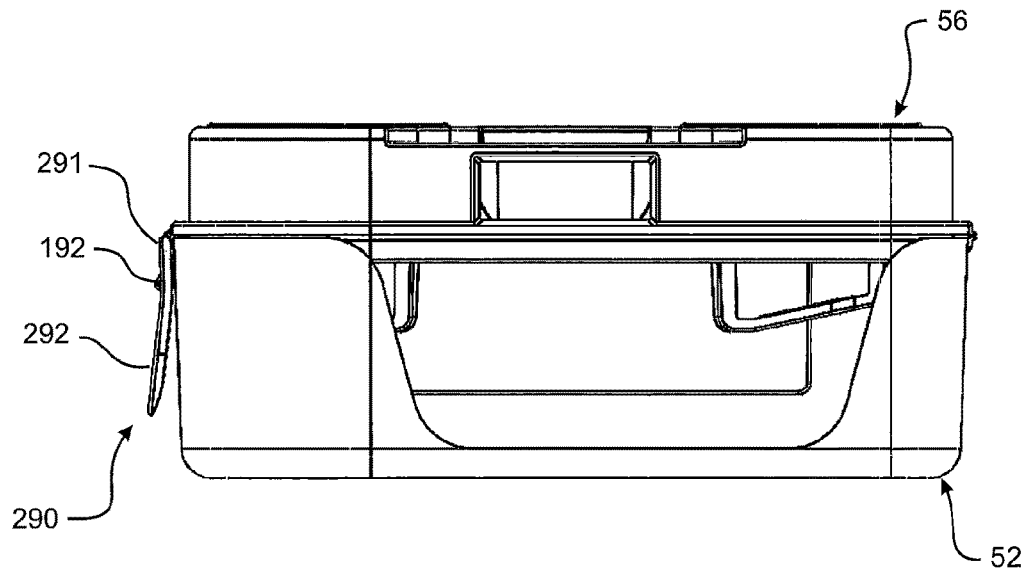
FIG. 23B shows a side elevation view of the humidification chamber of FIG. 23A.

Referring to FIGS. 23A and 23B, a fourth alternative type of clipping mechanism is shown. The fourth alternative type clip 290 is similar to the first alternative clip 190 and like reference numerals represent like features. The clip 290 comprises a hingedly mounted tab which does not have an extension handle. Rather, the tab has a first upper vertically oriented portion 291 that is hingedly coupled to the lid and a lower larger angled portion 292 that extends at an angle away from the upper portion. The upper portion 291 provides the engagement aperture for engaging with the catch formation 192 on the front wall of the cradle as previously described. In the engaged position shown, the lower angled portion 292 of the tab is angled outwardly or away from the wall of the cradle 52 such that a gripping recess or access cavity is formed between the lower angled portion 291 and recessed portion 195 on the front wall to enable a user to grip and pull the tab to disengage the clip when desired.

Alternative Water Level Indicators

It will be appreciated that various other water level indicators to assist the user in identifying when they have filled the water tub to the maximum water level line could be used, some non-limiting examples of which will now be explained by way of example.

First Alternative Water Level Indicator

Figure 24A:
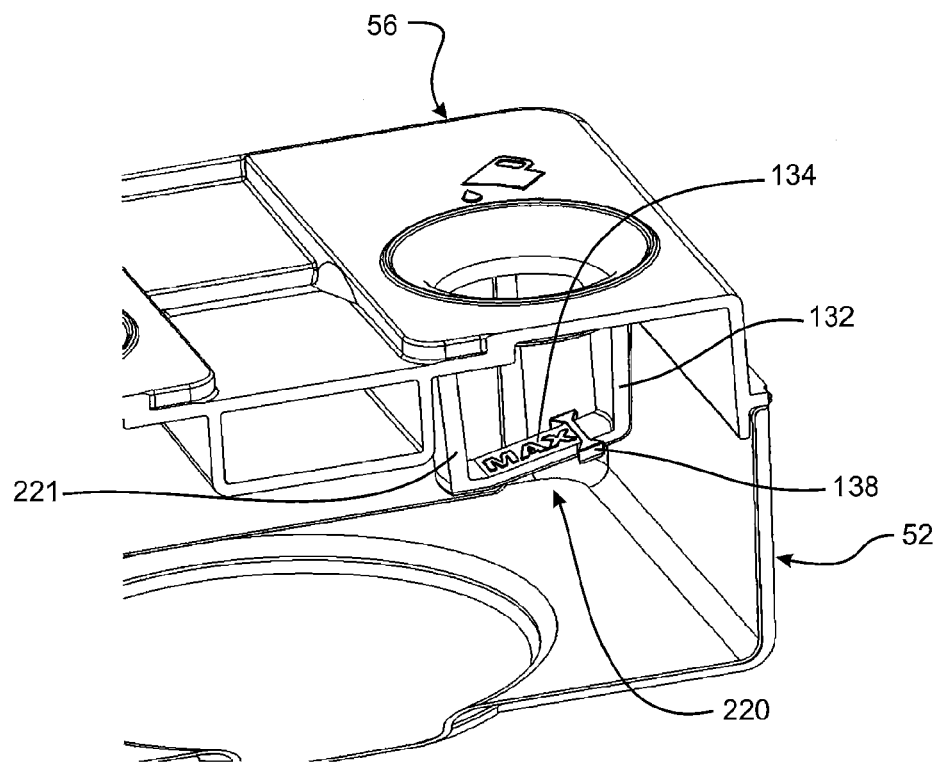
FIG. 24A shows a cross-sectional view of the first embodiment humidification chamber with an first alternative water level indicator in the form of a variant of the tab water level indicator.
Figure 24B:
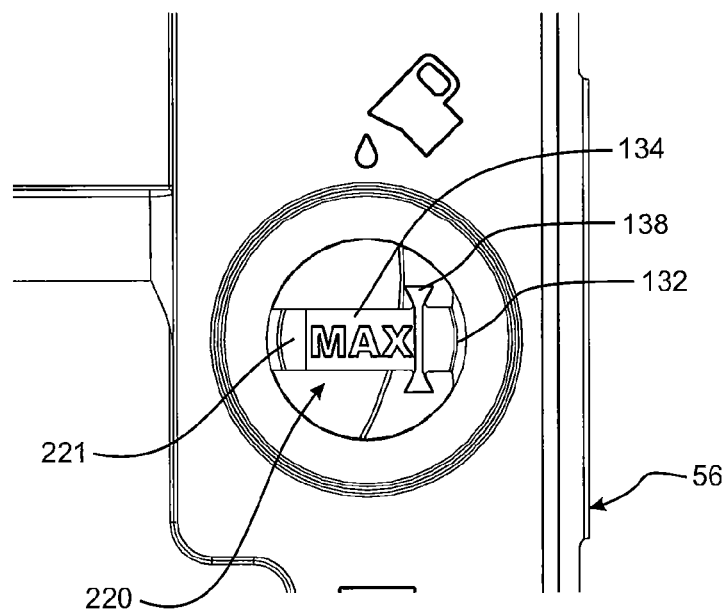
FIG. 24B shows a plan view through the water fill aperture of the lid of the humidification chamber of FIG. 24A and showing the alternative form of tab water level indicator.

Referring to FIGS. 24A and 24B, a first alternative water level indicator 220 is shown and which is a variant of the tab water level indicator 130 previously described. Like reference numerals refer to like components and features. In this variant, an additional vertical support strut or member 221 extends downwardly from the underside of the lid 56 and joins the terminating end of the tab 134 to strengthen the water level indicator and the angle of the tab.

Second Alternative Water Level Indicator

Figure 25:
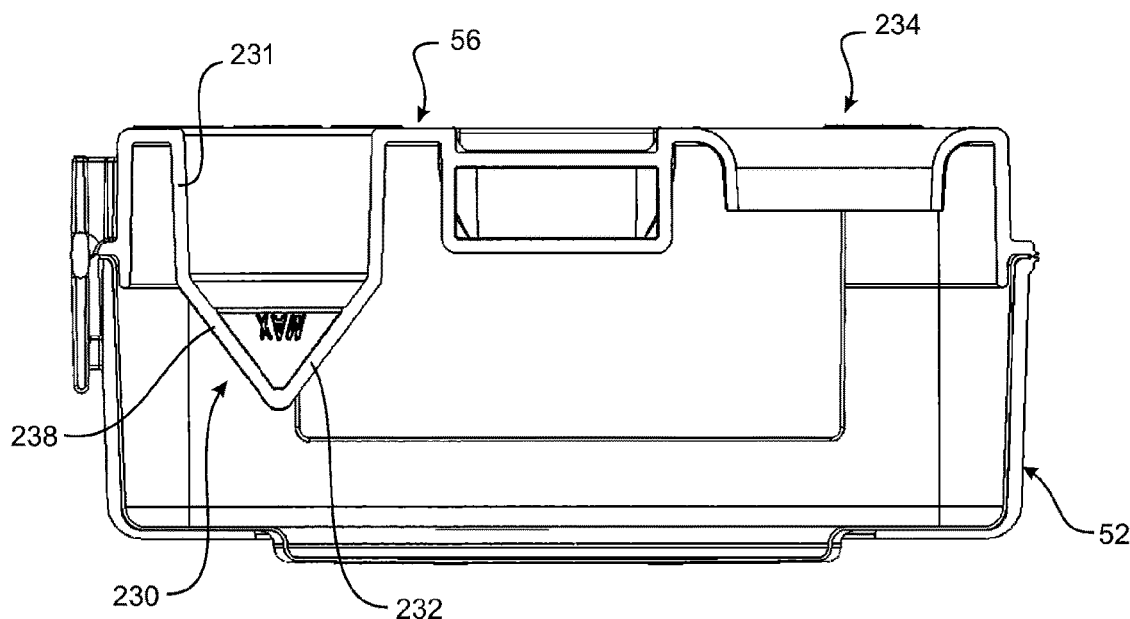
FIG. 25 shows a cross-sectional view of the first embodiment humidification chamber with a second alternative type of water level indicator in the form of a conical water level indicator.
Figure 26:
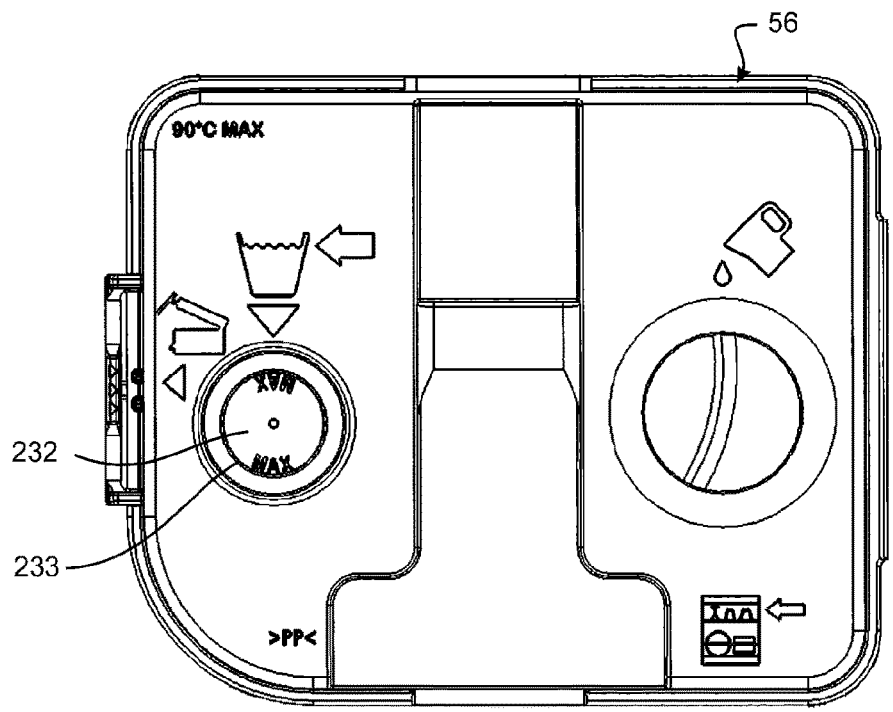
FIG. 26 shows a plan view of the lid of the humidification chamber of FIG. 25 and showing the user's view of the conical water level indicator.

Referring to FIGS. 25 and 26, a second alternative of water level indicator 230 is shown. The water level indicator 230 is a conical water level indicator that comprises a hollow cylindrical formation 231 extending downwardly from the upper main portion of the lid and which terminates in a conical end portion 232 comprising indicators or indicia indicative of at least a maximum water level line as generally indicated at 233. The water level indicator is formed from transparent material, such as transparent plastic. The steepness of the cone portion 232 may be varied to alter the amount of warning the user gets as they approach the maximum water level line. The steeper the angle the more warning is provided, relative to a shallower cone in which less warning is provided. In this embodiment, the lid 56 is provided with a single water fill aperture generally indicated at 234.

Third Alternative Water Level Indicator

Additionally or alternatively, in other embodiments a water level indicator line or lines may be provided on the inner surface of the perimeter walls of the water tub, for example by printing of the lines onto the surface or otherwise pressing or forming the lines into the wall inner surface of the water tub. Such water level indicator lines can be viewed with the lid open such that water can be poured directly into the water tub up to the maximum water fill line on the tub. In such embodiments, separate water fill holes in the lid could be omitted.

Various other humidification chamber embodiments will now be explained, and like reference numerals represent the same or equivalent components or features. It will be appreciated that the features and components of the various embodiments may be interchanged and/or combined to produce further variant embodiments.

Second Embodiment Humidification Chamber—with Full Cradle

Figure 27A:
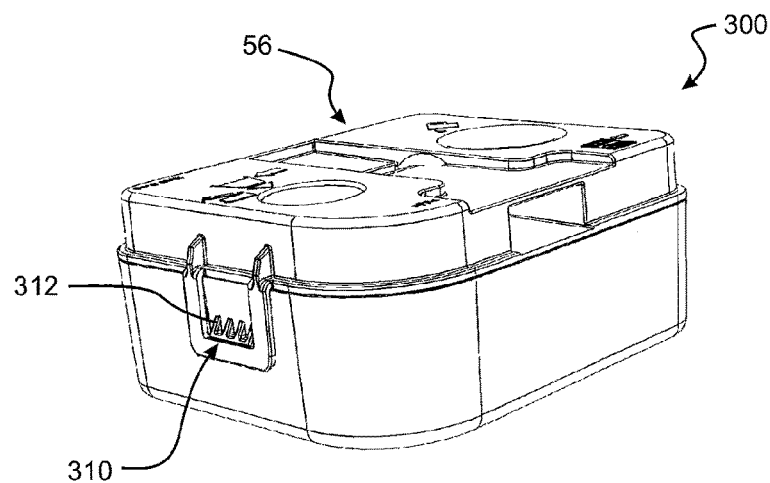
FIG. 27A shows a perspective view of a closed humidification chamber in accordance with a second embodiment of the invention comprising a lid, full cradle and water tub.
Figure 27B:
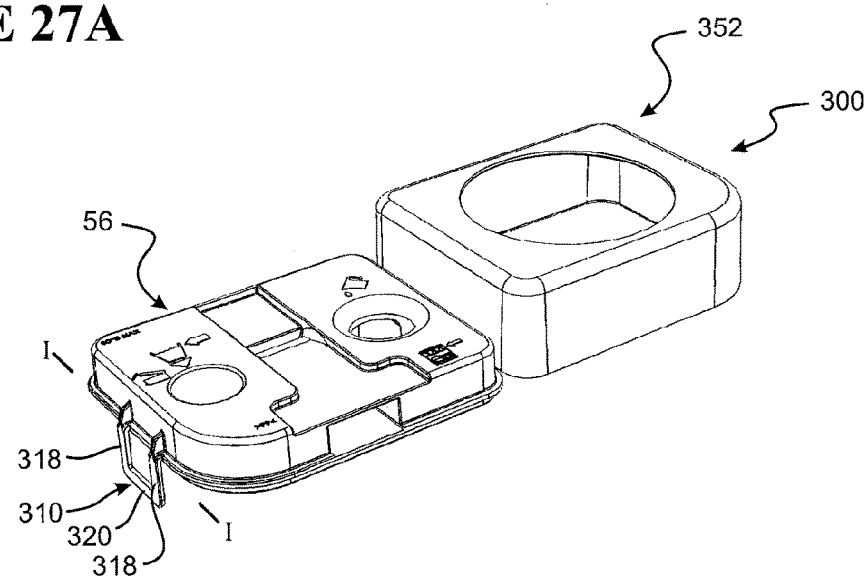
FIG. 27B shows the lid and cradle of the second embodiment humidification chamber lid and full cradle in an open position with water tub omitted.
Figure 27C:
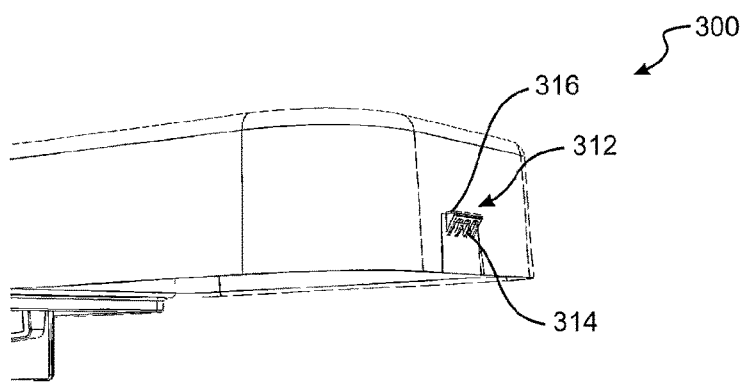
FIG. 27C shows a perspective view of the front end of the full cradle and the catch of the clipping mechanism of the second embodiment humidification chamber.

Referring to FIG. 27A-27C, a second embodiment of the humidification chamber 300 will be explained. The humidification chamber 300 is substantially similar to the first embodiment. As shown, the lid 56 is substantially similar to the first embodiment although it comprises a different clip mechanism 310 on the front wall. In this embodiment, the clip 310 is a U-shaped member mounted to the front wall and which has a degree of flex about the axis indicated at II on FIG. 27B. As shown on FIG. 27A, the clip 310 engages securely with a catch formation 312. Referring to FIG. 27C, the catch formation comprises an elongate formation having a substantially triangular cross-section. In particular, an angled front camming surface 314 extends downwardly and outwardly from the front wall and a substantially horizontal engagement surface 316 returns back to the front wall from the lower edge of the front camming surface 314. The U-shape clip 310 comprises two vertical legs 318 which extend downwardly from the lid and are joined by a cross-member 320. In use the cross-member 320 engages with the camming surface 314 of the catch formation 312 as the lid is brought into engagement with the cradle 352 until snapping or locking into full engagement with engagement surface 316.

As to other aspects, the second embodiment humidification chamber 300 is substantially similar to the first embodiment, and comprises a plastic lid 56 that is hingedly coupled with a plastic cradle 352 which receives a metal water tub of the type previously described. The primary difference of the second embodiment humidification chamber 300 is that the cradle is substantially continuous about the peripheral wall of the water tub such that it substantially encapsulates and surrounds the entire water tub peripheral wall surface.

Third Embodiment Humidification Chamber—with Overmolded Heater Plate

Overview

Figure 28A:
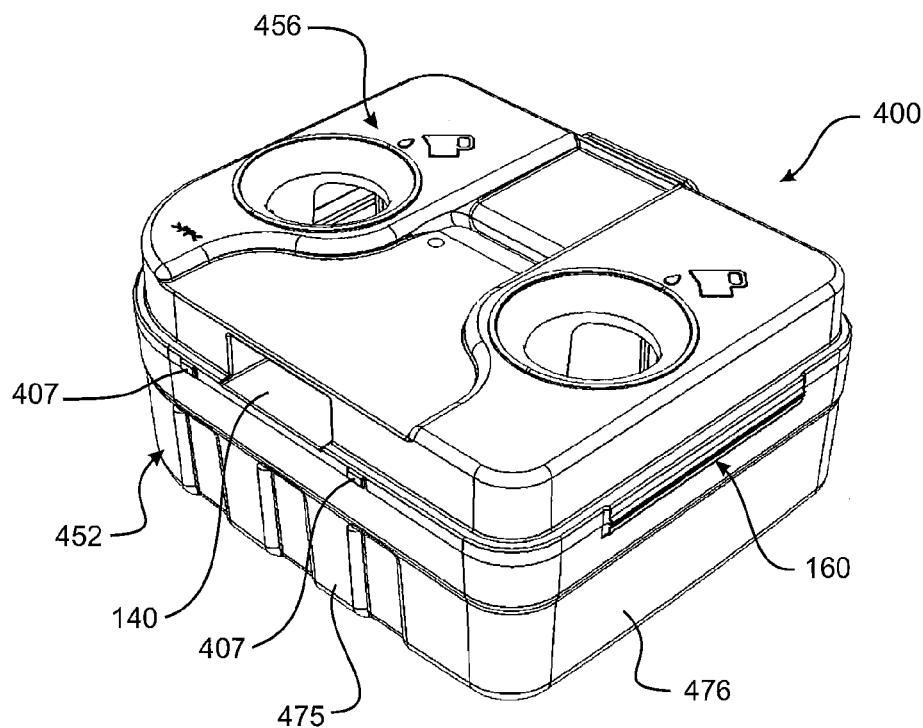
FIG. 28A shows a first upper perspective view of a humidification chamber, in a closed position, in accordance with a third embodiment of the invention comprising a lid and water tub with an overmolded heater plate, and which shows the rear end and gases inlet side of the humidifier chamber.
Figure 28B:
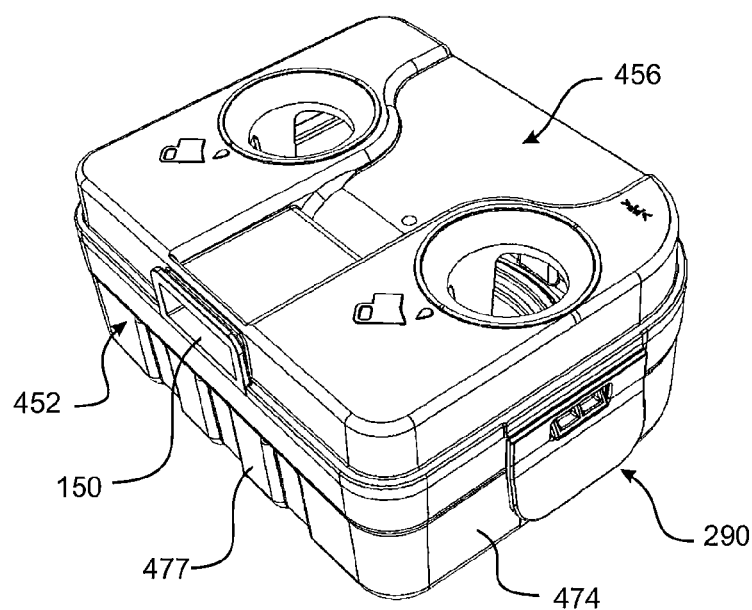
FIG. 28B shows a second upper perspective view of the third embodiment humidification chamber of FIG. 28A, and showing the front end and gases outlet side of the humidification chamber.
Figure 28C:
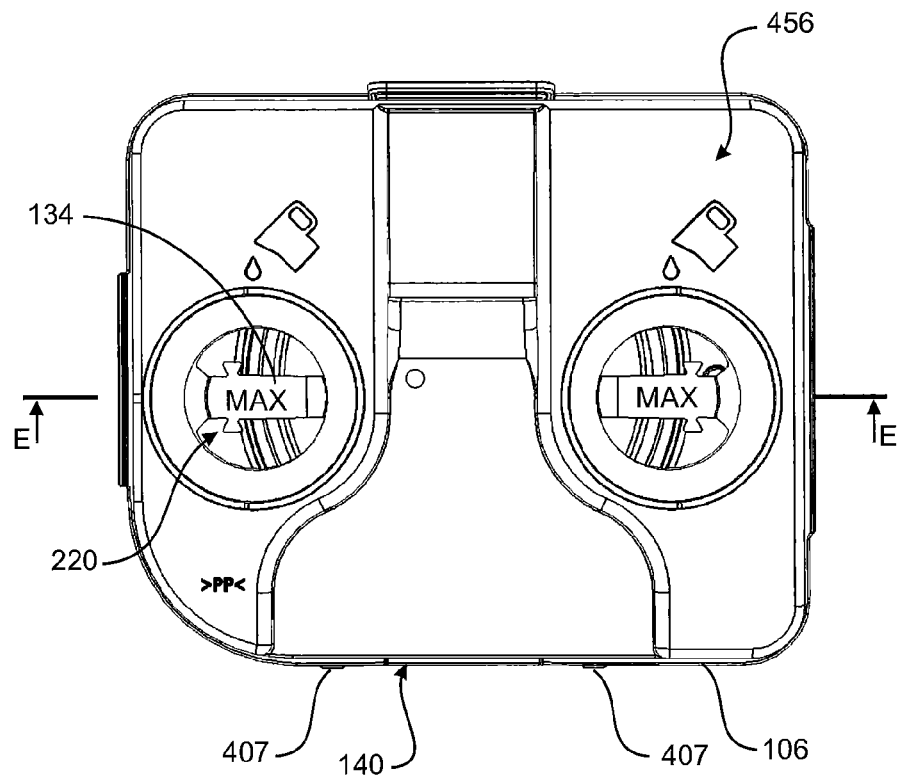
FIG. 28C shows a plan view of the third embodiment humidification chamber of FIG. 28A.
Figure 28D:
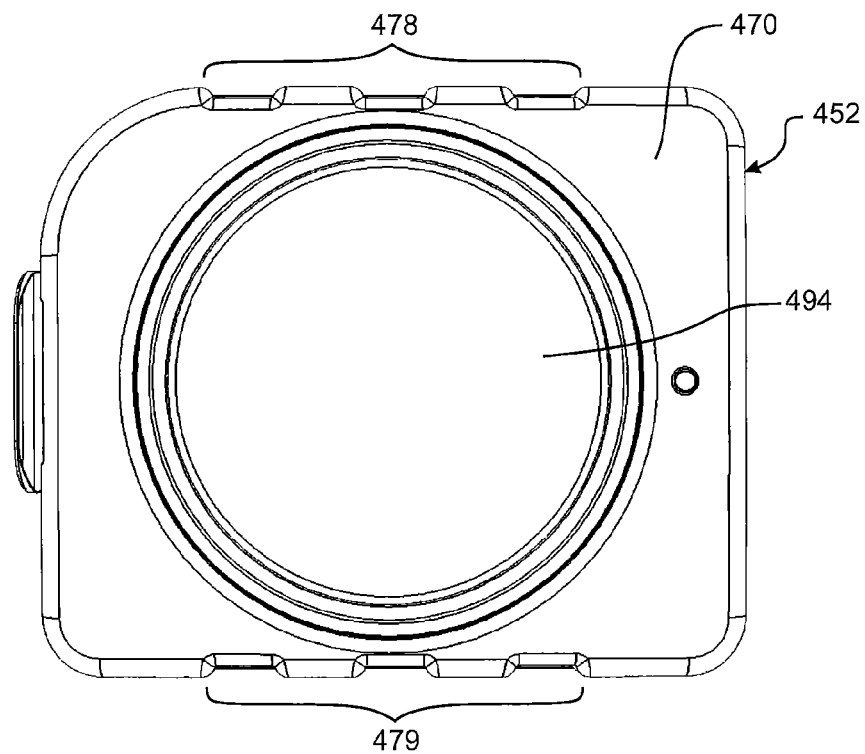
FIG. 28D shows an underside view of the third embodiment humidification chamber of FIG. 28A.
Figure 28E:
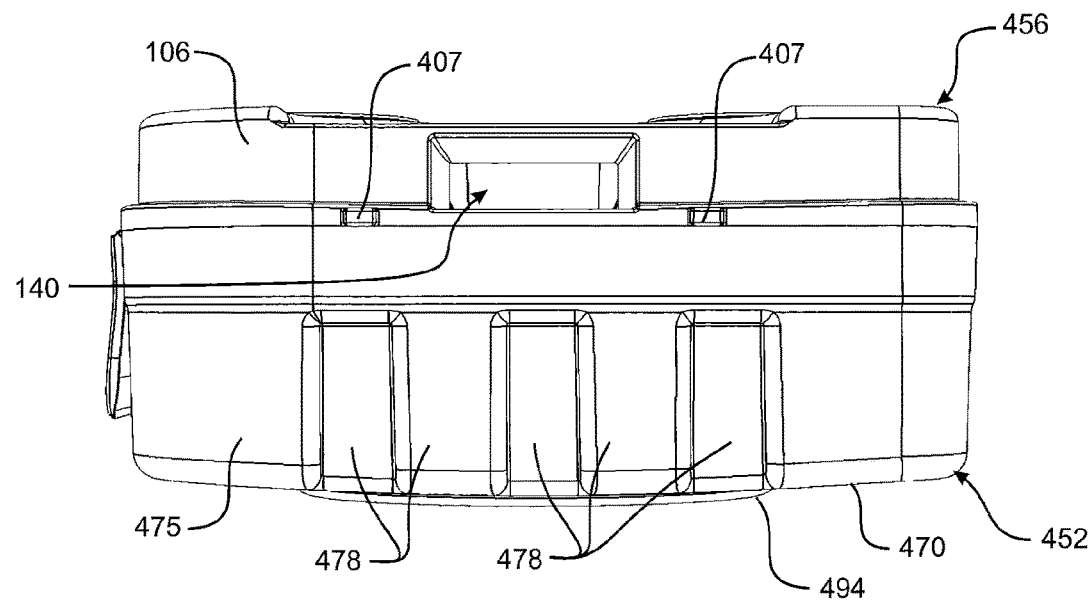
FIG. 28E shows a side elevation view of the gases inlet side of the third embodiment humidification chamber of FIG. 28A.
Figure 28F:
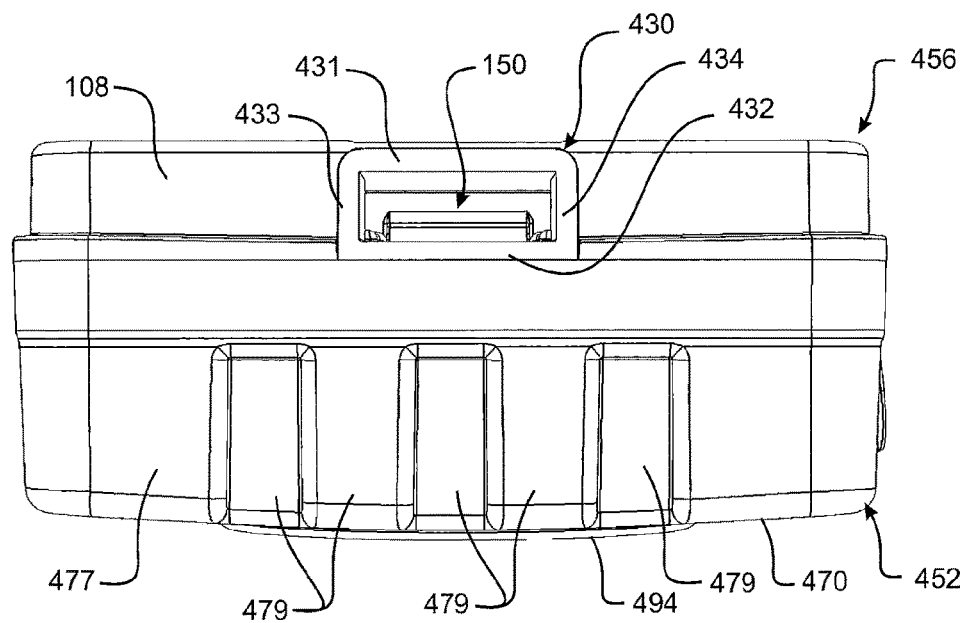
FIG. 28F shows a side elevation view of the gases outlet side of the third embodiment humidification chamber of FIG. 28A.
Figure 28G:
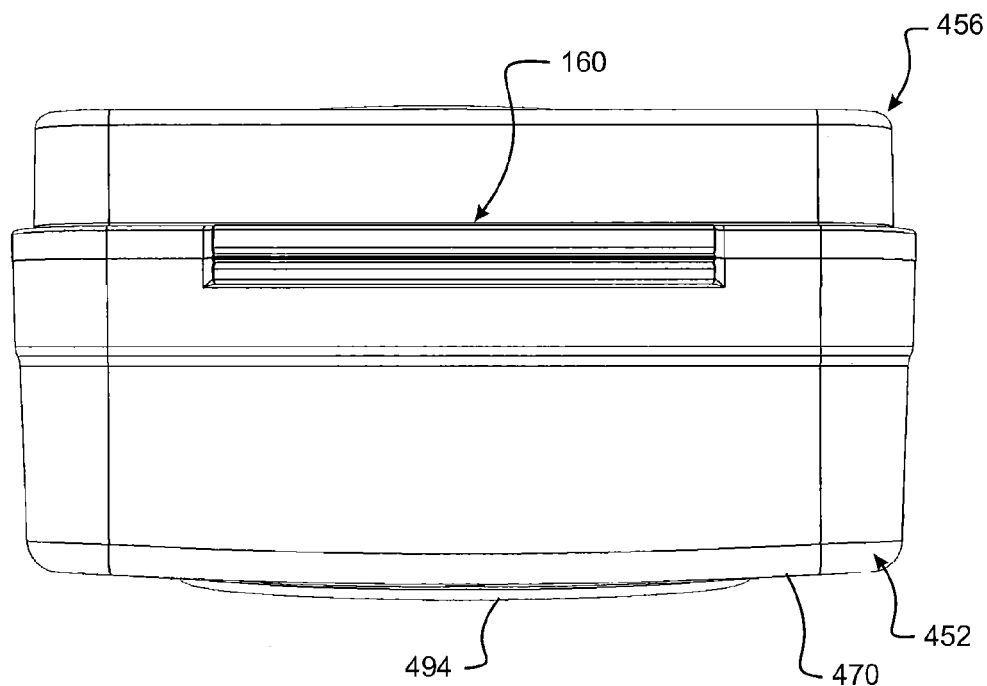
FIG. 28G shows an elevation view of the rear end of the third embodiment humidification chamber of FIG. 28A.
Figure 28H:
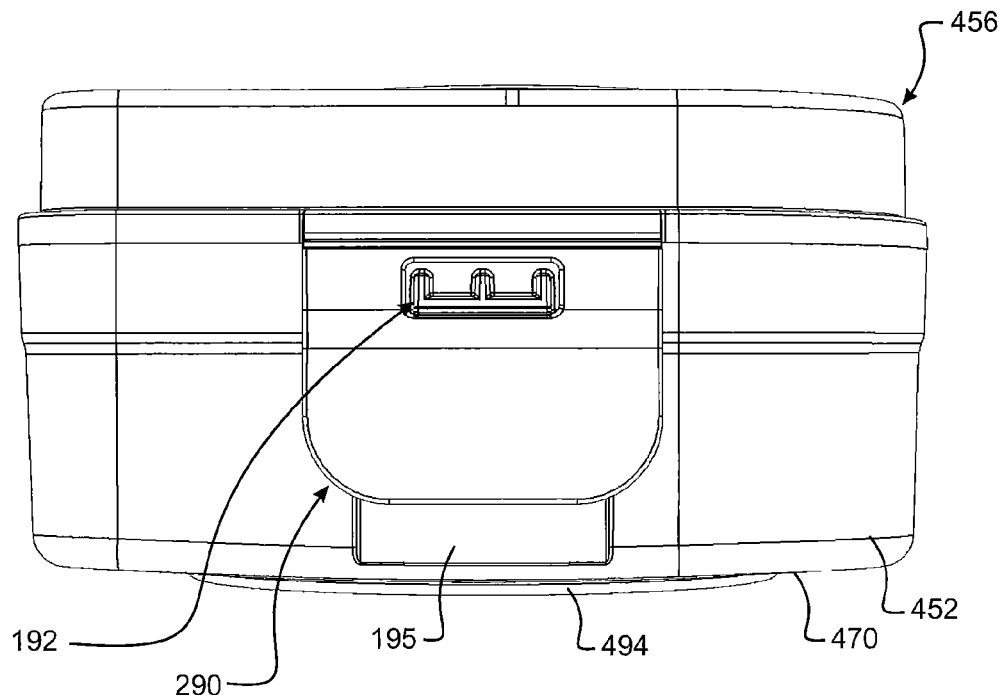
FIG. 28H shows an elevation view of the front end of the third embodiment humidification chamber of FIG. 28A.
Figure 28I:
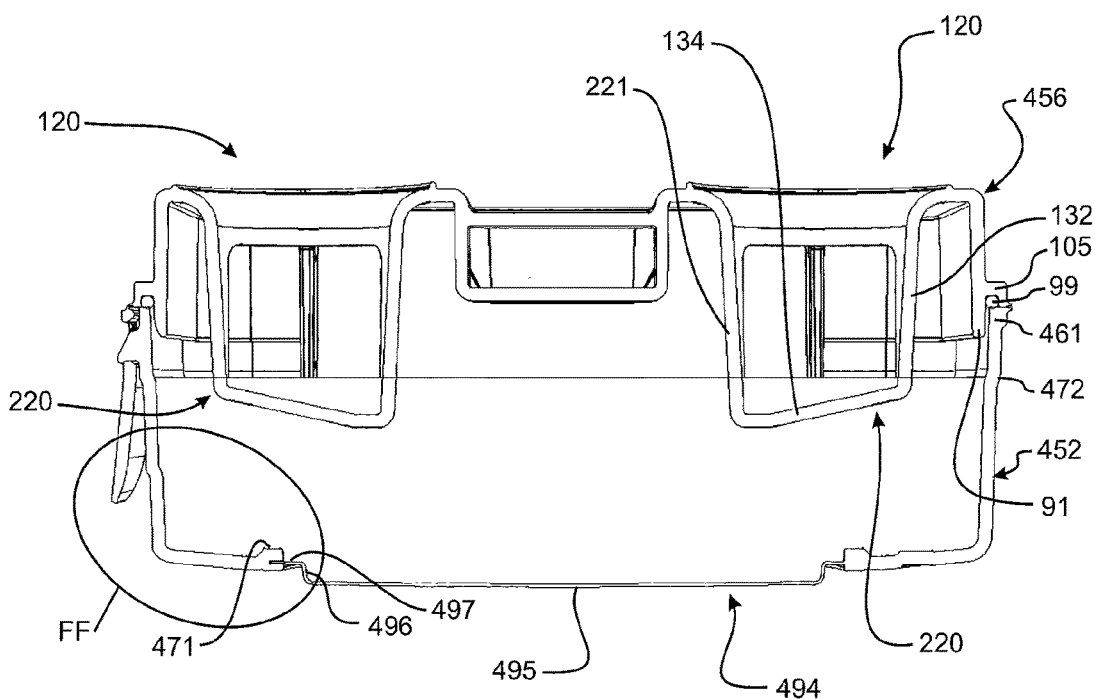
FIG. 28I shows a cross-sectional view of the third embodiment humidification chamber through line EE of FIG. 28C.
Figure 28J:
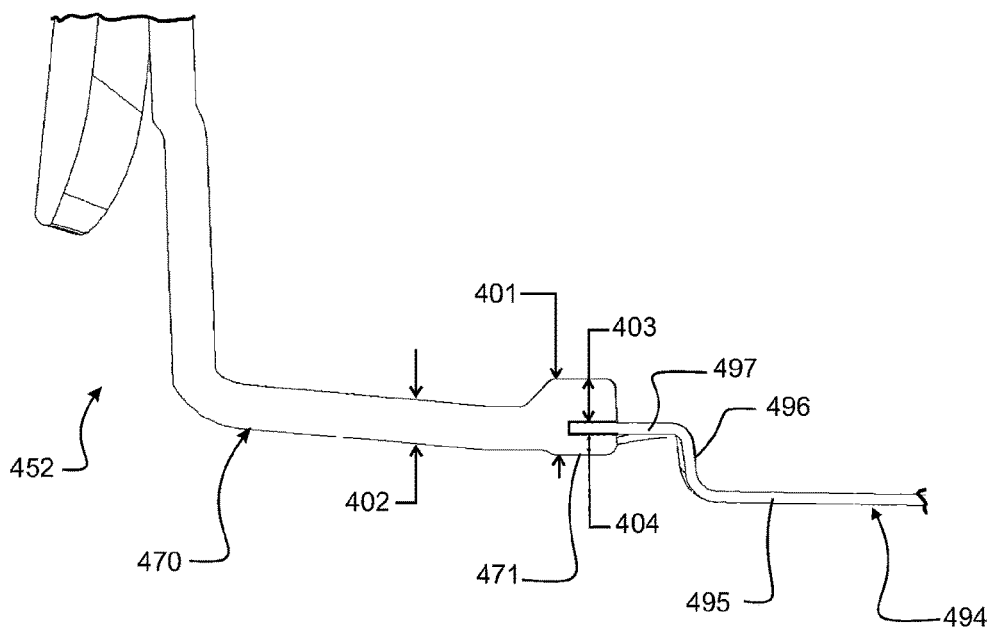
FIG. 28J shows a close-up view of area FF of FIG. 28I.
Figure 28K:
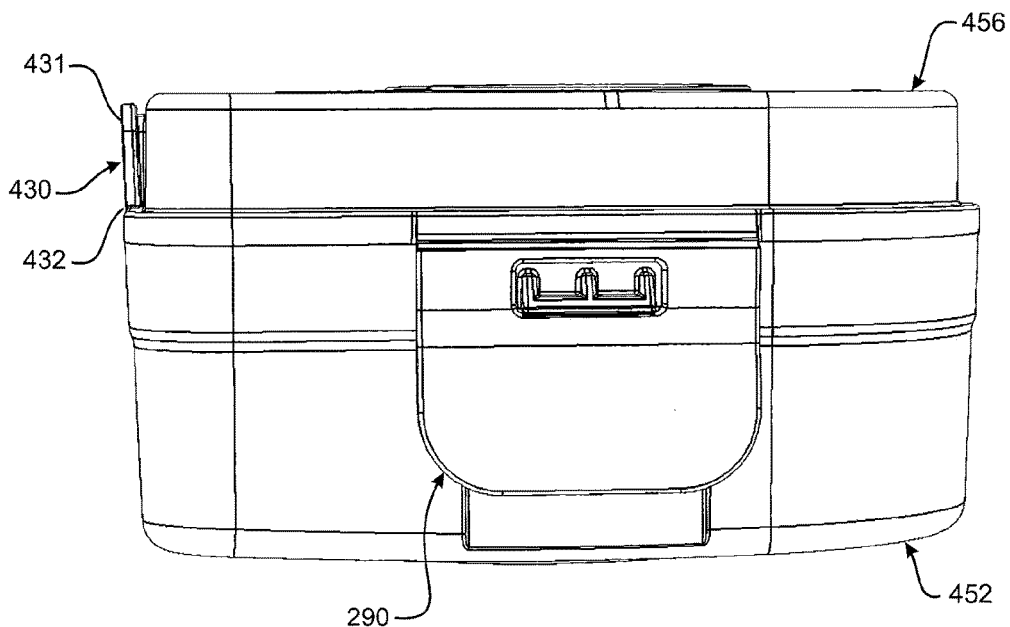
FIG. 28K shows a similar elevation view of the front end of the third embodiment humidification chamber as FIG. 28H but at an angle which shows the angled profile of the gases outlet.
Figure 28L:
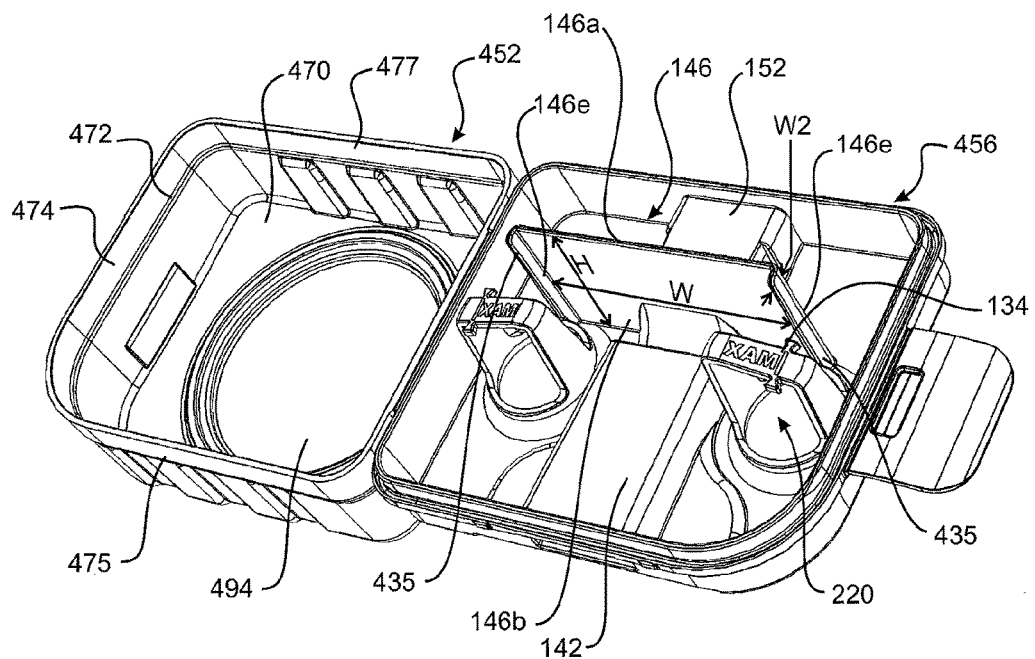
FIG. 28L shows an upper perspective view of the third embodiment humidification chamber in an open position.
Figure 28M:
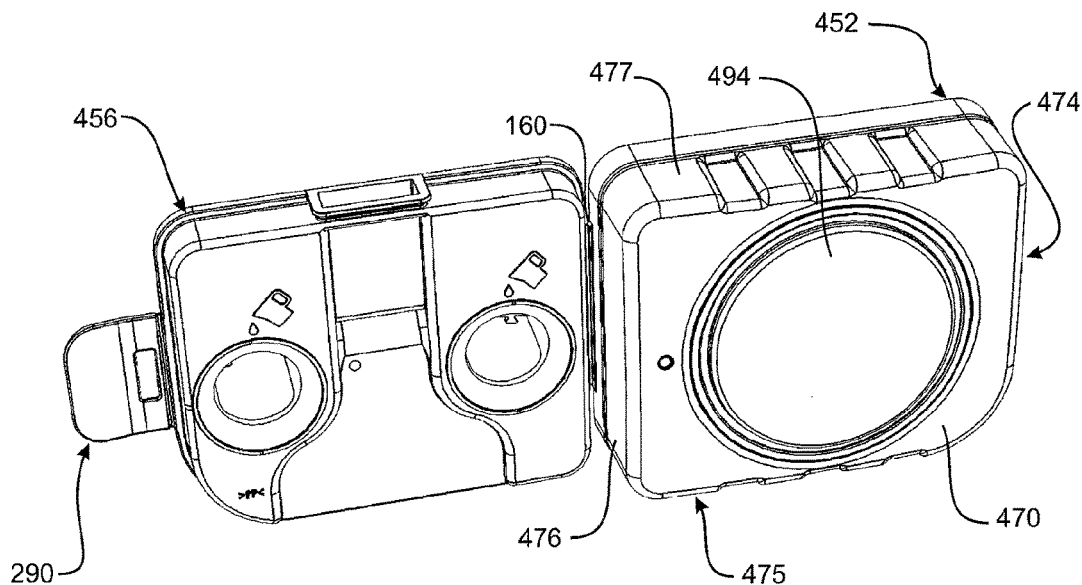
FIG. 28M shows a lower perspective view of the third embodiment humidification chamber in an open position.
Figure 28N:
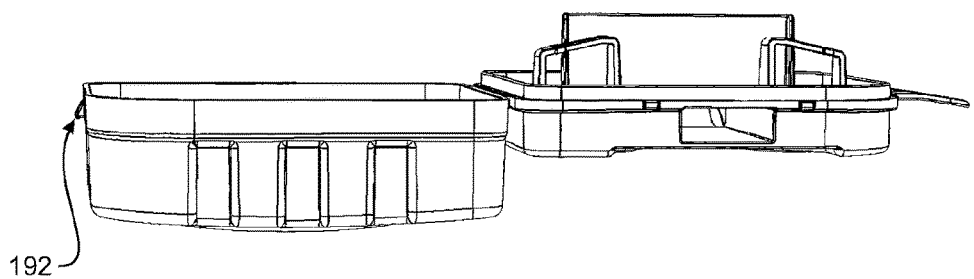
FIG. 28N shows another perspective view of the third embodiment humidification chamber in an open position from the gases inlet side of the humidification chamber.
Figure 28O:
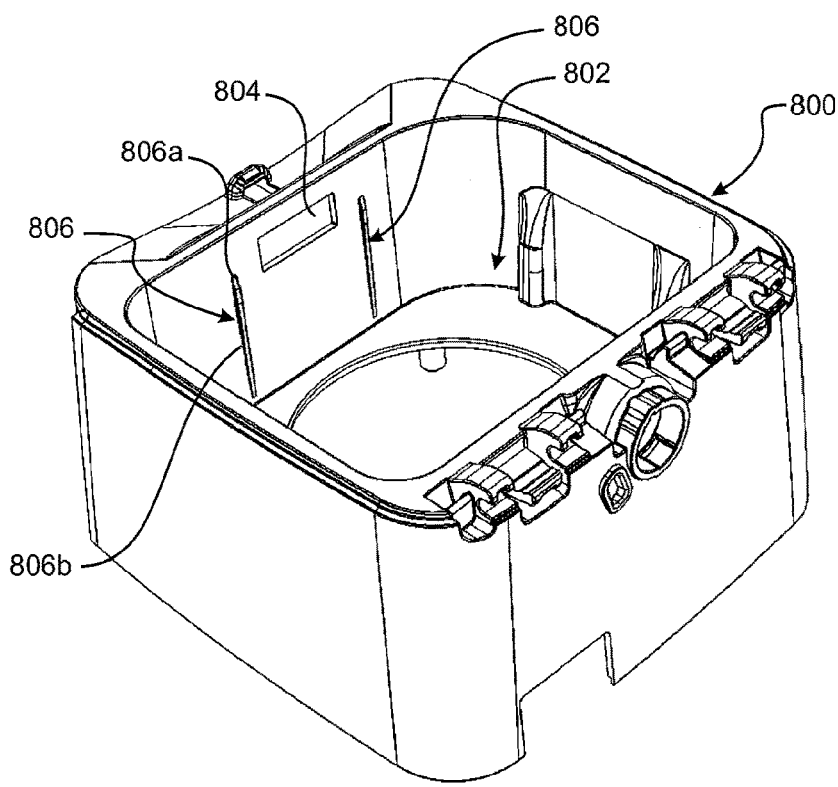
FIG. 28O shows a first upper perspective view of a lower part of a humidification compartment for receiving the third embodiment humidification chamber, with the gases inlet of the compartment being visible.
Figure 28P:
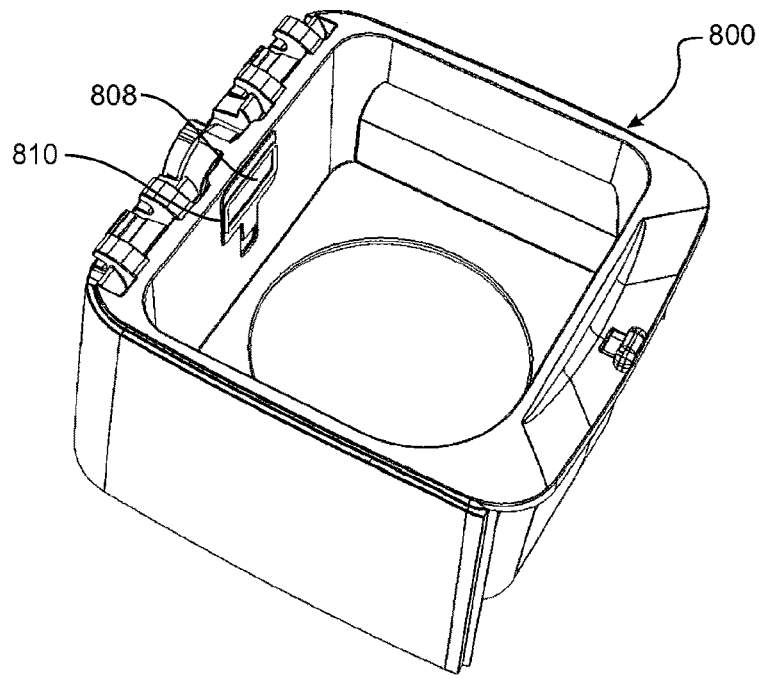
FIG. 28P shows a second upper perspective view of the humidification compartment part of FIG. 28O, with the gases outlet of the compartment being visible.
Figure 28Q:
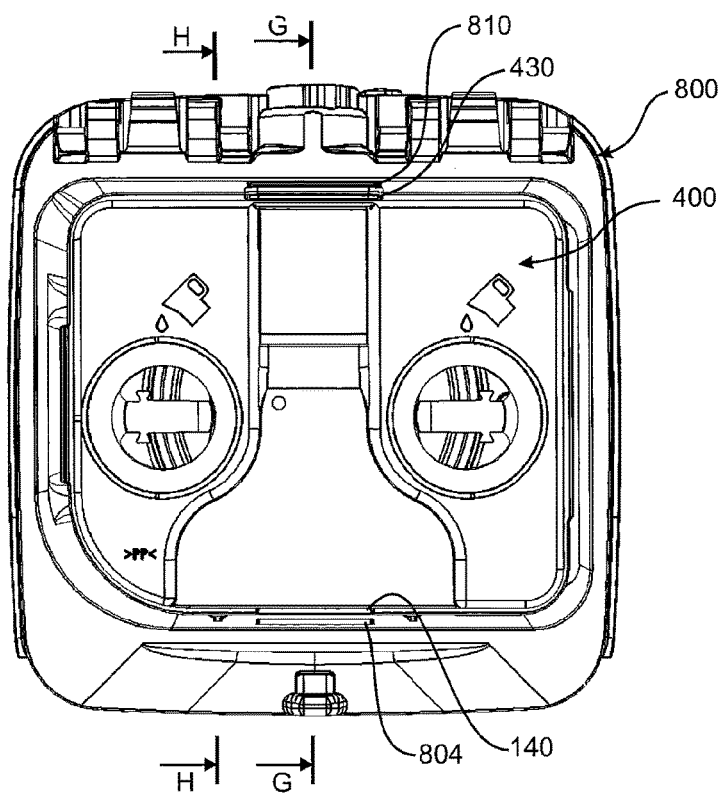
FIG. 28Q shows a plan view of the third embodiment humidification chamber installed in the humidification compartment part of FIG. 28O.
Figure 28R:
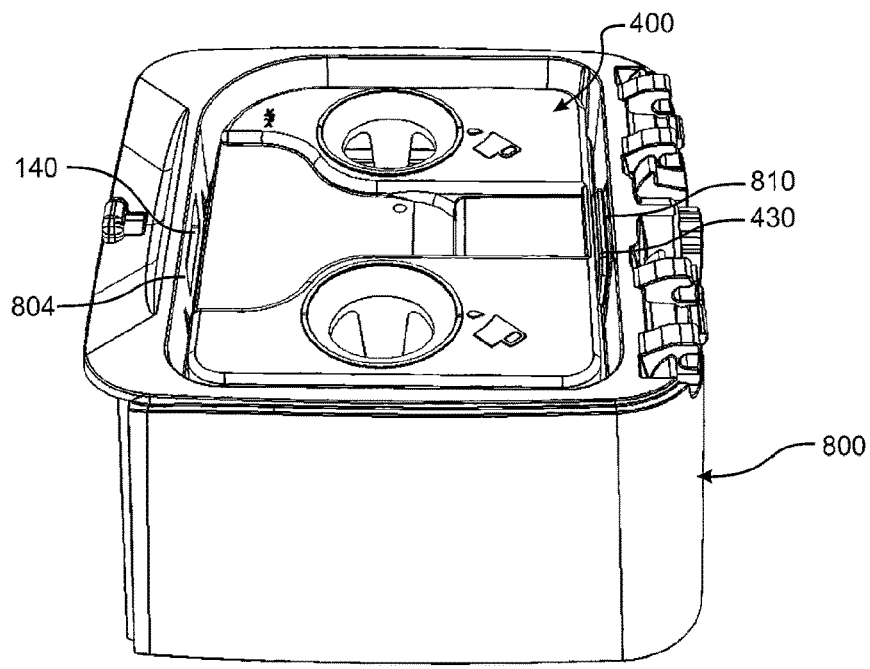
FIG. 28R shows a side perspective view of the third embodiment humidification chamber installed in the humidification compartment part of FIG. 28O.
Figure 28S:
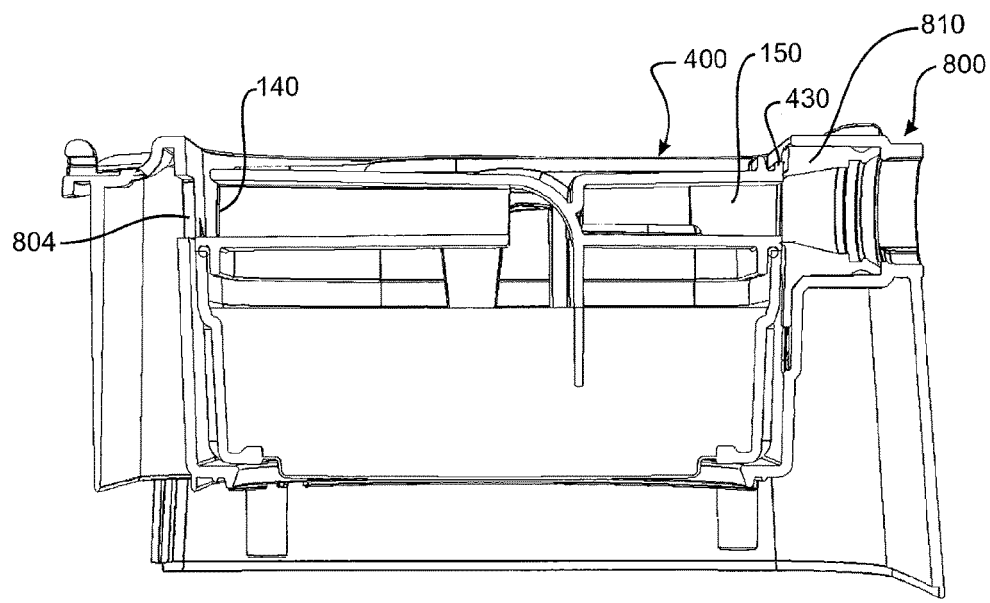
FIG. 28S shows a cross-sectional view of the third embodiment humidification chamber installed in the humidification compartment part through line GG of FIG. 28Q.
Figure 28T:
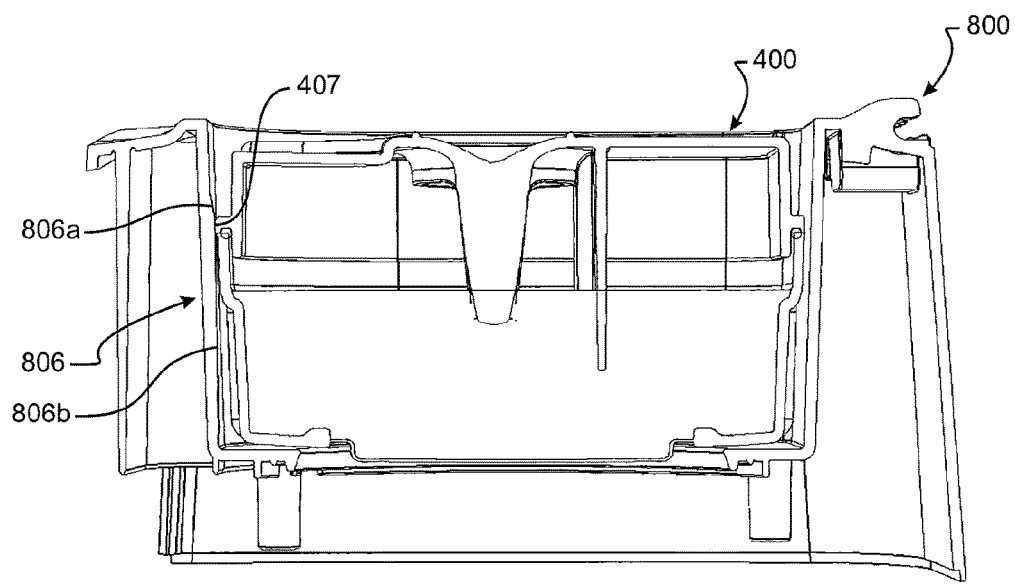
FIG. 28T shows a cross-sectional view of the third embodiment humidification chamber installed in the humidification compartment part through line HH of FIG. 28Q.

Referring to FIGS. 28A-28T, a third embodiment humidification chamber 400 will be described in further detail. The humidification chamber 400 is similar in overall shape to the previous embodiments, and where applicable similar features are represented by similar drawing reference numerals. It will be appreciated that the description of the previous embodiments in relation to similar features, including variants or alternatives, also applies to this embodiment and will not be repeated. The following description focuses on the differences of the third embodiment relative to the previous embodiments.

The primary difference with the third embodiment humidification chamber 400 is that it is a two-part chamber assembly, rather than a three-part chamber assembly like the previous embodiments. The phrases "two-part" and "three-part" assemblies are intended to refer to the number of main components of the assembly, regardless of whether they are integrally formed or otherwise connected, coupled or assemble together. In particular, the previous embodiments relate to three-part chamber assemblies comprising: an upper part (lid—part one) which is hingedly coupled to open and close relative to a lower part (cradle—part two) which releasably receives and retains a separate water tub (part three). In contrast, this third embodiment humidification chamber 400 is a two-part assembly comprising the upper part in the form of a lid 456 (part one) that is hingedly coupled at one side to a lower part that is the form of a water tub 452 (part two) comprising a thermally conductive metallic heater plate in its base surface.

In this embodiment, the lid 456 and water tub 452 (except the metallic heater plate) are formed of a rigid plastic by injection moulding, vacuum forming, or some other suitable production process, in a similar manner to the formation of the lid and cradle of the previous embodiments. Typically, the lid 456, water tub 452, and hinged coupling 160 between the lid and water tub are integrally formed together as a single item, although in alternative embodiments the lid and water tub may be formed as separate parts and then hingedly coupled via one or more separate hinging components or assemblies. The water tub and/or lid may be substantially transparent or formed as opaque depending on design requirements.

Like the previous embodiments, the humidification chamber 400 is operable or moveable between a closed position in which the lid 456 is secured to the water tub 452 to create an enclosed chamber (as shown in FIGS. 28A and 28B for example) and an open position or configuration as shown in FIGS. 28L-28N in which the lid 456 is displaced or rotated about the hinge 160 away from the water tub to open the chamber for access. One or more operable clips 290 or latches are provided at the front end of the humidification chamber for securing or locking the humidification chamber into the closed position ready for insertion and operation within a respiratory device as previously discussed.

Water Tub

Referring to FIGS. 28A, 28B, 28L, and 28M, the water tub 452 comprises a base surface 470 from which upright sidewalls extend about the periphery of the base surface. As shown, the water tub comprises front 474 and rear 476 walls at the front and rear ends of the humidification chamber respectively, and first 475 and second 477 sidewalls extending along the gases inlet and gases outlet sides of the humidification chamber respectively.

Referring to FIGS. 28D, 28E, and 28F, one or more of the walls or portions of the walls may be provided with a reinforcing profile that is configured to resist bending or deformation of the wall surfaces. In this embodiment, each of the sidewalls 475, 477 are provided with reinforced portions or regions 478, 479 respectively comprising a corrugated or undulating surface profile of alternate furrows and ridges. In this embodiment, the furrows and ridges have a vertical orientation, but it will be appreciated that a horizontal orientation may be used in the alternative if desired. In this embodiment, the thickness of the sidewalls in the reinforced or corrugated regions is substantially uniform such that the ridges and furrows and the transition zones between the ridges and furrows are of a substantially similar wall thickness as can be seen in FIG. 28D. In alternative embodiments, the thickness of the sidewalls in the reinforced regions may be non-uniform. In this embodiment, the height of each corrugated region extends on the sidewalls from the base surface to an intermediate point below the edge or rim of the water tub as shown in FIGS. 28E and 28F, but it will be appreciated that the corrugated region may start at a point above the base surface or alternatively the corrugated region may extend the entire height of the sidewalls if desired. In alternative reinforcing profiles, spaced-apart reinforcing ridges or ribs, whether vertically or horizontally oriented, or may be provided on one or more portions of the side walls, on either the inner or outer surfaces, or both. In such embodiments, the ridges or ribs increase the thickness of the wall in the region of the ridge or rib. In other alternative embodiments, the sidewalls of the water tub 452 may be stiffened or reinforced to prevent or minimise bending and/or deformation with a perimeter ledge, lip, or rim extending or protruding outwardly from or at the top perimeter edge of the water tub sidewalls. The rim may be of the type or form shown at 92 or 52a in FIG. 36 for example, i.e. integrally formed about the upper perimeter edge of the sidewalls. The reinforcing rim may be provided in combination with the reinforced regions of the sidewalls or as an alternative instead of the reinforcing regions.

Referring to the side elevation in FIGS. 28E-28H, in this embodiment the humidification chamber 400 comprises a convex or domed base surface 470 that is curved or rounded outward toward an apex defined by a central heater plate, discussed further next. In alternative embodiments, the base surface 470 may be substantially flat.

Referring to FIGS. 28D, 28L, and 28M, the base surface 470 of the water tub 452 is provided with a centrally located metallic or thermally conductive heater plate 494. In this embodiment, the heater plate 494 is circular and joined or fixed into a complementary circular aperture provided in the center of the base surface 470 of the plastic water tub 452 by overmoulding. The heater plate may be formed of a rigid and thermally conductive material, and is typically pressed or shaped from sheet metal, such as aluminum, stainless steel or any other suitable material, or could be formed by die casting for example. In this embodiment, the heater plate 494 and complementary aperture in the base surface 470 of the water tub are circular, although it will be appreciated that this shape may be varied to provide an integrated heater plate surface of any other alternative shape, including square, rectangular, or any arbitrary shape. In this embodiment, the heater plate 494 is substantially flat prior to the overmoulding process but may have a slightly outwardly domed or convex profile caused by compression force from the surrounding domed base surface after the overmoulding process. The compression force or bias which causes the slightly outwardly convex engagement surface of the heater plate reduces or resists the likelihood of the heater plate being deformed inwardly overtime and usage as a deformed inwardly concaved engagement surface would reduce the contact surface area of the heater plate with the heater pad it sits on in the humidification compartment, which would reduce the heat transfer efficiency of the configuration.

In this embodiment, the heater plate 494 is provided with a main circular contact surface 495 that is configured to protrude or extend beyond the surrounding plastic base surface 470 of the water tub 452, to encourage full engagement and heat transfer when the chamber sits on a complementary shaped heater pad in the bottom of the humidification compartment. In this embodiment, the heater plate further comprises an upright or substantially vertical wall portion 496 that extends around the periphery of the main contact surface portion 495 and an outer substantially horizontal peripheral coupling surface or ledge portion 497 that extends outwardly from the top of the wall portion 496 around the perimeter of the heater plate. As shown, the main contact surface portion 495 and outer coupling ledge 497 extend in substantially parallel planes but are displaced vertically from each other by the height of the vertical wall portion 496. As shown, it is the coupling ledge 497 of the heater plate 494 that is coupled or fixed to the surrounding plastic about the periphery of the central aperture of the base surface 470 by overmolding. In particular, an engagement portion 471 of the base surface material about the periphery of the central aperture of the base surface 470 is moulded over at least a portion of the coupling ledge 497 of the heater plate 494, about its entire periphery.

Referring to FIG. 28J, in this embodiment the overmoulding process is configured to vary the thickness of the engagement portion 471 of the base surface relative to the remainder of the base surface. In this embodiment, the overall thickness 401 of the engagement portion 471 that is moulded over at least a portion of the coupling ledge 497 of the heater plate 494 is larger than the thickness 402 of the remaining base surface 470 of the water tub. This configuration assists in reducing lifting of the plastic of the base surface 470 away from the coupling ledge 497 of the heater plate after moulding, which in turn reduces the amount of hard water deposit ingress at the transitional interface region between the metal heater plate and plastic base surface. In one arrangement, the thickness 403 of an upper portion of the engagement portion 471 above the coupling ledge 497 of the heater plate 494 is similar to or at least as thick as the thickness 402 of the remaining base surface, to reduce or minimise lifting of the upper portion away from the coupling ledge 497. As shown, in this embodiment, the thickness 404 of a lower portion of the engagement portion 471 below the coupling ledge 497 may be of smaller thickness than the thickness 403 of the upper portion of the engagement portion 471 of the base surface 470. In alternative embodiments, the thickness 404 of the lower portion of the engagement surface may also be similar to or at least as thick as the thickness 402 of the remaining base surface to reduce or minimize lifting of lower portion from the coupling ledge.

It will be appreciated that in alternative embodiments, the heater plate may be a substantially flat circular plate which is secured within the central aperture of the base surface by overmoulding such that it is substantially flush with the remainder of the base surface rather than protruding as described above.

Referring to FIG. 28L, in this embodiment, the water tub 452 is also provided with a continuous horizontal step formation 472 extending about the perimeter of the inner sidewall surface. The step formation is displaced a uniform height from the base surface of the water tub about the inner perimeter. The step formation is integrally formed into the sidewalls and may be in the form of an angled step as shown in FIG. 28I. In this configuration, the step formation 472 is located at a height from the base surface that corresponds to a maximum fill line. When the lid of the chamber is in the open position, the user may fill the water tub with water upto the level of the step formation, as an alternative option to using the water fill holes.

Lid

The lid 456 of the third embodiment humidification chamber 400 is substantially similar to the lid 56 of the previous embodiments, although there are some main differences, which will be explained in the following. It will also be appreciated that the third embodiment humidification chamber could also use the same lid 56 as previously described.

Referring to FIGS. 28C, 28I and 28L, in this embodiment the lid 456 is provided with tab water level indicators 220 of the type explained previously with reference to FIGS. 24A and 24B. In particular, the tab water level indicators 220 comprise an angle tab 134 which is suspended below each water fill aperture 120 by upright support members 132, 221 at each end. In this embodiment, the indicia "MAX" for maximum is printed backwards on the underside surface of the tab portions 134 as shown in FIG. 28L. At least the tab portions 134 are formed of transparent plastic such that the indicia "MAX" is presented to the user through in the correct readable format when viewed through the water fill holes 120.

Referring to FIGS. 28E and 28C, the inlet side perimeter wall 106 of the lid 456 is provided with a projection or projections 407, such as bumps or ridges or formations, that extend from the surface of the perimeter wall. In this embodiment, a protrusion 407 is provided on each side of the central inlet aperture 140 of the lid for engaging with aligned rails provided on the inner inlet gases side wall of the humidification compartment, which will now be explained. Referring to FIG. 28O shows a lower part of a humidification compartment 800 that is shaped and dimensioned with a complementary cavity 802 that receives and retains the humidification chamber 400. The lower part of the humidification compartment may be part of the housing or body of a respiratory device of the type previously described. As previously described with reference to FIG. 2, the humidification compartment may further comprise an openable lid for sealing or enclosing the compartment once the humidification chamber 400 is installed in the cavity. As shown, two vertical rails 406 protrude from the inner wall surface of the humidification compartment on each side of the gases inlet 804, which receives a flow of gases from the blower of the respiratory device as explained previously with reference to FIG. 2. In this embodiment, each rail 806 extends from a first upper end at or toward the height of the gases inlet 804 and a second lower end at or toward the floor surface of the compartment. In this embodiment, referring to FIGS. 28o and 28T) each rail comprises a first short start ramp portion 806a that tapers or slopes outwardly from the wall surface, and then extends into a second longer return ramp portion 806b that tapers or slopes back toward the inner wall surface. In operation, the protrusions 407 on the gases inlet side of the humidification chamber 400 are aligned with engagement rails 806 on the inlet side of the humidification compartment. As the humidification chamber 400 is lowered or inserted down into the humidification compartment, the protrusions 407 abut or engage with their respective rail 806, and the rails urge the chamber 400 toward the opposite outlet sidewall of the compartment comprising the gases outlet 808, which is shown in FIG. 28P. This configuration assists in urging and holding the gases outlet 150 of the chamber into sealing engagement or connection with the gases outlet 808 of the compartment once the chamber is full inserted or installed. In this configuration, the gases outlet 808 of the compartment is provided with a seal 810 that extends about the perimeter of the gases outlet 808. The seal may be an elastomer or rubber component or insert for example. As will be explained next, in this embodiment, the gases outlet 150 of the chamber is provided with an engagement surface 430 that sealingly engages with the seal 810 about the perimeter of the gases outlet 808 to thereby create a sealed connection between the outlets. In alternative embodiments, it will be appreciated that the seal may be provided on the gases outlet 150 of the chamber, or both the outlets of the chamber and compartment may have complementary seals.

Referring to FIGS. 28F, 28K, and FIGS. 28P-28S, in the third embodiment humidification chamber 400 the gases outlet 150 on the outlet side perimeter wall 108 of the lid 456 comprises an engagement surface or formation 430 about the perimeter of the aperture 150. The engagement surface 430 is configured to sealingly engage with the seal 810 gases outlet 808 of the humidification compartment 800 when the humidification chamber 400 is installed within the compartment. In this embodiment, the gases outlet 150 is substantially rectangular and therefore the engagement surface 430 is also substantially rectangular and comprises upper 431 and lower 432 horizontal portions extending along the upper and lower perimeters of the gases outlet 150 and side vertical portions 433, 434 along the side perimeter portions of the gases outlet 150. In this embodiment, the engagement surface 430 is substantially planar about the perimeter or periphery of the gases outlet 150 such that it may sealingly engage with a complementary seal 810 or outlet surface associated with the gases outlet 808 of the humidification compartment 800. In the arrangement shown, the engagement surface 430 is preferably angled or tilted outward relative to the vertical outlet side perimeter wall 108. In particular, as shown more clearly in FIG. 28K, the engagement surface 430 is angled such that the upper portion 431 is displaced outward from the outlet side perimeter wall 108 further than the lower portion 432. In this arrangement the engagement surface 430 can be considered as being tilted or pivoted outward about a horizontal axis extending across its surface such that the upper portion of the engagement surface protrudes or is displaced further from the outlet side perimeter wall 108 of the lid 456 than the lower portion or region 432 of the engagement surface. It will be appreciated that the same principles may be applied should the gases outlet and engagement surface be circular or otherwise shaped. The angled engagement surface 430 assists in enabling the humidification chamber to be easily received or inserted into the complementary humidification compartment 800 and assists in creating a sealed engagement or connection between the gases outlet 150 of the chamber and the gases outlet 808 of the humidification compartment 800.

Referring to FIG. 28L, the vertical flow panel 146 of the lid 456 is modified relative to the previous embodiments. In this embodiment, the vertical panel or plane 146 additionally comprises a pair of baffle portions or vanes 435 which extend along the side edges 146 of the flow panel 146 along the full height (H) of the flow panel 146, and which act as flow deflectors or guides. The side baffles 435 protrude or extend away from the first side surface 146b of the flow panel 146 along each of its side edges. In particular, the side baffles 435 extend substantially perpendicular to the flow plane 146 such that they extend towards the inlet side of the lid. In this arrangement, the side baffles 435 of the vertical flow panel 146 have a width W2 (extending in a direction perpendicular to the surface of the flow panel) that is substantially smaller than the overall width W of the vertical flow panel. In use, the side baffle portions or surfaces 435 are configured to minimise or prevent air flow exiting the inlet conduit 142 from flowing directly around the side edges 146e of the vertical flow panel toward the gases outlet conduit 152, which a flow path that results in reduced humidification. The side baffles 435 force or encourage the air to circulate back toward the inlet side of the humidification chamber and lengthen the general air flow circulation path in the chamber before the gases exit the chamber to enhance the moisture absorption. As previously described, the height (H) of the flow panel 146 is typically configured such that it protrudes or penetrates sufficiently deeply into the surface of the water to prevent gases exiting the inlet conduit 142 from short-cutting underneath the lower edge 146a and directly to the outlet conduit 152.

Hinge and Clip

As previously mentioned, the upper part or lid 456 is hingedly coupled or connected to the lower part or water tub 452 such that they are moveable between an open position in which the lid is pivoted away from the water tub (to allow the tub to be filled with water or cleaned with the lid open) and a closed position in which the lid pivots into engagement with the water tub to close the chamber. In this embodiment, lid 456 is hingedly coupled to the water tub 452 in a similar manner to the hinging coupling between the lid and cradle of the previous embodiments. In particular, the lid 456 is pivotable about a hinge located at the rear of the chamber between the closed position or configuration shown in FIGS. 28A and 28B and an open position or configuration as shown in FIGS. 28L-28N, for example. As shown in FIGS. 28A, 28G and 28M, in this embodiment the hinge is a single elongate living hinge 160 that extends along a portion of the rear end of the humidification chamber between the lid 456 and water tub 452, and is of a form as previously described in the previous embodiments.

To secure the humidification chamber in the closed configuration, one or more operable clips or clipping mechanisms are provided and are operable between a latched or locked position for securing the chamber in the closed position, or in an unlatched or unlocked position to enable the lid 456 to be pivoted away from the water tub into the open position or configuration. Referring to FIGS. 28B, 28H, 28M and 28N, in this embodiment the humidification chamber comprises a single operable clip 290 and complementary catch formation 192 of the type described with reference to FIGS. 23A and 23B. In particular, the clip 290 is pivotably mounted to the lid and is moveable into engagement with the catch 192 to securely close the chamber or may be disengaged or released from the catch 192 to enable the chamber to be opened. As shown in FIG. 28H, a recessed portion 195 is provided on the front wall of the water tub 452 in the vicinity of the clip 290 to enable a user to grip and pull the tab to disengage the clip from the catch formation 192 when desired.

Sealing

As with the previous embodiments, the third embodiment chamber 400 need not necessarily be sealed between the lid 456 and water tub 452. However, it may be sealed if desired as shown in this embodiment. Referring to FIG. 28I, the ledge 105 of the lid 456 is provided with or forms a perimeter groove or recess and a seal 99 is mounted in the groove about the perimeter of the lid in a similar configuration to that described with reference to the embodiment of FIG. 36. As shown, the seal 99 engages with the upper surface or rim 461 of the perimeter wall of the water tub 452 when the chamber is closed to seal the chamber. The other seal configurations discussed with reference to FIG. 36 may also be employed in alternative configurations.

Fourth Embodiment Humidification Chamber—with Sleeve

Figure 29A:
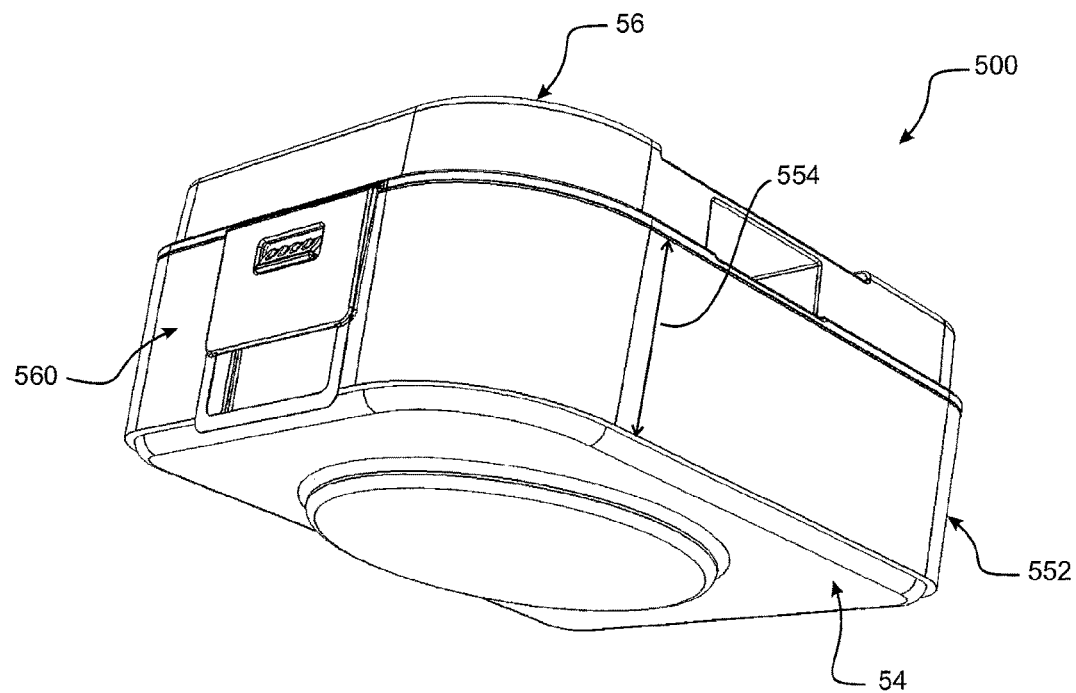
FIG. 29A shows a perspective view of a fourth embodiment humidification chamber comprising a lid, sleeve and water tub.
Figure 29B:
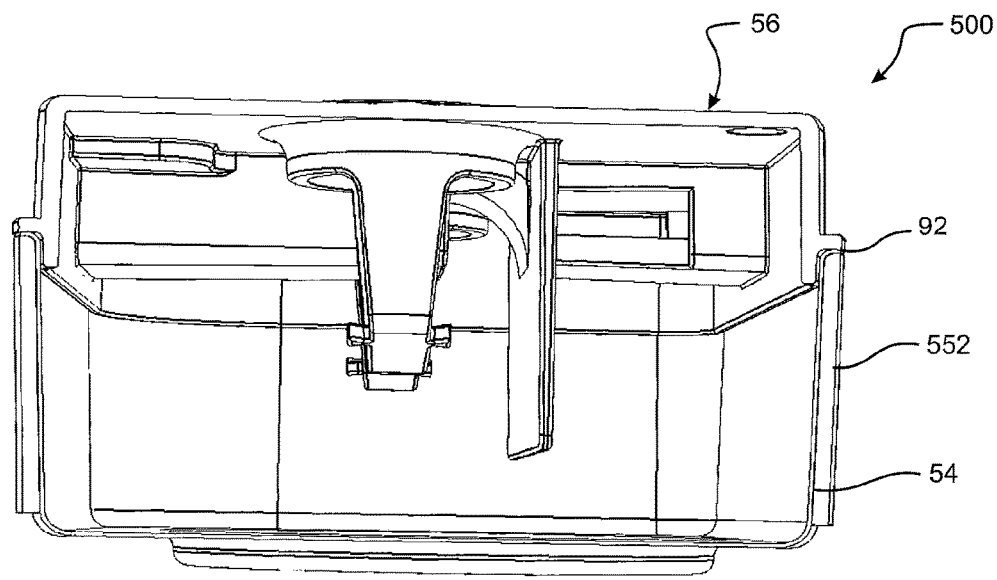
FIG. 29B shows a cross-sectional view through the fourth embodiment humidification chamber.

Referring to FIGS. 29A and 29B, the fourth embodiment humidification chamber 500 is a variant of the second embodiment humidification chamber 300. In this embodiment, the lid 56 is not hingedly coupled at one end to a full cradle but rather to a sleeve 552 in the form of a continuous perimeter wall that encircles or extends about the entire peripheral wall of the water tub 54 as shown. In particular, the sleeve 552 leaves the entire base surface 54 in the water tub exposed. The sleeve 552 is preferably formed of the same material as the lid, for example injection molded from plastic or similar. The height of the sleeve as indicated at 554 may be varied as desired. In this embodiment, the sleeve extends substantially from the upper edge of the rim of the water tub to the base surface of the water tub, but may be thinner and extend only part way down the peripheral wall from the upper edge in alternative embodiments. As shown in FIG. 29B, the sleeve is prevented from lifting or sliding off the water tub 54 by virtue of the lip or rim 92 extending outwardly from the upper edge of the water tub 54. Otherwise, the humidification chamber is substantially similar to the previous embodiment and is provided with a living hinge coupling the lid to the sleeve 52 along the rear end (not shown) and a clipping mechanism 560 at the front, which in this embodiment is of a form described with respect to FIGS. 21A-21C.

Fifth Embodiment Humidification Chamber—with Internal Clips

Figure 30A:
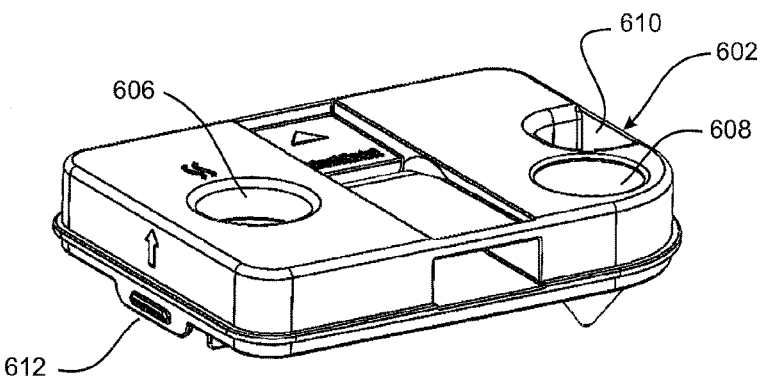
FIG. 30A shows a perspective view of a lid of a humidification chamber in accordance with a fifth embodiment of the invention comprising a lid which clips into a water tub.
Figure 30B:
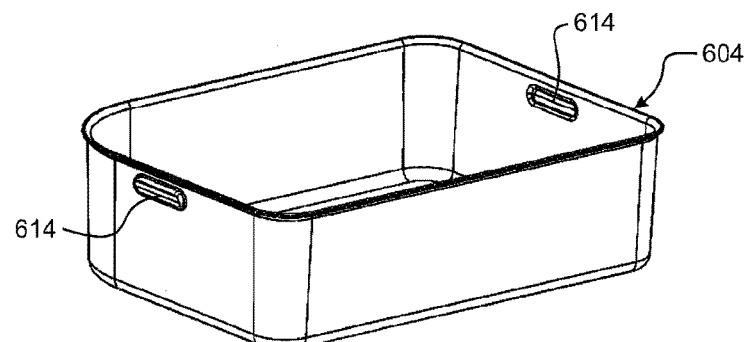
FIG. 30B shows a perspective view of the water tub of the fifth embodiment humidification chamber.
Figure 30C:
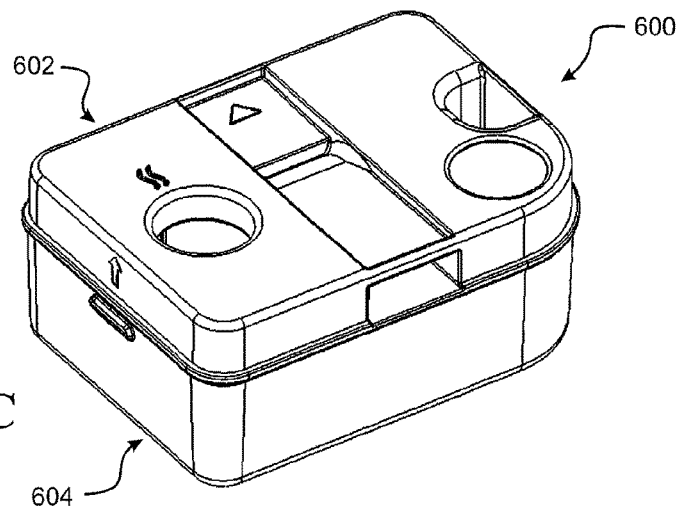
FIG. 30C shows a perspective view of the lid and water tub of the fifth embodiment humidification chamber in an assembled and closed configuration.

Referring to FIGS. 30A-30C, the fifth embodiment humidification chamber 600 (see FIG. 30C) comprises a plastic lid 602 which is releasably coupled to a metal water tub 604 (see FIG. 30B) via internal clips. The plastic lid 602 is substantially similar to the lids of the previous embodiments although comprising a slightly different water level indicator configuration. In particular, there is a water fill hole 606 centrally located toward one end of the lid and a conical water level indicator 608 located toward one corner of the opposite end of the lid. Additionally, a finger gripping recess 610 is provided centrally on the water level indicator end of the lid. The internal structure of the lid 602 is otherwise similar, including the gases inlet, gases outlet and vertical flow plane configuration.

The water tub 604 is entirely formed from metal such as stainless steel, aluminum or similar. Optionally, a sleeve or cradle of insulating material such as plastic or other thermally insulating material may be provided on the outer peripheral walls and/or underside surfaces of the metal tub to prevent user from burning their hands if picking up the metal tub, although the user may pick up the metal tub via the lid by gripping of the water fill aperture 606 and the figure grip recess 610 with a finger and thumb for example.

The lid 602 is not hingedly coupled to the water tub 604 but rather is completely detachably removable from the water tub. Each end of the lid is provided with clips or engagement protrusions 612 (only one end visible) which are configured to engage into the complimentary recesses 614 provided at each end of the water tub 604 at or toward the upper edge of the water tub. Assembling the lid 602 with the water tub 604 requires the user to press the lid until the clip formations 612 engage in the complimentary recesses 614. To release the lid, the user pulls the lid in a vertical direction from the water tub with sufficient force to disengage the clip formations 612 from the recesses 614.

Sixth Embodiment Humidification Chamber—with Ducted Lid

Figure 31A:
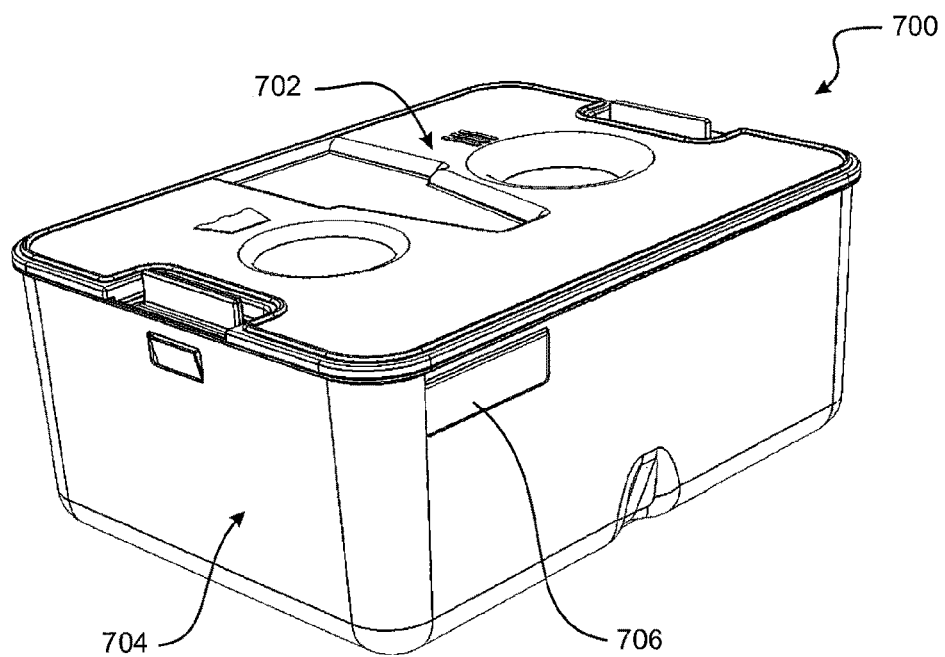
FIG. 31A shows an upper perspective view of a closed humidification chamber in accordance with a sixth embodiment of the invention comprising a ducted lid which clips into a water tub.
Figure 31B:
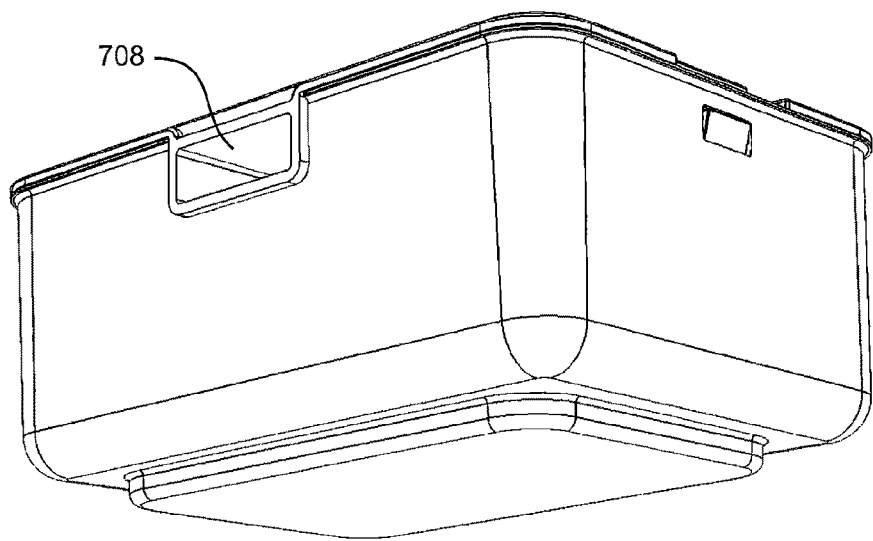
FIG. 31B shows a lower perspective view of the sixth embodiment humidification chamber.

Referring to FIGS. 31A-35, the sixth embodiment humidification chamber 700 will be described. This embodiment comprises a plastic lid 702 which clips into a complimentary shaped metal water tub 704 by a similar manner described above with reference to the fifth embodiment humidification chamber 600. FIG. 31A shows the inlet aperture 706 of the humidification chamber and FIG. 31B shows the gases outlet 708 of the humidification chamber.

Figure 32:
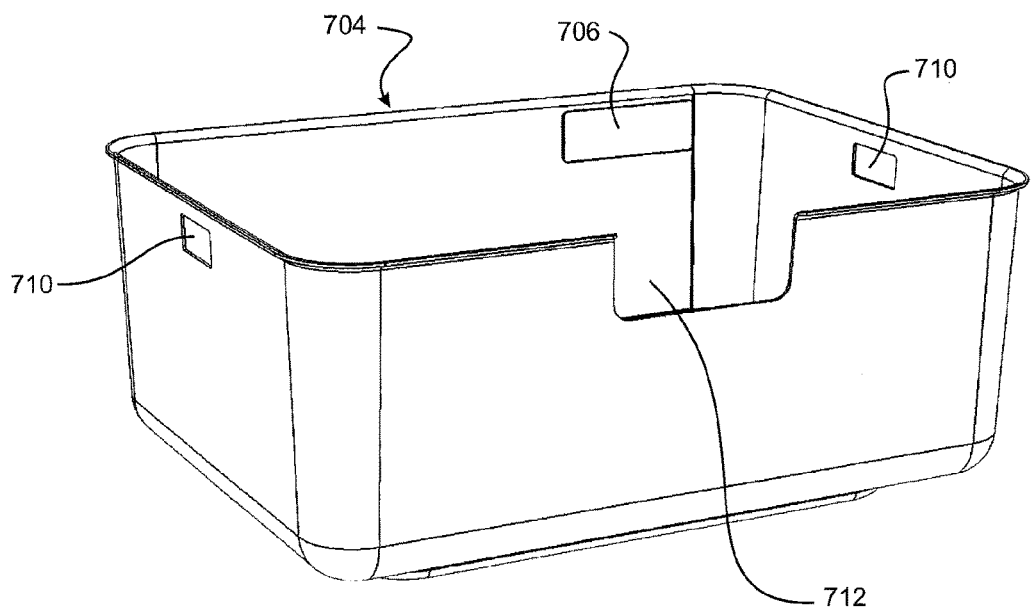
FIG. 32 shows a perspective view of the water tub of the sixth embodiment humidification chamber.

Referring to FIG. 32, in this embodiment the water tub is formed from metal or other thermally conductive material such that it may directly contact or sit on a heater base. Engagement apertures 710 are provided at each end of the water tub for receiving complimentary clips resilient clips 730 provided in the lid 702 to secure the lid to the water tub. The gases inlet 706 is an aperture provided through the peripheral wall of one side of the water tub toward a corner at the upper edge of the water tub, although it may be centrally or otherwise be located. On the opposite side of the water tub is provided a cut out or recess 712 within which the gases outlet 708 of the lid may sit when the lid is engaged with the water tub in a closed or assembled configuration.

Figure 33:
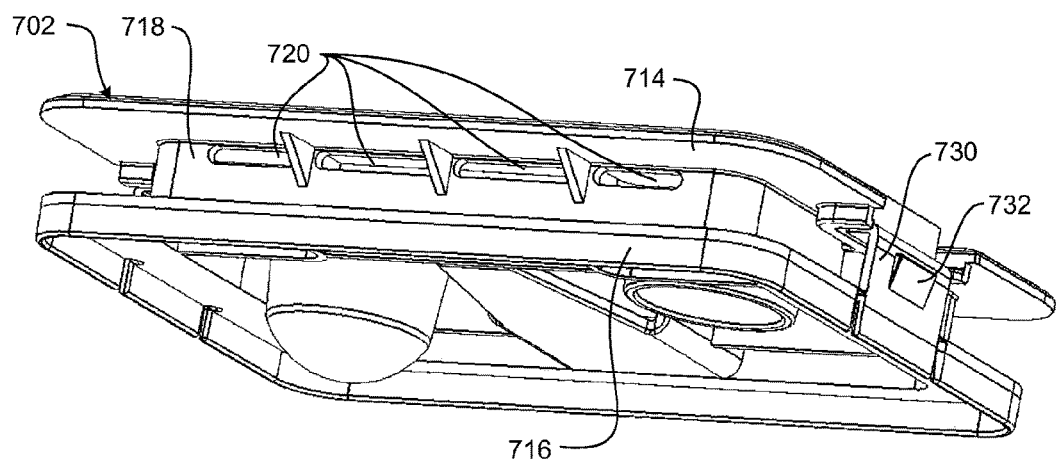
FIG. 33 shows a first underside perspective view of the ducted lid of the sixth embodiment humidification chamber.
Figure 34:
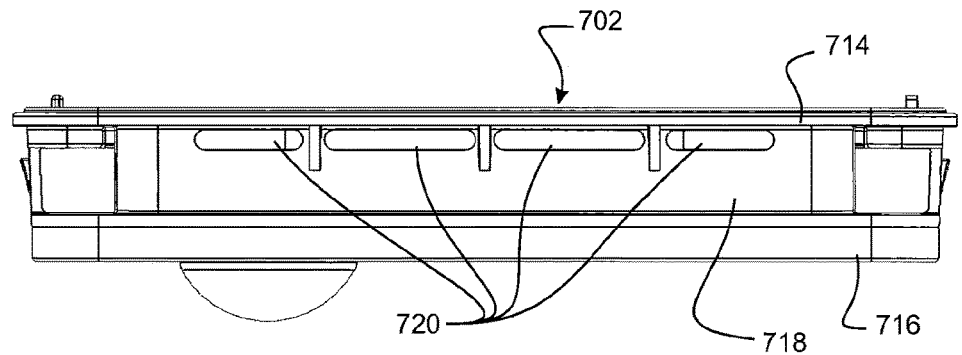
FIG. 34 shows a side elevation view of the ducted lid of FIG. 33.
Figure 35:
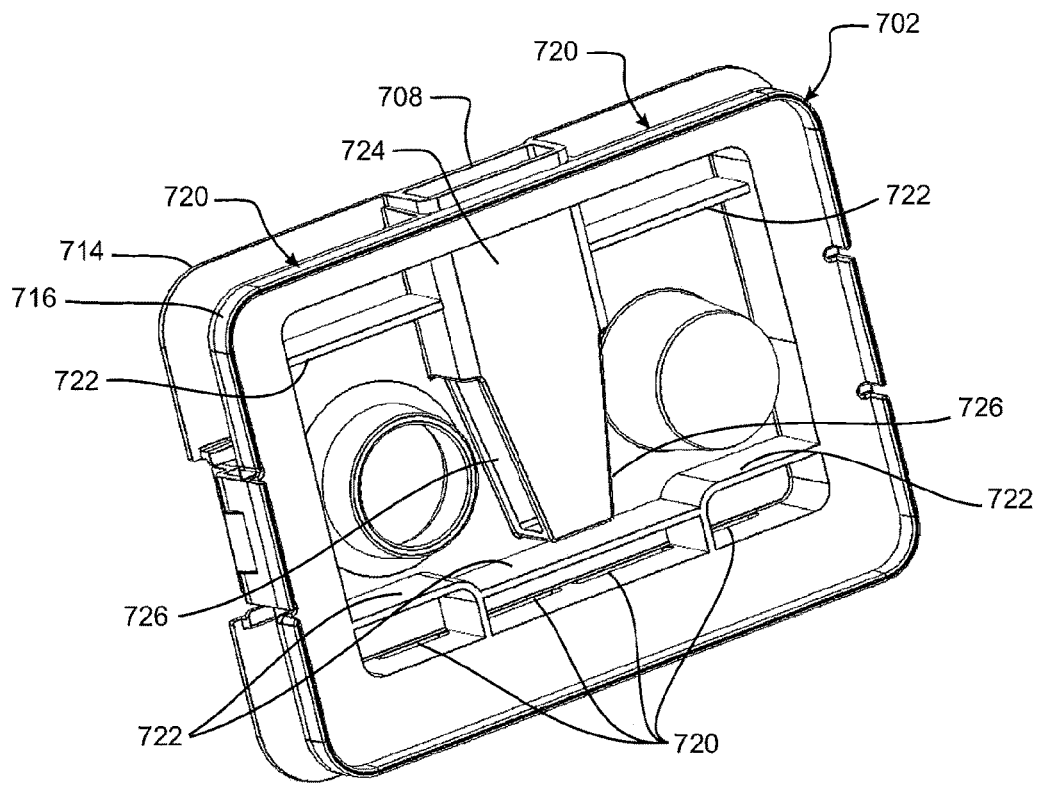
FIG. 35 shows a second underside perspective view of the ducted lid of FIG. 33.

Referring to FIGS. 33-35, the lid 702 comprises an upper frame member 714 that is coupled to a lower frame member 716 via an internal vertical wall 718. The internal wall is inset or displaced from the edge of the frame members 714, 716 about the periphery of the lid such that a perimeter gases flow channel is formed about a substantial portion of the perimeter within the lid when engaged with the tub 704. As the gases enter the perimeter channel via the inlet 706, the gases flow about the channel and enter into the internal volume of the humidification chamber via a series of one or more internal inlet apertures 720 formed through the internal wall 718. In this embodiment, the bulk of the inlet apertures 720 are provided on the inlet side wall, but one or more apertures may be spread about the entire peripheral surface of the internal wall, including the end walls and the opposite side wall located adjacent the outlet, as indicated in FIG. 35 at 720, although not visible. Additionally or alternatively, inlet apertures could be provided through the lower frame member 716 about at least a portion of the periphery of the lid.

Referring to FIG. 35, the internal or underside surface of the lid within the internal perimeter wall 718 is provided with a configuration of vertical flow planes 722 associated with each internal inlet aperture 720 and which forces the incoming gases streams down into the volume of the humidification chamber to enhance the humidification process. The gases outlet 708 comprises an outlet conduit 724 that extends horizontally into the internal volume of the lid from the aperture 708 and which terminates with inlet apertures 726 which enables the humidification gases to enter the outlet conduit 724 and exit the humidification chamber via the gases outlet 708. Referring to FIG. 33, centrally located at each end of the lid 702 is a resilient spring clip 730 comprising a clipping formation 732 that is configured to engage in the complimentary engagement aperture 710 of the water tub to secure the lid to the water tub.

Embodiments

1. A humidification chamber for humidifying gases, comprising: a water tub that is configured to receive a volume of water; a cradle defining an open cavity within which the water tub is received; a lid hingedly coupled to the cradle for enclosing the water tub to define the interior volume of the humidification chamber and which is movable between a closed position in which the water tub is closed by the lid and an open position in which the water tub is open; one or more operable clips for securing the lid in the closed position; a gases inlet for receiving a flow of gases into the interior volume of the humidification chamber; and a gases outlet through which a humidified flow of gases may exit the interior volume of the humidification chamber.

2. A humidification chamber according to paragraph 1 wherein the lid and cradle are formed of rigid plastic.

3. A humidification chamber according to paragraph 1 or paragraph 2 wherein the lid and cradle are hingedly coupled by a living hinge and are integrally formed as a single item.

4. A humidification chamber according to any one of the preceding paragraphs wherein the water tub is formed of a thermally conductive material.

5. A humidification chamber according to paragraph 4 wherein the water tub is formed from metal.

6. A humidification chamber according to any one of the preceding paragraphs wherein the water tub is defined by a base surface and a perimeter wall that extends upwardly from the base, and wherein the cradle comprises a complementary base surface and upwardly extending perimeter wall and wherein the perimeter wall of the cradle is discontinuous about the perimeter of the cradle so as to expose one or more portions of the peripheral wall of the water tub retained within the cradle.

7. A humidification chamber according to paragraph 6 wherein a heat transfer contact surface protrudes from the base surface of the water tub and the cradle is provided with a complementary aligned aperture through which the contact surface of the water tub extends such that it protrudes beyond the underside of the base surface of the cradle.

8. A humidification chamber according to any one of the preceding paragraphs wherein the water tub is releasably received within the cradle by slidable engagement.

9. A humidification chamber according to any one of the preceding paragraphs wherein the gases inlet and gases outlet are provided on opposite sides of the lid.

10. A humidification chamber according to paragraph 9 wherein the lid comprises a vertical flow plane that extends downwardly from the underside of the lid in a central region of the lid.

11. A humidification chamber according to paragraph 10 wherein the gases inlet is coupled to an inlet conduit that extends between an inlet end at the gases inlet and an outlet end located at or toward an upper central region of the interior volume of the humidification chamber and adjacent a first side surface of the vertical flow plane such that the incoming gases flow enters the interior volume of the humidification chamber at that upper central region.

12. A humidification chamber according to paragraph 11 wherein a flow director formation in the form of an inverted curved ramp surface is located between the outlet end of the inlet conduit and the first side surface of the vertical flow plane.

13. A humidification chamber according to paragraph 11 or paragraph 12 wherein the gases outlet is coupled to an outlet conduit that extends between an inlet end located at or toward an upper central region of the interior volume of the humidification chamber and adjacent a second side of the vertical flow plane and an outlet end at the gases outlet.

14. A humidification chamber according to any one of the preceding paragraphs wherein the lid comprises one or more water fill apertures and at least one water fill aperture comprising an associated maximum water level indicator comprising a tab member that is supported from the underside of the lid such that it extends into the field of view of the interior volume of the humidification chamber visible directly through the water fill aperture.

15. A humidification chamber according to any one of the preceding paragraphs wherein the humidification chamber has an overall shape defined by front and end walls between which side walls extend, and the walls extending between an upper surface of the lid and base surface of the cradle, and wherein the lid is hingedly coupled to the cradle at the rear end of the humidification chamber, and at least one operable clip is provided at the front end of the humidification chamber.

16. A humidification chamber according to any one of the preceding paragraphs wherein at least one operable clip is provided in the form of a torsion clip that is mounted to either the lid or cradle and which is configured to engage with a catch provided on either the cradle or lid, respectively.

17. A humidification chamber according to any one of paragraphs 1-15 wherein at least one operable clip is provided that is hingedly coupled to the lid or cradle and which is configured to engage with a catch provided on either the cradle or lid, respectively.

18. A humidification chamber for humidifying gases, comprising: a water tub that is configured to receive a volume of water; a lid hingedly coupled to the water tub for enclosing the water tub to define the interior volume of the humidification chamber and which is movable between a closed position in which the water tub is closed by the lid and an open position in which the water tub is open; one or more operable clips for securing the lid in the closed position; a gases inlet for receiving a flow of gases into the interior volume of the humidification chamber; and a gases outlet through which a humidified flow of gases may exit the interior volume of the humidification chamber.

19. A humidification chamber according to paragraph 18 wherein the lid is formed from rigid plastic.

20. A humidification chamber according to paragraph 18 or paragraph 19 wherein the water tub is formed of rigid plastic and comprises a base surface and a perimeter wall that extends upwardly from the base, and wherein the base surface comprises a heater plate.

21. A humidification chamber according to paragraph 20 wherein the heater plate is secured within an aperture of the base surface of the water tub by overmolding.

22. A humidification chamber according to paragraph 21 wherein a peripheral coupling surface of the heater plate is secured within a periperhal engagement portion of the base surface about the aperture of the water tub by overmolding such that the thickness of the engagement portion is greater than the thickness of remaining base surface.

23. A humidification chamber according to paragraph 22 wherein the engagement portion comprises an upper portion above the coupling surface of the heater plate and a lower portion below the coupling surface, and wherein the upper portion is at least as thick as the remaining base surface.

24. A humidification chamber according to any one of paragraphs 20-23 wherein the heater plate is metallic.

25. A humidification chamber according to any one of paragraphs 20-24 further comprising a step formation about the inner surface perimeter of the wall of the water tub, the step formation being configured at a height above the base surface of the water tub corresponding to a maximum fill line indicator.

26. A humidification chamber according to any one of paragraphs 20-25 wherein the base surface of the water tub is domed such that it curves outward toward a central apex defined by the heater plate.

27. A humidification chamber according to any one of paragraphs 20-26 wherein the perimeter wall of the water tub comprises one or more reinforced regions.

28. A humidification chamber according to paragraph 27 wherein the reinforced region(s) of the perimeter wall comprises corrugated surfaces of alternating ridges and furrows.

29. A humidification chamber according to any one of paragraphs 18-28 wherein the lid and water tub are hingedly coupled by a living hinge and are integrally formed as a single item.

30. A humidification chamber according to any one of paragraphs 18-29 wherein the gases inlet and gases outlet are provided on opposite sides of the lid.

31. A humidification chamber according to paragraph 30 wherein the lid comprises a vertical flow plane that extends downwardly from the underside of the lid in a central region of the lid.

32. A humidification chamber according to paragraph 31 wherein the vertical flow plane further comprises a pair of side baffles that each extend from a respective side edge of the vertical flow plane toward the side of the lid comprising the gases inlet.

33. A humidification chamber according to paragraph 31 or paragraph 32 wherein the gases inlet is coupled to an inlet conduit that extends between an inlet end at the gases inlet and an outlet end located at or toward an upper central region of the interior volume of the humidification chamber and adjacent a first side surface of the vertical flow plane such that the incoming gases flow enters the interior volume of the humidification chamber at that upper central region.

34. A humidification chamber according to paragraph 33 wherein a flow director formation in the form of an inverted curved ramp surface is located between the outlet end of the inlet conduit and the first side surface of the vertical flow plane.

35. A humidification chamber according to paragraph 33 or paragraph 34 wherein the gases outlet is coupled to an outlet conduit that extends between an inlet end located at or toward an upper central region of the interior volume of the humidification chamber and adjacent a second side of the vertical flow plane and an outlet end at the gases outlet.

36. A humidification chamber according to any one of paragraphs 18-35 wherein the gases outlet of the lid comprises an engagement surface about the perimeter of the gases outlet that is tilted outwardly such that an upper portion of the engagement surface is displaced further outward from the lid than a lower portion of the engagement surface.

37. A humidification chamber according to any one of paragraphs 18-36 wherein the lid comprises one or more water fill apertures and at least one water fill aperture comprising an associated maximum water level indicator comprising a tab member that is supported from the underside of the lid such that it extends into the field of view of the interior volume of the humidification chamber visible directly through the water fill aperture.

38. A humidification chamber according to any one of paragraphs 18-37 wherein the humidification chamber has an overall shape defined by front and end walls between which side walls extend, and the walls extending between an upper surface of the lid and base surface of the water tub, and wherein the lid is hingedly coupled to the water tub at the rear end of the humidification chamber, and at least one operable clip is provided at the front end of the humidification chamber.

39. A humidification chamber according to any one of paragraphs 18-38 wherein at least one operable clip is provided in the form of a torsion clip that is mounted to either the lid or water tub and which is configured to engage with a catch provided on either the water tub or lid, respectively.

40. A humidification chamber according to any one of paragraphs 18-39 wherein at least one operable clip is provided that is hingedly coupled to the lid or water tub and which is configured to engage with a catch provided on either the water tub or lid, respectively.

41. A humidification chamber according to any one of paragraphs 18-40 further comprising a seal about the perimeter of the chamber between the lid and water tub to seal the chamber when it is in a closed position.

42. A respiratory assistance device configured to provide a heated and humidified gases stream, comprising: a device gases inlet configured to receive a supply of gases; a blower configured to generate a pressurised gases stream from the supply of gases; a humidifier configured to heat and humidify the pressurised gases stream; a device gases outlet for the heated and humidified gases stream; and a flow path for the gases stream through the respiratory device from the gases inlet though the blower unit and humidification unit to the gases outlet, and wherein the humidifier comprises a sealable humidification compartment that is configured to receive and retain a removable humidification chamber according to any one of the preceding paragraphs.

43. A respiratory assistance device according to paragraph 42 wherein the humidification compartment comprises a lid that is movable between an open position to enable removal of the humidification chamber and a closed position to seal the humidification chamber within the humidification compartment.

44. A respiratory assistance device according to paragraph 42 or paragraph 43 wherein the humidification compartment comprises a gases inlet connected to the flow path to receive the pressurised gases stream from the blower to create a pressurised humidification compartment and a gases outlet connected to the device gases outlet of the flow path.

45. A respiratory assistance device according to paragraph 44 wherein the gases inlet of the humidification chamber is open within the humidification compartment to receive an incoming flow of gases from within the pressurised humidification compartment.

46. A respiratory assistance device according to paragraph 44 or paragraph 45 wherein the gases outlet of the humidification compartment is sealingly connected to the gases outlet of the humidification chamber.

47. A respiratory assistance device according to any one of paragraphs 42-46 wherein the humidification compartment comprises a heater pad upon which the humidification chamber sits.

48. A respiratory device according to any one of paragraphs 42-47 wherein the device is contained within a single housing.

49. A respiratory device according to any one of paragraphs 42-48 wherein the device is a CPAP respiratory device.

The foregoing description of the invention includes preferred forms thereof. Modifications may be made thereto without departing from the scope of the invention as defined by the accompanying claims.

What is claimed is:

1. A humidification chamber configured to be received in a compartment of a respiratory assistance device, the humidification chamber configured to humidify a pressurized gases stream generated by a blower of the respiratory assistance device, the humidification chamber comprising:
    a water tub configured to receive a volume of water, the water tub comprising a base surface, a perimeter wall that extends upwardly from the base surface and a perimeter rim extending from an upper perimeter wall portion of the perimeter wall;
    a lid, the lid being operable between a closed configuration in which the lid is secured to the water tub to create an enclosed chamber and an open configuration in which the lid is displaced away from the water tub to open the chamber for access;
    the lid comprising an upper perimeter wall, a ledge extending from the upper perimeter wall, and a lower perimeter wall portion extending downward from the ledge when the lid is positioned over the water tub in a level configuration, the lower perimeter wall portion including clearance from an adjacent surface of the upper perimeter wall portion of the water tub below the water tub perimeter rim when the lid is positioned in the closed configuration with respect to the water tub;
    the lid further comprising a gases inlet configured to be sealingly connected to a gases inlet of the compartment of the respiratory assistance device, wherein the gases inlet of the lid is provided with an associated inlet conduit that extends into the interior volume of the humidification chamber; and the lid further comprising a gases outlet configured to be sealingly connected to a gases outlet of the compartment, wherein the gases outlet of the lid is provided with an outlet conduit extending into the interior volume of the humidification chamber;

a flexible seal provided about a perimeter of the humidification chamber between the lid and the water tub, the seal sealingly engaging the perimeter rim of the water tub and the ledge of the lid when the humidification chamber is in the closed configuration to seal the chamber.

2. The humidification chamber of claim 1, wherein the lid and water tub are pivotally connected such that the lid pivots away from the water tub when in the open configuration.

3. The humidification chamber of claim 1, wherein the inlet conduit directs the inlet gases flow stream into a central zone or region of the lid.

4. The humidification chamber of claim 1, wherein the inlet conduit comprises one or more bends or turns.

5. The humidification chamber of claim 1, wherein the outlet conduit extends into a central zone or region of the lid.

6. The humidification chamber of claim 4, wherein a flow directing formation is provided at the exit of the inlet conduit to direct the gases stream exiting the inlet conduit.

7. The humidification chamber of claim 6, wherein the flow direction formation comprises a vertical flow panel which extends downwardly from the lid.

8. The humidification chamber of claim 1, further comprising one or more clips configured to engage with a complementary catch for securing the lid in the closed position; wherein the one or more clips comprises an engagement aperture on the lid and its complementary catch is a protrusion or formation that is aligned with the clip such that it engages into the engagement aperture of the clip when the clip is in an engaged position to secure the lid in the closed position, wherein the protrusion or formation comprises a camming surface that is configured to cause its respective clip to pivot or flex outwardly before snapping into the fully engaged position with the complementary catch, when the lid is moved into the closed position without the user needing to operate the clip in order to engage it with the complementary catch.

9. The humidification chamber of claim 1, wherein the water tub is provided with a heat transfer contact surface that protrudes from an underside of the water tub base surface.

10. The humidification chamber of claim 9, wherein the heat transfer contact surface is configured to rest on a heater base within the compartment of the respiratory assistance device when the chamber is received within the compartment.

11. The humidification chamber of claim 9, wherein the heat transfer contact surface is of a depth relative to a remainder of the base surface of the water tub that it enables it to extend through an aperture and protrude below the underside of the water tub base surface.

12. The humidification chamber of claim 1, wherein the rim of the water tub extends from an upper edge of the perimeter wall of the water tub.

13. The humidification chamber of claim 12, wherein the rim of the water tub is continuous.

14. The humidification chamber of claim 12, wherein the rim of the water tub extends outwardly from the perimeter wall of the water tub.

15. The humidification chamber of claim 1, wherein the ledge of the lid is provided about the entire perimeter wall of the lid.

16. The humidification chamber of claim 15, wherein the ledge of the lid extends outwardly from the perimeter wall of the lid.

17. The humidification chamber of claim 16, comprising a hinge between the lid and water tub, the hinge being configured such that the lid can be displaced away from the water tub.

18. A respiratory assistance device configured to provide a heated and humidified gases stream, comprising:

a gases inlet configured to receive a supply of therapeutic gases;

a blower configured to generate a pressurized gases stream from the supply of gases at an outlet of the blower;

a humidification compartment comprising a heater base;

a humidification chamber configured to be received by the humidification compartment, the humidification chamber comprising:

a water tub configured to receive a volume of water, the water tub comprising a base surface, a perimeter wall that extends upwardly from the base surface and a perimeter rim extending from an upper perimeter wall portion of the perimeter wall;

a lid being operable between a closed configuration in which the lid is secured to the water tub to create an enclosed chamber and an open configuration in which the lid is displaced away from the water tub to open the chamber for access;

the lid comprising an upper perimeter wall, a ledge extending from the upper perimeter wall, and a lower perimeter wall portion extending downward from the ledge when the lid is positioned over the water tub in a level configuration, the lower perimeter wall portion including clearance from an adjacent surface of the upper perimeter wall portion of the water tub below the water tub perimeter rim when the lid is positioned in the closed configuration with respect to the water tub;

the lid further comprising a gases inlet configured to be sealingly connected to a gases inlet of the humidification compartment, wherein the gases inlet of the lid is provided with an associated inlet conduit that extends into the interior volume of the humidification chamber;

the lid further comprising a gases outlet configured to be sealingly connected to a gases outlet of the humidification compartment, wherein the gases outlet of the lid has an associated outlet conduit extending into the interior volume of the humidification chamber; and a flexible seal provided about a perimeter of the humidification chamber between the lid and the water tub, the seal sealingly engaging the perimeter rim of the water tub and the ledge of the lid when the chamber is closed to seal the chamber;

wherein the humidification chamber is configured to be received in the humidification compartment of the respiratory assistance device such that the water tub rests upon the heater base within the compartment.

19. The respiratory assistance device of claim 18, wherein the lid and water chamber are pivotably connected such that the lid pivots away from the water tub when in the open configuration.

20. The respiratory assistance device of claim 18, wherein the inlet conduit directs the inlet gases flow stream into a central zone or region of the lid.

21. The respiratory assistance device of claim 18, wherein the inlet conduit comprises one or more bends or turns.

22. The respiratory assistance device of claim 18, wherein the outlet conduit extends into a central zone or region of the lid.

23. The respiratory assistance device of claim 18, wherein a flow directing formation is provided at the exit of the inlet conduit to direct the gases stream exiting the inlet conduit.

24. The respiratory assistance device of claim 18, further comprising one or more clips configured to engage with a complementary catch for securing the lid in the closed position; wherein the one or more clips comprises an engagement aperture on the lid and its complementary catch is a protrusion or formation that is aligned with the clip such that it engages into the engagement aperture of the clip when the clip is in an engaged position to secure the lid in the closed position, wherein the protrusion or formation comprises a camming surface that is configured to cause its respective clip to pivot or flex outwardly before snapping into the fully engaged position with the complementary catch, when the lid is moved into the closed position without the user needing to operate the clip in order to engage it with the complementary catch.

25. The respiratory assistance device of claim 18, wherein the water tub is provided with a heat transfer contact surface that protrudes from an underside of the water tub base surface.

26. The respiratory assistance device of claim 25, wherein the heat transfer contact surface is of a depth relative to a remainder of the base surface of the water tub that it enables it to extend through an aperture and protrude below the underside of the water tub base surface.

27. The respiratory assistance device of claim 18, wherein the chamber is provided with a protrusion that extends from the surface of the perimeter wall, the protrusion being configured to engage with aligned rails on the humidification compartment.

28. The respiratory assistance device of claim 27, wherein the rim of the water tub is continuous.

29. The respiratory assistance device of claim 18, wherein the ledge of the lid is provided about the entire perimeter wall of the lid.

30. The respiratory assistance device of claim 18, wherein the humidification compartment is an open or exposed compartment.

* * * * *